(12) United States Patent
Kuo et al.

(10) Patent No.: US 10,787,413 B2
(45) Date of Patent: Sep. 29, 2020

(54) DERIVATIVES OF CURCUMINOIDS AND USE THEREOF AS AN ANTICANCER AGENT

(71) Applicant: CHINA MEDICAL UNIVERSITY, Taichung (TW)

(72) Inventors: Sheng-Chu Kuo, Taichung (TW); Kuo-Hsiung Lee, Taichung (TW); Chang-Hai Tsai, Taichung (TW); Min-Tsang Hsieh, Taichung (TW); Ling-Chu Chang, Taichung (TW); Hsin-Yi Hung, Taichung (TW); Hui-Yi Lin, Taichung (TW); Jai-Sing Yang, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 1 day.

(21) Appl. No.: 16/098,207

(22) PCT Filed: Jun. 2, 2017

(86) PCT No.: PCT/US2017/035814
§ 371 (c)(1),
(2) Date: Nov. 1, 2018

(87) PCT Pub. No.: WO2017/218219
PCT Pub. Date: Dec. 21, 2017

(65) Prior Publication Data
US 2019/0161430 A1    May 30, 2019

Related U.S. Application Data

(60) Provisional application No. 62/349,208, filed on Jun. 13, 2016.

(51) Int. Cl.
| | | |
|---|---|---|
| *C07C 69/675* | (2006.01) |
| *C07C 49/255* | (2006.01) |
| *C07C 69/16* | (2006.01) |
| *A61P 35/00* | (2006.01) |
| *A61K 31/12* | (2006.01) |
| *A61K 31/222* | (2006.01) |
| *A61K 31/225* | (2006.01) |
| *A61K 31/704* | (2006.01) |
| *C07C 69/34* | (2006.01) |

(52) U.S. Cl.
CPC ............ *C07C 69/675* (2013.01); *A61K 31/12* (2013.01); *A61K 31/222* (2013.01); *A61K 31/225* (2013.01); *A61K 31/704* (2013.01); *A61P 35/00* (2018.01); *C07C 49/255* (2013.01); *C07C 69/16* (2013.01); *C07C 69/34* (2013.01)

(58) Field of Classification Search
CPC ..... C07C 69/675; C07C 49/255; C07C 69/16; C07C 69/34; A61P 35/00; A61K 31/12; A61K 31/222; A61K 31/225; A61K 31/704
USPC ......................................................... 514/506
See application file for complete search history.

(56) References Cited

U.S. PATENT DOCUMENTS

| | | | |
|---|---|---|---|
| 7,968,115 B2 * | 6/2011 | Kurzrock | A61K 9/1272 424/450 |
| 2015/0011494 A1 | 1/2015 | Vander Jagt et al. | |
| 2016/0038641 A1 | 2/2016 | Cashman et al. | |

* cited by examiner

*Primary Examiner* — Yevgeny Valenrod
(74) *Attorney, Agent, or Firm* — Bacon & Thomas, PLLC

(57) ABSTRACT

A series of novel bis(hydroxymethyl) alkanoate derivatives of curcuminoids were designed, and synthesized, which show anticancer activity, and in particular to breast cancer, colon cancer, and prostate cancer.

20 Claims, 9 Drawing Sheets

DERIVATIVES OF CURCUMINOIDS AND USE THEREOF AS AN ANTICANCER AGENT

FIELD OF THE INVENTION

The present invention is related to a novel anti-cancer agent, and in particular to novel bis(hydoxymethyl) alkanoate derivatives useful for treating breast cancer, colon cancer and prostate cancer.

BACKGROUND OF THE INVENTION

Breast cancer is the most prevalent form of cancer diagnosed in women in the world. According to a recent report[1], in 2015, the estimated number of new cases of female breast cancer in the United States was 2,310,840 which accounted for 29.5% of the total cancer cases. Between 1975 and 2011, the incidence rates of breast cancer remained the highest compared with other cancers[1].

Triple-Negative Breast cancer (TNBC) represents about 15 to 20 percent of all breast cancer cases. This type of cancer cells are called TNBC cells due to lack of Estrogen receptors (ER), Progesterone receptors (PR), and low expression of human epidermal growth factor receptor-2 (HER-2)[2]. TNBC, more common in young women, is known to be an aggressive cancer with poor prognosis and very prone to exacerbation. Due to the lacking of well-defined molecular target drugs, TNBC is normally treated by cytotoxic agents such as Doxorubicin and paclitaxel. These agents are cytotoxic in nature, and are known to develop drug resistance in TNBC cells readily. Therefore, the development of an anti-TNBC drug with less toxicity and drug resistance remains an important medical need.

Natural product mimics are continuously a major source of drug leads and drug candidates. According to the analysis of new marketed medicines, from 1981 to 2010, approved by US Food and Drug Administration (FDA) at 2012, about 34% of new drug are based on small molecule derived from natural products[3]. Plants of Zingiberaceae family have been used as spices and folk medicines in Asian country for centuries. The rhizome of *curcuma longa*, commonly named turmeric, is a rhizomatous herbaceous perennial plant of the ginger family and used as spices, flavoring agent, food preservative, coloring agent and medicine for thousands of years. The major component, curcumin [(E,E)-1,7-bis (4-hydroxy-3-methoxyphenyl)-1,6-heptadiene-3,5-dione] was isolated in 1815[4], and its structure was subsequently elucidated in 1910[5].

Curcumin has a highly conjugated structure containing a heptadiene-3,5-diketone linking with two methoxylated phenol; therefore, curcumin possesses strong free radical trapping ability as a potent antioxidan[6,7,8]. Extensive research shows that curcumin modulates numerous targets[9] and exhibits many biological activities[10]. In terms of its anticancer activity, curcumin inhibits different stages of cancer progression[11]. Moreover, curcumin is proven safe, even at doses up to 8 gram per day in one clinical study[12]. Therefore, curcumin seems to be an ideal drug candidate that affects multiple pathways, and more importantly, it is pharmacologically safe.

The critical disadvantages of curcumin as a drug are its low bioavailability caused by poor hydrophilicity and its rapid in vivo metabolism[13]. To address its poor hydrophilicity, several new dosage forms of curcumin have been tested in recent years, including nanoparticles, liposomes, cyclodextrin encapsulation, micelles and phospholipid complexes, for improving its bioavailability. So far, however, none of these dosage forms have passed the clinical trial and new drug approval[12,13]. The key to its second disadvantage of rapid in vivo metabolism is the presence of two phenolic OH groups on the curcumin structure which is easily metabolized by transferase, through a phase II transformation, into glucuronide and sulfate[14,15,16]. Since the resulted water soluble metabolites are easily eliminated, the half-life of curcumin is very short. Several studies reported the derivatization of curcumin on its phenolic groups to ester prodrugs, leading to curcumin succinate[17], amino acid-linked curcumin[18], and phosphorylated curcumin derivatives[17]. Nonetheless, the in vivo anticancer efficacy data of these curcumin prodrugs were not available on the literature.

SUMMARY OF THE INVENTION

In this invention, curcumin was selected as a lead compound and the bis(hydroxymethyl) alkanoate analogs of curcuminoids (21a-44) were designed as target compounds. The structures of the lead curcumin and ((1E,3Z, 6E)-3-hydroxy-5-oxohepta-1,3,6-triene-1,7-diyl)bis(2-methoxy-4,1-phenylene)bis(3-hydroxy-2-hydroxymethyl)-2-methyl propanoate (21a), the representative target compound, are shown as follows:

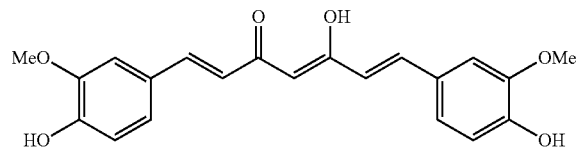

Curcumin (pKa 8.863)

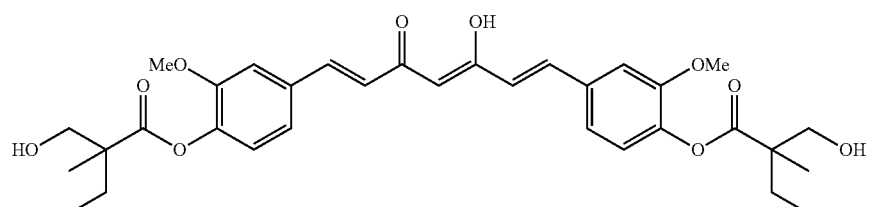

21a (pKa 13.584)

As shown above, on the structure of target compound 21a, both the two phenolic OH groups on lead curcumin were esterified, and bulky groups were added at the end of the ester linking. Theoretically, this type of ester linkage could only be hydrolyzed by esterase in relatively low speed, which delays the exposure of phenolic OH of lead curcumin to glucuronyl transferases and sulphotransferases. Although the four aliphatic OH groups on compound 21a are also susceptible to glucuronidation or sulfonation, forming glucuronides and sulfonates, the pKa of 21a was 13.584 (calculated by chemdraw Ultra 14.0) which is higher than pKa of curcumin (8.863, calculated). This indicated that 21a is more resistant than curcumin to metabolism by glucuronidation or sulfonation.

The logarithmic partition coefficient (log P) of compound 21a is 1.73 (calculated) exhibiting better hydrophilicity than that of curmin (log P 3.38 (calculated)). In fact, the solubility of 21a in either water or alcohol is better than that of curcumin.

Based on the above description, the target compound 21a may improve the pharmacokinetic critical disadvantage of curcumin. The investigation results indicated that the anticancer activity of 21a is more potent than curcumin, not only in vivo, but also in vitro tests which were not predictable in advance. In this invention, a series of new 21a analogs were designed, synthesized, and evaluated for anticancer activity. Several potential anticancer drug candidates were identified and thus disclosed herein.

Preferable embodiments of the present invention include (but not limited) the features recited in the accompanied claims at the end of the specification.

BRIEF DESCRIPTION OF THE DRAWINGS

FIGS. 2A and 2B show in vivo Antitumor Activity of 21a and curcumin, wherein FIG. 2A and FIG. 2B are plots showing mean tumor size-time profiles and mean body weight-time profiles in MDA-MB-231 Xenograft nude mice (n=11) following PO dosing of 21a at 5, 10, 25, 50 mg/kg/day and curcumin at 100 mg/kg/day, respectively.

FIGS. 3A and 3B show in vivo Antitumor Activity of 21a combined with Doxorubicin, wherein FIG. 3A and FIG. 3B are plots showing mean tumor size-time profiles in MDA-MB-231 Xenograft nude mice (n=5); and mean body weight-time profiles in MDA-MB-231 Xenograft nude mice (n=5) following PO dosing of 21a at 50 mg/kg/day, IP dosing of Doxorubicin at 1 mg/kg/day and combination of 21a and Doxorubicin, respectively.

In FIG. 4B, cells cultured with or without 10 μM of 21a for 24 h were examined for changes in cell morphology and were photographed using a phase-contrast microscope as described in Materials and methods.

In FIG. 5A, cells were treated with 5 μM of 21a for 24 h, and the cell cycle distribution was determined using flow cytometric analysis and cell cycle distribution was quantified. In FIG. 5B, cells were exposed to 21a (5 μM) and then incubated for 0, 4, 8, 16 and 24 h. The protein levels of Cyclin B, CDK1 and β-actin in 21a-treated MDA-MB-231 cells were determined by Western blotting. In FIG. 5C, CDK1 activity was examined by an in vitro kinase activity assay. Data are presented as the mean±S.E.M. of three independent experiments.

DETAILED DESCRIPTION OF THE INVENTION

1. Results and Discussion 1-1. Chemistry

Figure 1:
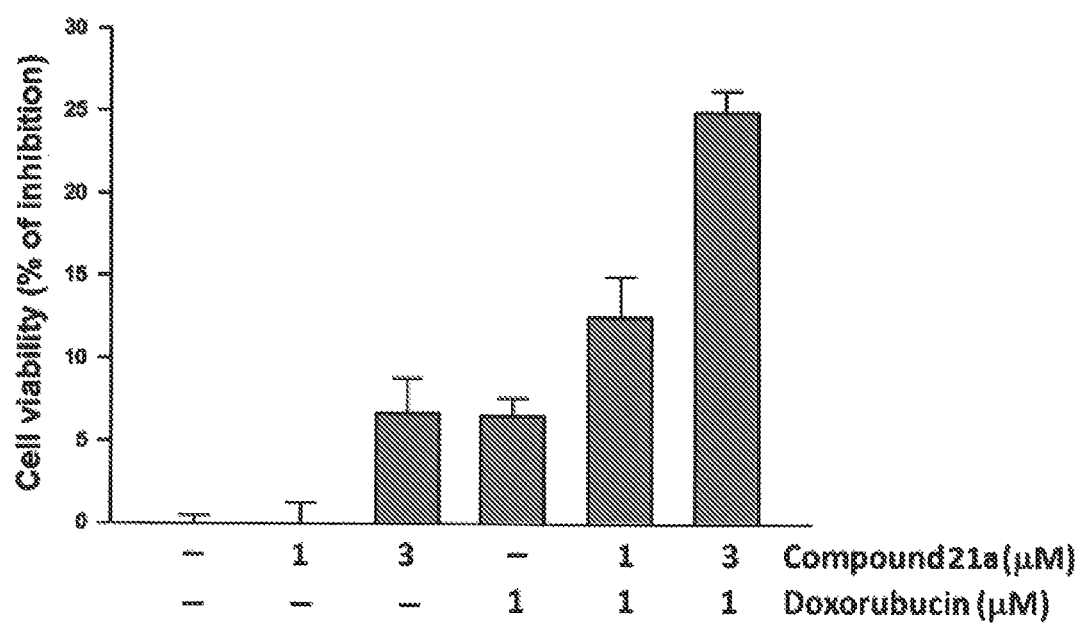
FIG. 1 is a plot shows combination effects of compound 21a and Doxorubicin.

In general, the target compounds (21a-44) were synthesized according to Schemes 1-5. As shown, phenolic compounds including curcumin, bisdemethoxycurcumin, compound 1, 2, 3, 4 and 5 were reacted with acids (compound 7a and 7b) in the presence of 1-Ethyl-3-(3-dimethylaminopropyl)carbodiimide (EDCI), HOBt (Hydroxybenzotriazole) and N,N-dimethylaminopyridine (DMAP) in DMF to give the diverse ester derivatives (compound 8a-19) (scheme1). The ester compounds obtained were then underwent deprotection reaction in THF under acid catalysis at 45-50° C. to give the corresponding hydroxyl ester compounds (compound 21a-31) as shown in scheme 2. Compound 9b was subjected to methylation with $K_2CO_3$ or $Cs_2CO_3$ as base and followed by acid-promoted hydrolysis at 45-50° C. for a period time (2-3 hours) to give the target compound 33 in 35% yield (Scheme 2). In another manner, two alkyl groups were introduced into the β-diketone system, wherein compound 8a, 10a and 11a were mixed with bases and alkyl halides to produce corresponding ester intermediates and followed by acid-promoted hydrolysis to provide the desired compound 35a-35e, 36 and 37 in 30-45% yield, respectively (Scheme 3). Curcumin was reacted with 3-hydroxy-2,2-bis(hydroxymethyl)propanoic acid in the presence of 1-Ethyl-3-(3-dimethylaminopropyl) carbodiimide (EDCI), HOBt (Hydroxybenzotriazole) and N,N-dimethylaminopyridine (DMAP) in DMF to give the compound 38a and 38b (scheme 4, eq. 1). Compound 8s was treated with DBU and followed by formaldehyde in THF to give compound 39, which was followed by acid-promoted hydrolysis at room temperature to give compound 40 in 13% yield (scheme 4, eq. 2). Compound 39 was acetylated and acid-promoted hydrolysis to give compound 41 (scheme 4, eq. 3). Dimethylcurcumin was reacted was treated with DBU and followed by formaldehyde in THF to give compound 42, (scheme 5, eq. 1). Compound 42 was esterized with 2,2,5-trimethyl-1,3-dioxane-5-carbonyl chloride and followed by acid-promoted hydrolysis to give compound 43 (scheme 5, eq. 2). Otherwise, compound 42 was acetylated to give compound 44 (scheme 5, eq. 3)

Scheme 1 eq.1

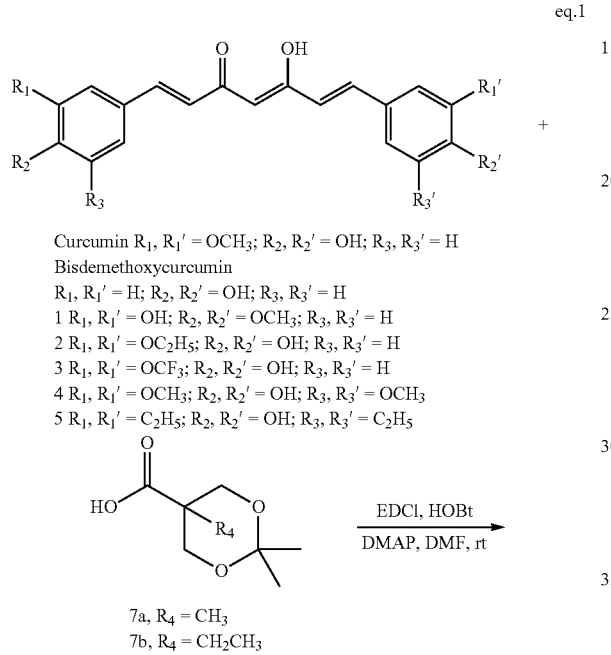

Curcumin $R_1, R_1' = OCH_3$; $R_2, R_2' = OH$; $R_3, R_3' = H$
Bisdemethoxycurcumin
$R_1, R_1' = H$; $R_2, R_2' = OH$; $R_3, R_3' = H$
1 $R_1, R_1' = OH$; $R_2, R_2' = OCH_3$; $R_3, R_3' = H$
2 $R_1, R_1' = OC_2H_5$; $R_2, R_2' = OH$; $R_3, R_3' = H$
3 $R_1, R_1' = OCF_3$; $R_2, R_2' = OH$; $R_3, R_3' = H$
4 $R_1, R_1' = OCH_3$; $R_2, R_2' = OH$; $R_3, R_3' = OCH_3$
5 $R_1, R_1' = C_2H_5$; $R_2, R_2' = OH$; $R_3, R_3' = C_2H_5$

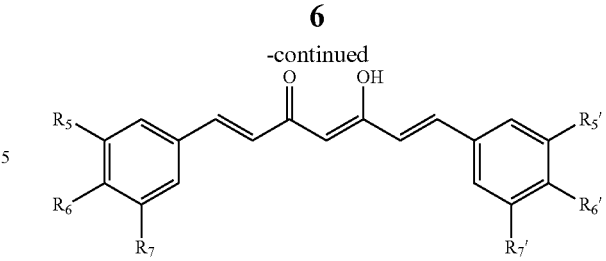

7a, $R_4 = CH_3$
7b, $R_4 = CH_2CH_3$

-continued

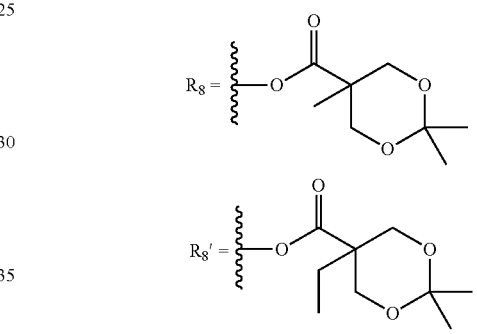

8a $R_5, R_5' = OCH_3$; $R_6, R_6' = OR_8$; $R_7, R_7' = H$
8b $R_5, R_5' = OCH_3$; $R_6 = OR_8'$, $R_6' = OH$; $R_7, R_7' = H$
9a $R_5, R_5' = OCH_3$; $R_6, R_6' = OR_8$; $R_7, R_7' = H$
9b $R_5, R_5' = OCH_3$; $R_6 = OR_8'$, $R_6' = OH$; $R_7, R_7' = H$
10a $R_5, R_5' = H$; $R_6, R_6' = OR_8$; $R_7, R_7' = H$
10b $R_5, R_5' = H$; $R_6 = OR_8'$, $R_6' = OH$; $R_7, R_7' = H$
11a $R_5, R_5' = OR_8$; $R_6, R_6' = OCH_3$; $R_7, R_7' = H$
11b $R_5 = OR_8$, $R_5' = OH$; $R_6, R_6' = OCH_3$; $R_7, R_7' = H$
12a $R_5, R_5' = OR_8'$; $R_6, R_6' = OCH_3$; $R_7, R_7' = H$
12b $R_5 = OR_8'$, $R_5' = OH$; $R_6, R_6' = OCH_3$; $R_7, R_7' = H$
13 $R_5, R_5' = OC_2H_5$; $R_6, R_6' = OR_8$; $R_7, R_7' = H$
14 $R_5, R_5' = OC_2H_5$; $R_6, R_6' = OR_8'$; $R_7, R_7' = H$
15 $R_5, R_5' = OCF_3$; $R_6, R_6' = OR_8$; $R_7, R_7' = H$
16 $R_5, R_5' = OCF_3$; $R_6, R_6' = OR_8'$; $R_7, R_7' = H$
17 $R_5, R_5' = OCH_3$; $R_6, R_6' = OR_8$; $R_7, R_7' = OCH_3$
18 $R_5, R_5' = C_2H_5$; $R_6, R_6' = OR_8$; $R_7, R_7' = C_2H_5$

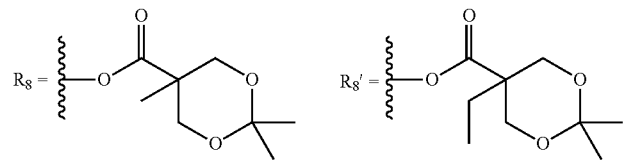

Scheme 2 eq. 1

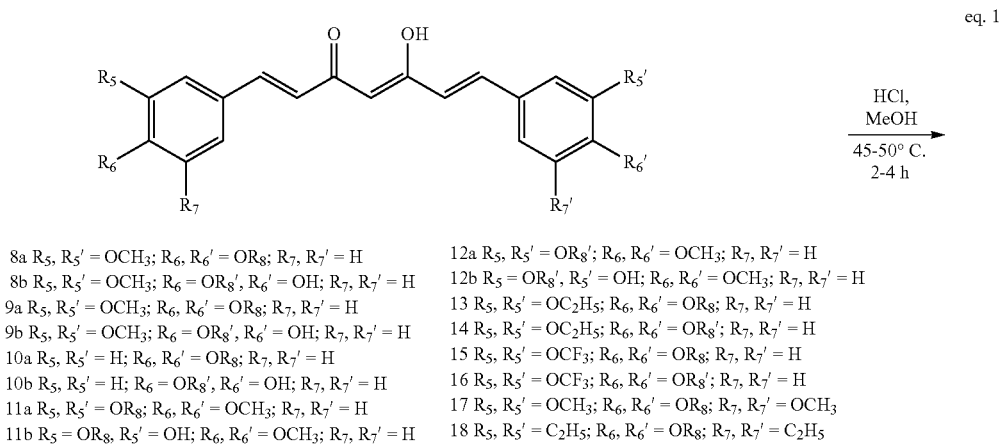

8a $R_5, R_5' = OCH_3$; $R_6, R_6' = OR_8$; $R_7, R_7' = H$
8b $R_5, R_5' = OCH_3$; $R_6 = OR_8'$, $R_6' = OH$; $R_7, R_7' = H$
9a $R_5, R_5' = OCH_3$; $R_6, R_6' = OR_8$; $R_7, R_7' = H$
9b $R_5, R_5' = OCH_3$; $R_6 = OR_8'$, $R_6' = OH$; $R_7, R_7' = H$
10a $R_5, R_5' = H$; $R_6, R_6' = OR_8$; $R_7, R_7' = H$
10b $R_5, R_5' = H$; $R_6 = OR_8'$, $R_6' = OH$; $R_7, R_7' = H$
11a $R_5, R_5' = OR_8$; $R_6, R_6' = OCH_3$; $R_7, R_7' = H$
11b $R_5 = OR_8$, $R_5' = OH$; $R_6, R_6' = OCH_3$; $R_7, R_7' = H$

12a $R_5, R_5' = OR_8'$; $R_6, R_6' = OCH_3$; $R_7, R_7' = H$
12b $R_5 = OR_8'$, $R_5' = OH$; $R_6, R_6' = OCH_3$; $R_7, R_7' = H$
13 $R_5, R_5' = OC_2H_5$; $R_6, R_6' = OR_8$; $R_7, R_7' = H$
14 $R_5, R_5' = OC_2H_5$; $R_6, R_6' = OR_8'$; $R_7, R_7' = H$
15 $R_5, R_5' = OCF_3$; $R_6, R_6' = OR_8$; $R_7, R_7' = H$
16 $R_5, R_5' = OCF_3$; $R_6, R_6' = OR_8'$; $R_7, R_7' = H$
17 $R_5, R_5' = OCH_3$; $R_6, R_6' = OR_8$; $R_7, R_7' = OCH_3$
18 $R_5, R_5' = C_2H_5$; $R_6, R_6' = OR_8$; $R_7, R_7' = C_2H_5$

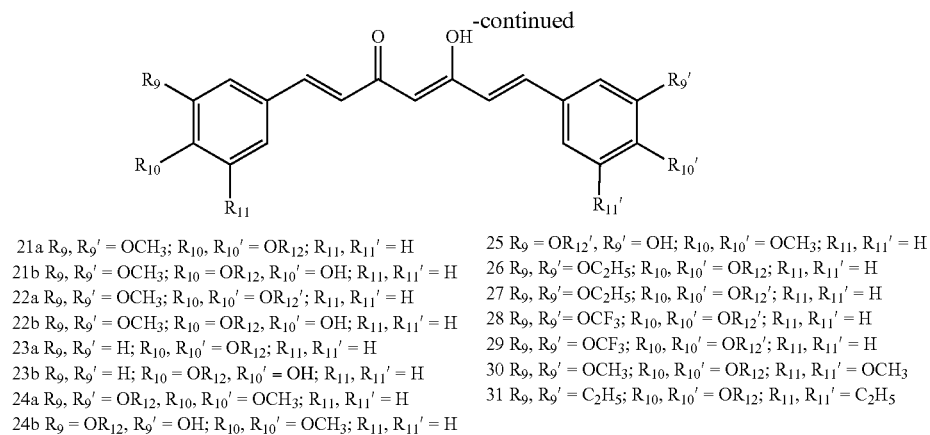

21a R$_9$, R$_9'$ = OCH$_3$; R$_{10}$, R$_{10}'$ = OR$_{12}$; R$_{11}$, R$_{11}'$ = H
21b R$_9$, R$_9'$ = OCH$_3$; R$_{10}$ = OR$_{12}$, R$_{10}'$ = OH; R$_{11}$, R$_{11}'$ = H
22a R$_9$, R$_9'$ = OCH$_3$; R$_{10}$, R$_{10}'$ = OR$_{12}'$; R$_{11}$, R$_{11}'$ = H
22b R$_9$, R$_9'$ = OCH$_3$; R$_{10}$ = OR$_{12}$, R$_{10}'$ = OH; R$_{11}$, R$_{11}'$ = H
23a R$_9$, R$_9'$ = H; R$_{10}$, R$_{10}'$ = OR$_{12}$; R$_{11}$, R$_{11}'$ = H
23b R$_9$, R$_9'$ = H; R$_{10}$ = OR$_{12}$, R$_{10}'$ = OH; R$_{11}$, R$_{11}'$ = H
24a R$_9$ = OR$_{12}$, R$_9'$ = OH; R$_{10}$, R$_{10}'$ = OCH$_3$; R$_{11}$, R$_{11}'$ = H
24b R$_9$ = OR$_{12}$, R$_9'$ = OH; R$_{10}$, R$_{10}'$ = OCH$_3$; R$_{11}$, R$_{11}'$ = H

25 R$_9$ = OR$_{12}'$, R$_9'$ = OH; R$_{10}$, R$_{10}'$ = OCH$_3$; R$_{11}$, R$_{11}'$ = H
26 R$_9$, R$_9'$ = OC$_2$H$_5$; R$_{10}$, R$_{10}'$ = OR$_{12}$; R$_{11}$, R$_{11}'$ = H
27 R$_9$, R$_9'$ = OC$_2$H$_5$; R$_{10}$, R$_{10}'$ = OR$_{12}'$; R$_{11}$, R$_{11}'$ = H
28 R$_9$, R$_9'$ = OCF$_3$; R$_{10}$, R$_{10}'$ = OR$_{12}$; R$_{11}$, R$_{11}'$ = H
29 R$_9$, R$_9'$ = OCF$_3$; R$_{10}$, R$_{10}'$ = OR$_{12}'$; R$_{11}$, R$_{11}'$ = H
30 R$_9$, R$_9'$ = OCH$_3$; R$_{10}$, R$_{10}'$ = OR$_{12}$; R$_{11}$, R$_{11}'$ = OCH$_3$
31 R$_9$, R$_9'$ = C$_2$H$_5$; R$_{10}$, R$_{10}'$ = OR$_{12}$; R$_{11}$, R$_{11}'$ = C$_2$H$_5$

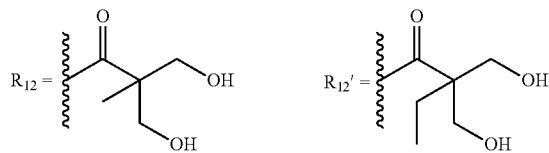

eq. 3

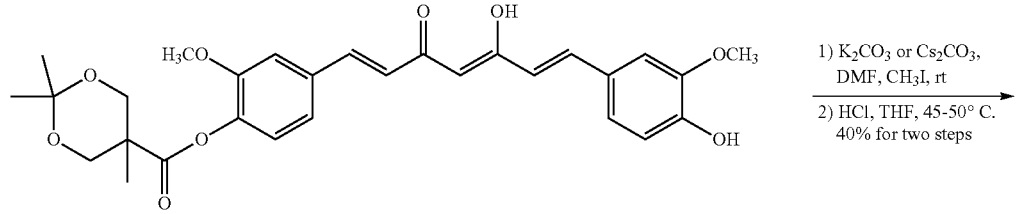

9b

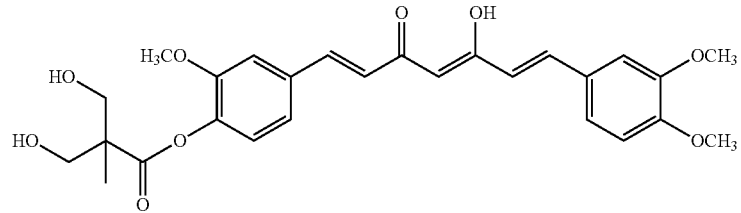

33

Scheme 3

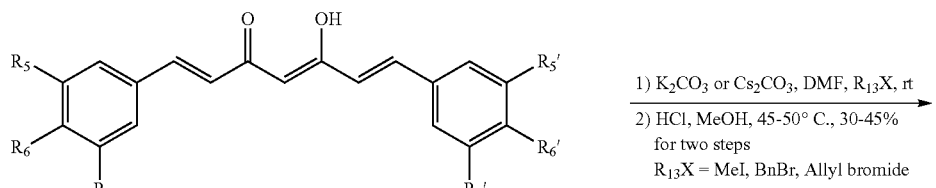

1) K$_2$CO$_3$ or Cs$_2$CO$_3$, DMF, R$_{13}$X, rt
2) HCl, MeOH, 45-50° C., 30-45% for two steps
R$_{13}$X = MeI, BnBr, Allyl bromide propagyl bromide 8a R$_5$, R$_5'$ = OCH$_3$; R$_6$, R$_6'$ = OR$_8$; R$_7$, R$_7'$ = H
10a R$_5$, R$_5'$ = H; R$_6$, R$_6'$ = OR$_8$; R$_7$, R$_7'$ = H
11a R$_5$, R$_5'$ = OR$_8$; R$_6$, R$_6'$ = OCH$_3$; R$_7$, R$_7'$ = H

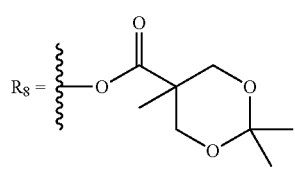

-continued
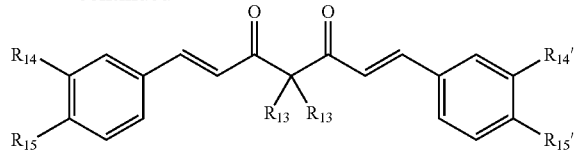
35a $R_{14}, R_{14}' = OCH_3$; $R_{15}, R_{15}' = OR_{12}$; $R_{13} = Me$
35b $R_{14}, R_{14}' = OCH_3$; $R_{15}, R_{15}' = OR_{12}$; $R_{13} = Et$
35c $R_{14}, R_{14}' = OCH_3$; $R_{15}, R_{15}' = OR_{12}$; $R_{13} = Bn$
35d $R_{14}, R_{14}' = OCH_3$; $R_{15}, R_{15}' = OR_{12}$; $R_{13} = Propagyl$
35e $R_{14}, R_{14}' = OCH_3$; $R_{15}, R_{15}' = OR_{12}$; $R_{13} = Allyl$
36 $R_{14}, R_{14}' = H$; $R_{15}, R_{15}' = OR_{12}$; $R_{13} = Me$
37 $R_{14}, R_{14}' = OR_{12}$; $R_{15}, R_{15}' = OCH_3$; $R_{13} = Me$
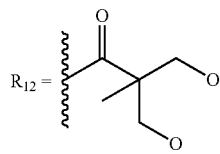
Scheme 4
eq. 1
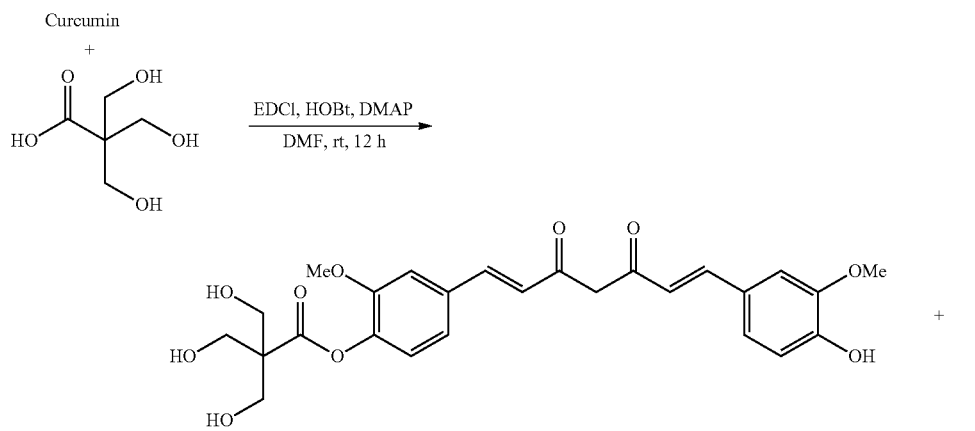
38a
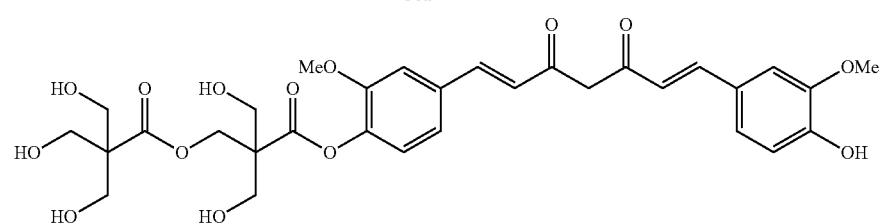
38b
eq. 2
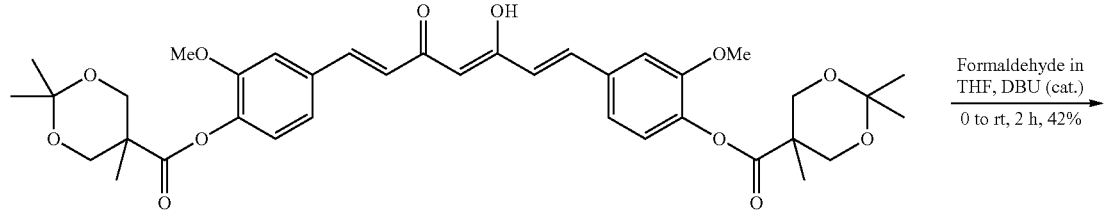
8a -continued
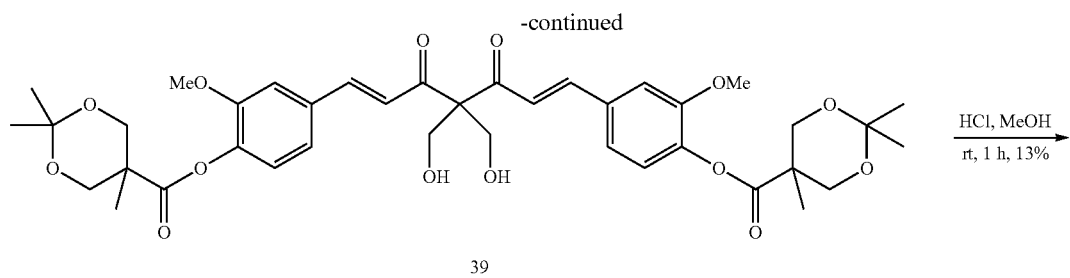
39
HCl, MeOH
rt, 1 h, 13%
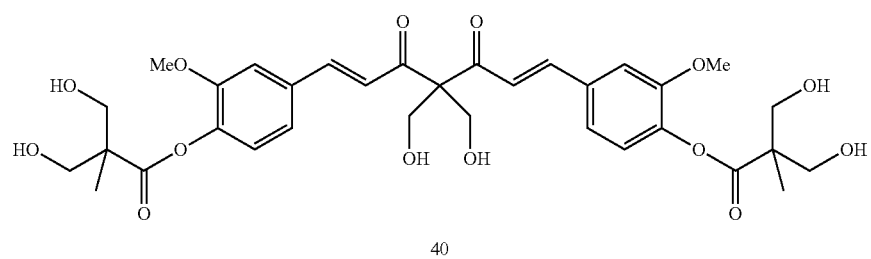
40
eq. 3
39 + acetyl chloride  
1) NEt₃, DCM, rt, 12 h  
2) HCl, MeOH, 7% for two steps
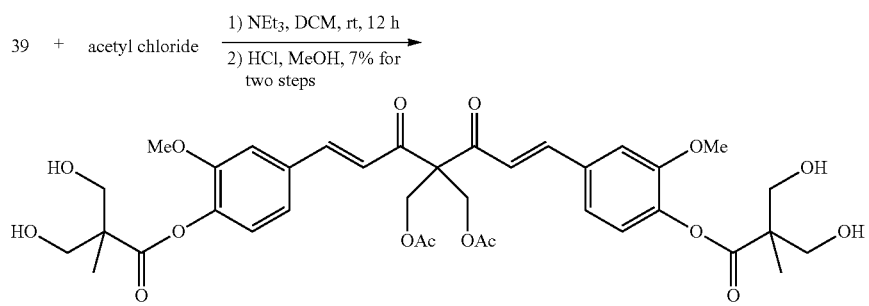
41
Scheme 5
eq. 1
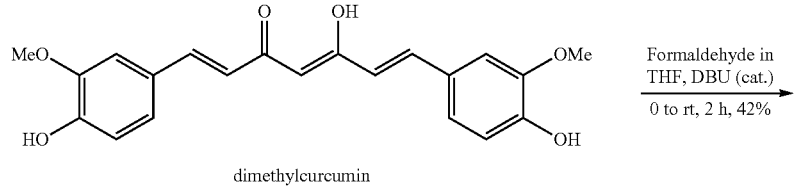
dimethylcurcumin
Formaldehyde in THF, DBU (cat.)
0 to rt, 2 h, 42%
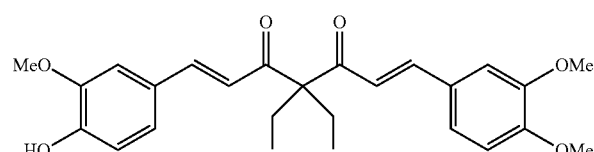
42

-continued
eq. 2
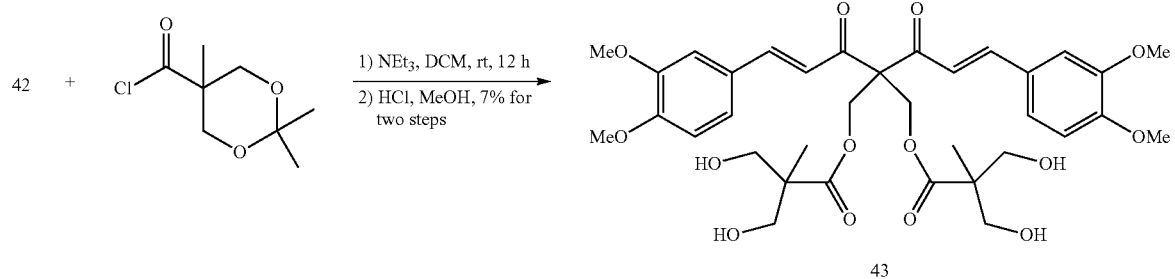
eq. 3
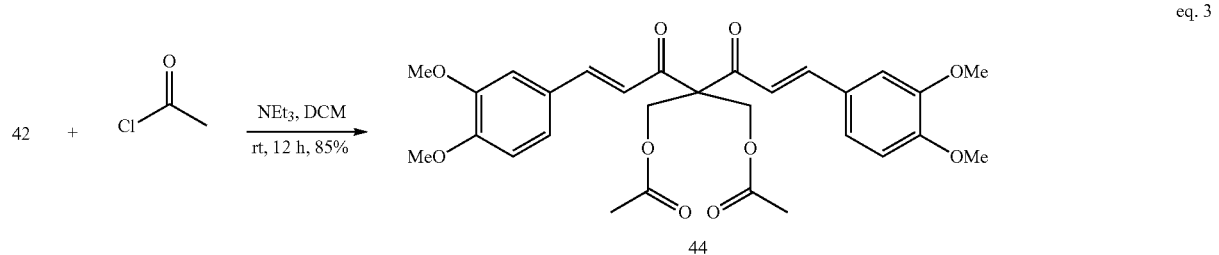

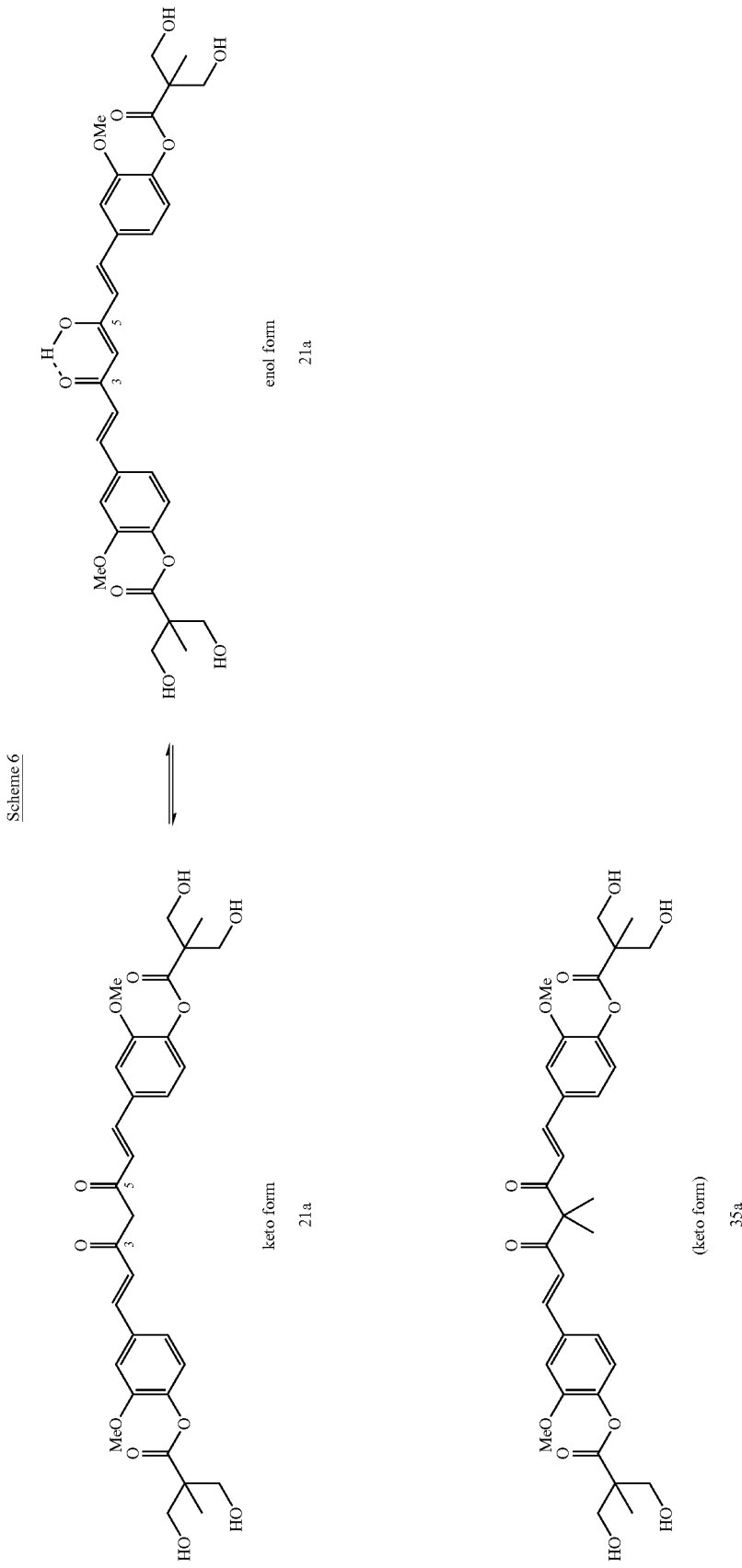

1-2. Growth Inhibitory Activity of Target Compounds 21a-44 Against MDA-MB-231, HCT116 and PC-3 Cancer Cell Lines.

The designed and synthesized target compounds 21a-44 and positive control, curcumin, were screened against MDA-MB-231 (TNBC), HCT-116 (colon cancer) and PC-3 (prostate cancer) cell lines, and the results are summarized in Table 1A~1C. Besides, the stability of 21a in the culture media was tested. The media, after 72 h treatment, containing the representative target compound 21a was analyzed for the presence of curcumin, the possible hydrolyzed product from 21a. The result indicated that 21a is stable in the test media, and that curcumin did not contribute the growth inhibitory activity of 21a.

Table 1A summarized the inhibitory activity of compounds 21a -44 against MDA-MB-321 cell lines. The positive control curcumin and all of the target compounds 21a-44 showed increasing inhibitory activity with treatment time up to 72 h. Also, all of the target compounds demonstrated better inhibitory activity than the positive control. The structure activity relationship derived from Table 1A were described in the following.

When both two phenolic hydroxyl functionalities of curcumin were esterified by reacting with bis(hydroxymethyl) propanoic acids to from 21a, the $IC_{50}$ value improved to 2.67 μM which is 6.2 times higher than that of curcumin (16.23 μM). Further replacement of both the methyl groups on the ester substituent of 21a with ethyl (22a) slightly improved $IC_{50}$ (2.00 μM).

Even if only one of two phenolic hydroxyl groups was esterified, the $IC_{50}$ of resulted compound 21b (5.94 μM) is still more potent that of curcumin control, but a little weaker than 21a. Subsequently, the replacement of the methyl group on the ester substituent of 21b with ethyl (22b) also resulted in slightly improved $IC_{50}$ (4.66 μM). Next, if both of the two methoxy on phenyl ring on curcumin were removed, before esterification, the $IC_{50}$ of the yielded 23a (6.74 μM) is slightly weaker than 21a, but is still more potent than curcumin. As an alternative, only one phenyl 4-OH group was esterified, the $IC_{50}$ of the yielded 23b (1.33 μM) surprisingly boosted to about 12 times more potent than curcumin.

In a different approach, if the position of 3-$OCH_3$ and 4-OH were exchanged, then the $IC_{50}$ of the yielded di-ester derivative 24a (4.61 μM) is weaker than 21a, but still about 3.5 times more potent than curcumin. For comparison, the monoester alternative 24b exhibits slightly better $IC_{50}$ (2.29 μM) than its di-ester counterpart 24a. Furthermore, replacement of the methyl on the ester substituent on 24b with ethyl 25 resulted in weaker $IC_{50}$ of 3.85 μM. It is worth mentioned that similar structural change from 21a to 22a or 21b to 22b resulted in slightly improved $IC_{50}$ values. If one of the phenolic OH of curcumin was methoxylated, and the other was esterified, the afforded compound 33 showed $IC_{50}$ of 2.55 μM which is comparable with that of 21a.

As shown in Scheme 6, compound 21a possess the heptadiene-3, 5-dione moiety which is readily interconvertible between keto and enol forms. The 3- or 5-OH group on the enol form binds via hydrogen binding with the neighboring 5- or 3-C=O, respectively, which stabilizes its structure. It is of great research interest to determine if such tautomerism affects their biological activity. In this invention, two methyl functionalities were incorporated onto the 4-position of 21a and afforded (1E, 6E)-4, 4-dimethyl-3,5-dioxohepta-1, 6-diene-1,7-diyl)bis(2-methoxy-4,1-phenylene)bis(3-hydroxy-2-hydroxymethyl)-2-methyl propanoate (35a) which is found to possess stable keto form, and is not able to tautomerization. Thus, in this research, 35a was used as a new lead compound and derived into a series of its 4, 4-dialkyl derivatives (35a-35f, 36 and 37) with stable keto form. These target compounds were synthesized and then evaluated for their inhibitory activity against MDA-MB-231 cells. The incorporation of two methyl groups onto 4-position of 21a resulted in 35a with $IC_{50}$ strengthened from 2.67 μM to 1.98 μM, which is 8.2 times more potent than curcumin ($IC_{50}$ 16.23 μM). Meanwhile, the replacement of two 4-methyl of 35a with two ethyl (35b) or benzyl (35c) weakened their activity, and the replacement with two prop-2-ynyl (35d) further weakened its activity to give $IC_{50}$ of 4.9 μM, but this is still more potent than curcumin. However, incorporation of two allyl moiety into the 4-position of 21a resulted the formation of 35e, which showed strong anti-MDA-MB-231 activity with a $IC_{50}$ of 0.71 μM.

Among the above four target compounds 35(a-e), 35e, demonstrated the greatest enhancement in anticancer activity and was further modified subsequently. The removal of the 3'- and 3''-$OCH_3$ from 35a gave compound 36 with $IC_{50}$ of 2.89 μM which is slightly weaker than the 35a, but is somewhat more potent than the corresponding analog 23a ($IC_{50}$ 6.74 μM). Then, the exchange if the substituents on the 3'- and 3''-position of 35a with those on 4'- and 4''-position, respectively, afforded 37 ($IC_{50}$ 2.70 μM) with anticancer activity weaker than 35a, but slightly more potent than its corresponding analog 24a ($IC_{50}$ 4.61 μM).

To sum up, all of the target compounds (21a-44) showed increasing inhibitory activity with treatment time up to 72 h. After 72 h treatment, the target compounds showed 2.4-22.8 times stronger inhibitory activity than the curcumin control against the MDA-MB-231 TNBC cell line.

Meanwhile, the inhibitory activity of compounds 21a-44 against HCT-116 colon cancer and PC-3 prostate cancer cell lines were summarized in Tables 1B and 1C. Similar to the result shown in Table 1A, the inhibitory activity of compounds 21a-44 against these two cancer cell lines also increasing treatment time up to 72 h. Except compound 21b, most of the target compounds also demonstrated better inhibitory activity than the curcumin control.

For further evaluation of the anticancer activity of these target compounds, one of compounds 21a-44 was selected. Judge from their relative ease of synthesis, the diester derivatives (21a, 22a, 23a and 24a) were selected first. Then considered their relative inhibitory activity against the MDA-MB-231 cell, (22a>21a>24a>23a), together with their relative hydrophilicity, indicated by lower log p, in which 21a (1.73 μm) is lower than 22a (2.56 μm), 23a (1.91 μm) and 23a (2.12 μm). It is obvious that compound 21a was selected as candidate for further evaluation.

On the other hand, from the 4, 4-dialkyl analogs (35a-e, 36 and 37), the representative compound, 35e was selected as a backup compound for the development of 21a.

1-3. Growth Inhibitory Activity of 21a Against Breast Cancer Cell Lines

Compound 21a and curcumin were evaluated for inhibitory activity against $ER^+/PR^+$ breast cancer cells (MCF-7, T47D), HER $2^+$ breast cancer cells (SKBR3. BT474 and MDA-MB-457) and Triple-negative breast cancer cells (HS-578T, MDA-MB-157, and MDA-MB-468) cell lines. The result in Table 2 indicated that 21a exhibited significant inhibitory activity against various breast cancer cell lines with potency about 2.4 ~8.2 times greater than curcumin.

The common clinical drug for treating $ER^+/PR^+$ breast cancer is Tamoxifen, and the target therapeutic drugs for HER $2^+$ breast cancer are Herceptin and Tylemect. However, all these drugs have adverse effects and have developed drug resistance easily. Thus, there is still a clinical need for the development of effective and safe new drugs for these breast cancer treatment. As mentioned in the Background of the Invention section, due to the lack of well-defined molecular target for TNBC, the current treatment uses cytotoxic drugs which are toxic in nature and develop drug resistance readily. Therefore, there is urgent need for the development of new TNBC drugs.

The data in Table 2 indicated that 21a is a potential anti-breast cancer drug candidate, especially against TNBC.

The inhibitor activity of 21a and 35a was further tested against Doxorubicin-resistant MDA-MB-231 cancer cell line and the result indicated that 21a ($IC_{50}$ 6.5 μM) and 35a ($IC_{50}$ 5.7 μM) showed 10 times greater inhibitory activity than curcumin ($IC_{50}$ 57.6 μM) (Table 2). Meanwhile, 21a was used in combination with Doxorubicin to treat MDA-MB-231 and resulted inhibitory activity was shown in FIG. 1, in which the presence of synergistic effect was clearly observed. This again confirmed the developmental.

TABLE 1A

The IC$_{50}$ of curcumoid derivatives in cell viability of MDA-MB-231 breast cancer cell

| Compound | R$_3$' | R$_3$" | R$_4$' | R$_4$" | R$_4$ | R$_5$', R$_5$" | IC$_{50}^{a,b}$ (μM) 24 hours | 48 hours | 72 hours |
|---|---|---|---|---|---|---|---|---|---|
| Curcumin | OCH$_3$ | OCH$_3$ | OH | OH | H | H | 38.77 ± 3.35 | 22.05 ± 2.97 | 16.23 ± 0.14 |
| Bis-demethoxy-curcumin | H | H | OH | OH | H | H | >100 | 26.92 ± 0.19 | 27.53 ± 0.42 |
| 1 | OH | OH | OCH$_3$ | OCH$_3$ | H | H | >100 | 6.93 ± 0.06 | 6.55 ± 0.29 |
| 21a | OCH$_3$ | OCH$_3$ | —O—C(=O)—C(CH$_3$)(OH)—CH$_2$OH | —O—C(=O)—C(CH$_3$)(OH)—CH$_2$OH | H | H | 5.37 ± 1.22 | 3.06 ± 0.18 | 2.67 ± 0.18 |
| 22a | OCH$_3$ | OCH$_3$ | —O—C(=O)—C(C$_2$H$_5$)(OH)—CH$_2$OH | —O—C(=O)—C(C$_2$H$_5$)(OH)—CH$_2$OH | H | H | 4.71 ± 0.29 | 2.56 ± 0.18 | 2.00 ± 0.16 |
| 21b | OCH$_3$ | OCH$_3$ | —O—C(=O)—C(CH$_3$)(OH)—CH$_2$OH | OH | H | H | 13.18 ± 1.20 | 9.97 ± 1.12 | 5.94 ± 0.78 |
| 22b | OCH$_3$ | OCH$_3$ | —O—C(=O)—C(C$_2$H$_5$)(OH)—CH$_2$OH | OH | H | H | 14.55 ± 2.42 | 7.55 ± 0.86 | 4.66 ± 0.34 |
| 23a | H | H | —O—C(=O)—C(CH$_3$)(OH)—CH$_2$OH | —O—C(=O)—C(CH$_3$)(OH)—CH$_2$OH | H | H | 26.66 ± 1.85 | 7.82 ± 0.56 | 6.74 ± 0.54 |

TABLE 1A-continued

The IC$_{50}$ of curcumoid derivatives in cell viability of MDA-MB-231 breast cancer cell

| Compound | R$_3$' | R$_3$" | R$_4$' | R$_4$" | R$_4$ | R$_5$', R$_5$" | IC$_{50}^{a,b}$ (μM) 24 hours | 48 hours | 72 hours |
|---|---|---|---|---|---|---|---|---|---|
| 23b | —O—C(=O)—C(OH)(CH$_3$)(OH) | H | —O—C(=O)—C(OH)(CH$_3$)(OH) | OH | H | H | 19.52 ± 1.82 | 5.27 ± 0.57 | 1.33 ± 0.05 |
| 24a | OCH$_3$ | —O—C(=O)—C(OH)(CH$_3$)(OH) | OCH$_3$ | OCH$_3$ | H | H | 9.22 ± 2.24 | 5.11 ± 0.96 | 4.61 ± 0.25 |
| 24b | —O—C(=O)—C(OH)(CH$_3$)(OH) | OH | OCH$_3$ | OCH$_3$ | H | H | 7.69 ± 0.82 | 1.99 ± 0.99 | 2.29 ± 0.15 |
| 25 | —O—C(=O)—C(OH)(C$_2$H$_5$)(OH) | OH | OCH$_3$ | OCH$_3$ | H | H | 9.64 ± 0.07 | 4.94 ± 0.03 | 3.85 ± 0.03 |
| 26 | OC$_2$H$_5$ | OC$_2$H$_5$ | —O—C(=O)—C(OH)(CH$_3$)(OH) | —O—C(=O)—C(OH)(CH$_3$)(OH) | H | H | 18.43 ± 0.15 | 8.85 ± 0.66 | 6.58 ± 0.81 |
| 27 | OC$_2$H$_5$ | OC$_2$H$_5$ | —O—C(=O)—C(OH)(C$_2$H$_5$)(OH) | —O—C(=O)—C(OH)(C$_2$H$_5$)(OH) | H | H | 8.04 ± 0.17 | 7.43 ± 1.36 | 5.49 ± 0.52 |

TABLE 1A-continued

The IC$_{50}$ of curcumoid derivatives in cell viability of MDA-MB-231 breast cancer cell

| Compound | R$_3$' | R$_3$" | R$_4$' | R$_4$" | R$_4$ | R$_5$', R$_5$" | IC$_{50}^{a,b}$ (μM) 24 hours | 48 hours | 72 hours |
|---|---|---|---|---|---|---|---|---|---|
| 28 | OCF$_3$ | OCF$_3$ | O=C−O−, −C(OH)(CH$_3$)−OH | O=C−O−, −C(OH)(CH$_3$)−OH | H | H | 16.56 ± 3.04 | 8.60 ± 0.74 | 7.78 ± 0.09 |
| 29 | OCF$_3$ | OCF$_3$ | O=C−O−, −C(OH)(C$_2$H$_5$)−OH | O=C−O−, −C(OH)(C$_2$H$_5$)−OH | H | H | 9.48 ± 0.44 | 7.79 ± 0.61 | 7.22 ± 0.41 |
| 30 | OCH$_3$ | OCH$_3$ | O=C−O−, −C(OH)(CH$_3$)−OH | O=C−O−, −C(OH)(CH$_3$)−OH | H | OCH$_3$ | 17.51 ± 2.85 | 8.90 ± 1.28 | 6.19 ± 0.04 |
| 31 | C$_2$H$_5$ | C$_2$H$_5$ | O=C−O−, −C(OH)(CH$_3$)−OH | O=C−O−, −C(OH)(CH$_3$)−OH | H | C$_2$H$_5$ | 8.68 ± 0.07 | 7.40 ± 0.63 | 3.82 ± 0.03 |
| 33 | OCH$_3$ | OCH$_3$ | O=C−O−, −C(OH)(CH$_3$)−OH | OCH$_3$ | H | H | 4.69 ± 0.73 | 3.12 ± 0.17 | 2.55 ± 0.17 |
| 35a | OCH$_3$ | OCH$_3$ | O=C−O−, −C(OH)(CH$_3$)−OH | O=C−O−, −C(OH)(CH$_3$)−OH | CH$_3$ | H | 5.33 ± 0.69 | 2.25 ± 0.1 | 1.98 ± 0.04 |

TABLE 1A-continued

The IC$_{50}$ of curcumoid derivatives in cell viability of MDA-MB-231 breast cancer cell

| Compound | R$_3$' | R$_4$' | R$_4$'' | R$_3$'' | R$_4$ | R$_5$', R$_5$'' | IC$_{50}^{a,b}$ (μM) | | |
|---|---|---|---|---|---|---|---|---|---|
| | | | | | | | 24 hours | 48 hours | 72 hours |
| 35b | OCH$_3$ | O=C-O- / OH-C(CH$_3$)-OH | O=C-O- / OH-C(CH$_3$)-OH | OCH$_3$ | —C$_2$H$_5$ | H | 8.64 ± 0.27 | 3.02 ± 0.15 | 2.00 ± 0.02 |
| 35c | OCH$_3$ | O=C-O- / OH-C(CH$_3$)-OH | O=C-O- / OH-C(CH$_3$)-OH | OCH$_3$ | Bn | H | 6.03 ± 2.52 | 2.45 ± 0.24 | 2.11 ± 0.04 |
| 35d | OCH$_3$ | O=C-O- / OH-C(CH$_3$)-OH | O=C-O- / OH-C(CH$_3$)-OH | OCH$_3$ | —CH$_2$C≡CH | H | 28.53 ± 5.29 | 5.87 ± 0.10 | 4.90 ± 0.08 |
| 35e | OCH$_3$ | O=C-O- / OH-C(CH$_3$)-OH | O=C-O- / OH-C(CH$_3$)-OH | OCH$_3$ | —CH$_2$CH=CH$_2$ | H | 9.02 ± 0.50 | 3.13 ± 0.54 | 0.71 ± 0.22 |
| 36 | H | O=C-O- / OH-C(CH$_3$)-OH | O=C-O- / OH-C(CH$_3$)-OH | H | CH$_3$ | H | 7.74 ± 0.41 | 3.13 ± 0.04 | 2.98 ± 0.09 |
| 37 | O=C-O- / OH-C(CH$_3$)-OH | OCH$_3$ | OCH$_3$ | O=C-O- / OH-C(CH$_3$)-OH | CH$_3$ | H | 7.60 ± 0.94 | 2.71 ± 0.23 | 2.70 ± 0.15 |

TABLE 1A-continued

The IC$_{50}$ of curcumoid derivatives in cell viability of MDA-MB-231 breast cancer cell

| Compound | R$_3$' | R$_3$" | R$_4$' | R$_4$" | R$_4$ | R$_5$', R$_5$" | IC$_{50}^{a,b}$ (μM) 24 hours | 48 hours | 72 hours |
|---|---|---|---|---|---|---|---|---|---|
| 38a | OCH$_3$ | OCH$_3$ | –O–C(=O)–C(OH)(CH$_2$OH)(OH) | OH | H | H | 47.31 ± 1.31 | 21.11 ± 1.01 | 17.54 ± 1.62 |
| 38b | OCH$_3$ | OCH$_3$ | –O–C(=O)–C(OH)(CH$_2$OH)(OH) | OH | H | H | 82.62 ± 1.67 | 64.76 ± 2.39 | 55.27 ± 3.20 |
| 40 | OCH$_3$ | OCH$_3$ | –O–C(=O)–C(OH)(CH$_3$)(OH) | –O–C(=O)–C(OH)(CH$_3$)(OH) | –CH$_2$OH | H | >100 | 84.92 ± 1.67 | 57.88 ± 2.73 |
| 41 | OCH$_3$ | OCH$_3$ | –O–C(=O)–C(OH)(CH$_3$)(OH) | –O–C(=O)–C(OH)(CH$_3$)(OH) | –CH$_2$OAc | H | 57.62 ± 1.59 | 6.55 ± 0.04 | 3.69 ± 0.02 |
| 42 | OCH$_3$ | OCH$_3$ | OCH$_3$ | OCH$_3$ | CH$_2$OH | H | >100 | 53.50 ± 3.45 | 9.02 ± 1.13 |
| 43 | OCH$_3$ | OCH$_3$ | OCH$_3$ | OCH$_3$ | –CH$_2$–O–C(=O)–C(OH)(OH) | H | 83.00 ± 0.17 | 57.43 ± 2.06 | 17.3 ± 0.10 |
| 44 | OCH$_3$ | OCH$_3$ | OCH$_3$ | OCH$_3$ | –CH$_2$OAc | H | 7.21 ± 0.18 | 0.90 ± 0.03 | 0.61 ± 0.10 |

[a] MDA-MB-231 cancer cells were treated with different concentration of compounds for 24, 48 and 72 hours,
[b] Data are presented as IC$_{50}$ (μM, the concentration of 50% proliferation-inhibitory effect).

TABLE 1B

The IC$_{50}$ of curcumoid derivatives in cell viability of HCT-116 colon cancer cell

| Compound | $R_3'$ | $R_3''$ | $R_4'$ | $R_4''$ | $R_4$ | $R_5'$, $R_5''$ | IC$_{50}^{a,b}$ (μM) 24 hours | 48 hours | 72 hours |
|---|---|---|---|---|---|---|---|---|---|
| Curcumin | OCH$_3$ | OCH$_3$ | OH | OH | H | H | 78.04 ± 11.22 | 26.33 ± 1.38 | 13.77 ± 0.50 |
| Bisdemethoxy-curcumin | H | H | OH | OH | H | H | >100 | 29.56 ± 0.78 | 23.65 ± 2.43 |
| 1 | OH | OH | OCH$_3$ | OCH$_3$ | H | H | >100 | 6.76 ± 0.13 | 5.59 ± 0.12 |
| 21a | OCH$_3$ | OCH$_3$ | O=C(CH$_3$)(OH)–O– with OH | O=C(CH$_3$)(OH)–O– with OH | H | H | 10.49 ± 1.03 | 6.25 ± 0.596 | 3.91 ± 0.27 |
| 22a | OCH$_3$ | OCH$_3$ | O=C(C$_2$H$_5$)(OH)–O– with OH | O=C(C$_2$H$_5$)(OH)–O– with OH | H | H | 5.82 ± 0.56 | 2.40 ± 0.32 | 1.34 ± 0.04 |
| 21b | OCH$_3$ | OCH$_3$ | O=C(CH$_3$)(OH)–O– with OH | OH | H | H | 35.57 ± 2.50 | 20.44 ± 0.61 | 15.48 ± 0.16 |
| 22b | OCH$_3$ | OCH$_3$ | O=C(C$_2$H$_5$)(OH)–O– with OH | OH | H | H | 21.192 ± 2.48 | 12.42 ± 0.16 | 11.40 ± 1.05 |
| 23a | H | H | O=C(CH$_3$)(OH)–O– with OH | O=C(CH$_3$)(OH)–O– with OH | H | H | 57.39 ± 12.25 | 8.64 ± 0.18 | 4.10 ± 0.06 |

TABLE 1B-continued

The IC$_{50}$ of curcumoid derivatives in cell viability of HCT-116 colon cancer cell

| Compound | R$_3'$ | R$_3''$ | R$_4'$ | R$_4''$ | R$_4$ | R$_5'$, R$_5''$ | IC$_{50}{}^{a,b}$ (μM) 24 hours | 48 hours | 72 hours |
|---|---|---|---|---|---|---|---|---|---|
| 23b | H | H | -OC(=O)C(CH$_3$)(OH)CH$_2$OH | OH | H | H | 71.91 ± 7.87 | 11.32 ± 0.72 | 4.78 ± 0.66 |
| 24a | -OC(=O)C(CH$_3$)(OH)CH$_2$OH | -OC(=O)C(CH$_3$)(OH)CH$_2$OH | OCH$_3$ | OCH$_3$ | H | H | 11.41 ± 1.11 | 5.33 ± 0.29 | 2.79 ± 0.15 |
| 24b | OH | OH | OCH$_3$ | OCH$_3$ | H | H | 7.57 ± 1.02 | 3.84 ± 0.41 | 1.95 ± 0.15 |
| 25 | -OC(=O)C(C$_2$H$_5$)(OH)CH$_2$OH | -OC(=O)C(C$_2$H$_5$)(OH)CH$_2$OH | OCH$_3$ | OCH$_3$ | H | H | 7.62 ± 0.41 | 4.77 ± 0.10 | 3.64 ± 0.03 |
| 26 | OC$_2$H$_5$ | OC$_2$H$_5$ | -OC(=O)C(CH$_3$)(OH)CH$_2$OH | -OC(=O)C(CH$_3$)(OH)CH$_2$OH | H | H | 8.33 ± 0.39 | 4.22 ± 0.05 | 3.79 ± 0.10 |
| 27 | OC$_2$H$_5$ | OC$_2$H$_5$ | -OC(=O)C(C$_2$H$_5$)(OH)CH$_2$OH | -OC(=O)C(C$_2$H$_5$)(OH)CH$_2$OH | H | H | 3.79 ± 0.03 | 3.18 ± 0.26 | 2.97 ± 0.13 |

TABLE 1B-continued

The IC$_{50}$ of curcumoid derivatives in cell viability of HCT-116 colon cancer cell

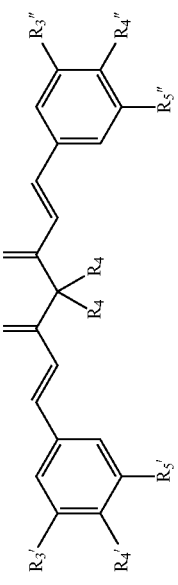

| Compound | $R_3'$ | $R_3''$ | $R_4'$ | $R_4''$ | $R_4$ | $R_5'$, $R_5''$ | IC$_{50}^{a,b}$ (μM) 24 hours | 48 hours | 72 hours |
|---|---|---|---|---|---|---|---|---|---|
| 28 | OCF$_3$ | OCF$_3$ | O=C(−O−)(OH)(CH$_3$)(OH) | O=C(−O−)(OH)(CH$_3$)(OH) | H | H | 8.94 ± 0.66 | 7.11 ± 0.07 | 6.27 ± 0.10 |
| 29 | OCF$_3$ | OCF$_3$ | O=C(−O−)(OH)(C$_2$H$_5$)(OH) | O=C(−O−)(OH)(C$_2$H$_5$)(OH) | H | H | 7.43 ± 0.10 | 4.69 ± 0.49 | 4.38 ± 0.26 |
| 30 | OCH$_3$ | OCH$_3$ | O=C(−O−)(OH)(CH$_3$)(OH) | O=C(−O−)(OH)(CH$_3$)(OH) | H | OCH$_3$ | 8.34 ± 0.83 | 4.77 ± 0.44 | 5.18 ± 0.76 |
| 31 | C$_2$H$_5$ | C$_2$H$_5$ | O=C(−O−)(OH)(CH$_3$)(OH) | O=C(−O−)(OH)(CH$_3$)(OH) | H | C$_2$H$_5$ | 7.21 ± 0.21 | 3.67 ± 0.01 | 3.51 ± 0.01 |
| 33 | OCH$_3$ | OCH$_3$ | O=C(−O−)(OH)(CH$_3$)(OH) | OCH$_3$ | H | H | 10.52 ± 0.64 | 7.56 ± 0.77 | 4.77 ± 0.24 |
| 35a | OCH$_3$ | OCH$_3$ | O=C(−O−)(OH)(CH$_3$)(OH) | O=C(−O−)(OH)(CH$_3$)(OH) | CH$_3$ | H | 6.67 ± 0.43 | 3.35 ± 0.09 | 1.65 ± 0.16 |

TABLE 1B-continued

The IC$_{50}$ of curcumoid derivatives in cell viability of HCT-116 colon cancer cell

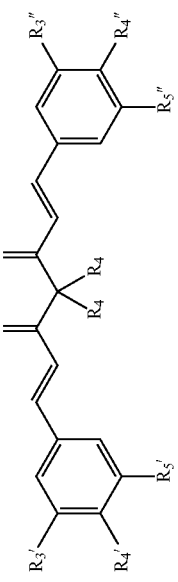

| Compound | R$_3$' | R$_4$' | R$_3$" | R$_4$" | R$_4$ | R$_5$', R$_5$" | IC$_{50}$$^{a,b}$ (μM) 24 hours | 48 hours | 72 hours |
|---|---|---|---|---|---|---|---|---|---|
| 35b | OCH$_3$ | O=C(−O−)C(OH)(CH$_3$)(OH) | OCH$_3$ | O=C(−O−)C(OH)(CH$_3$)(OH) | —C$_2$H$_5$ | H | 7.71 ± 0.03 | 1.93 ± 0.01 | 1.74 ± 0.02 |
| 35c | OCH$_3$ | O=C(−O−)C(OH)(CH$_3$)(OH) | OCH$_3$ | O=C(−O−)C(OH)(CH$_3$)(OH) | Bn | H | 12.89 ± 2.03 | 7.66 ± 0.61 | 3.88 ± 0.16 |
| 35d | OCH$_3$ | O=C(−O−)C(OH)(CH$_3$)(OH) | OCH$_3$ | O=C(−O−)C(OH)(CH$_3$)(OH) | —CH$_2$C≡CH | H | 14.52 ± 1.01 | 5.81 ± 0.23 | 3.92 ± 0.24 |
| 35e | OCH$_3$ | O=C(−O−)C(OH)(CH$_3$)(OH) | OCH$_3$ | O=C(−O−)C(OH)(CH$_3$)(OH) | —CH$_2$CH=CH$_2$ | H | 2.18 ± 0.22 | 0.92 ± 0.06 | 0.71 ± 0.01 |
| 36 | H | O=C(−O−)C(OH)(CH$_3$)(OH) | H | O=C(−O−)C(OH)(CH$_3$)(OH) | CH$_3$ | H | 4.12 ± 0.10 | 3.43 ± 0.20 | 2.63 ± 0.06 |
| 37 | O=C(−O−)C(OH)(CH$_3$)(OH) | OCH$_3$ | O=C(−O−)C(OH)(CH$_3$)(OH) | OCH$_3$ | CH$_3$ | H | 5.90 ± 1.87 | 2.71 ± 0.39 | 1.26 ± 0.04 |

TABLE 1B-continued

The IC$_{50}$ of curcumoid derivatives in cell viability of HCT-116 colon cancer cell

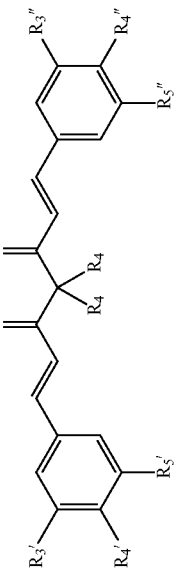

| Compound | R$_3$' | R$_4$' | R$_3$" | R$_4$" | R$_4$ | R$_5$', R$_5$" | IC$_{50}$$^{a,b}$ (μM) 24 hours | 48 hours | 72 hours |
|---|---|---|---|---|---|---|---|---|---|
| 38a | OCH$_3$ | ![OH, C(CH$_2$OH)$_2$OH ester] | OCH$_3$ | OH | H | H | 39.59 ± 0.23 | 18.36 ± 0.62 | 9.86 ± 0.01 |
| 38b | OCH$_3$ | ![bis-ester structure] | OCH$_3$ | OH | H | H | 75.04 ± 3.10 | 61.30 ± 2.85 | 43.68 ± 1.36 |
| 40 | OCH$_3$ | ![ester with CH$_3$, OH groups] | OCH$_3$ | ![ester with CH$_3$, OH groups] | —CH$_2$OH | H | >100 | 69.08 ± 3.11 | 58.04 ± 0.53 |
| 41 | OCH$_3$ | ![ester with CH$_3$, OH groups] | OCH$_3$ | ![ester with CH$_3$, OH groups] | —CH$_2$OAc | H | 9.52 ± 0.06 | 6.53 ± 0.01 | 5.40 ± 0.02 |
| 42 | OCH$_3$ | OCH$_3$ | OCH$_3$ | OCH$_3$ | CH$_2$OH | H | 89.65 ± 0.49 | 8.00 ± 0.60 | 7.18 ± 0.68 |
| 43 | OCH$_3$ | OCH$_3$ | OCH$_3$ | OCH$_3$ | ![CH$_2$-O-C(=O)-C(OH)(OH)] | H | 64.65 ± 1.56 | 40.10 ± 1.61 | 25.09 ± 0.50 |
| 44 | OCH$_3$ | OCH$_3$ | OCH$_3$ | OCH$_3$ | —CH$_2$OAc | H | 6.33 ± 1.01 | 3.66 ± 0.25 | 1.51 ± 0.55 |

$^a$HCT-116 cancer cells were treated with different concentration of compounds for 24, 48 and 72 hours.
$^b$Data are presented as IC$_{50}$ (μM, the concentration of 50% proliferation-inhibitory effect).

TABLE 1C

The IC$_{50}$ of curcumoid derivatives in cell viability of PC3 prostate cancer cell

| Compound | R$_3$' | R$_3$" | R$_4$' | R$_4$" | R$_4$ | R$_5$', R$_5$" | IC$_{50}$$^{a,b}$ (μM) 24 hours | 48 hours | 72 hours |
|---|---|---|---|---|---|---|---|---|---|
| Curcumin | OCH$_3$ | OCH$_3$ | OH | OH | H | H | 57.06 ± 10.08 | 30.03 ± 0.72 | 18.80 ± 1.31 |
| Bis-demethoxy-curcumin | H | H | OH | OH | H | H | >100 | 28.54 ± 1.09 | 26.89 ± 4.36 |
| 1 | OH | OH | OCH$_3$ | OCH$_3$ | H | H | >100 | >100 | >100 |
| 21a | OCH$_3$ | OCH$_3$ | -O-C(=O)-C(CH$_3$)(OH)(OH) | -O-C(=O)-C(CH$_3$)(OH)(OH) | H | H | 7.80 ± 0.03 | 6.00 ± 0.35 | 3.90 ± 0.08 |
| 22a | OCH$_3$ | OCH$_3$ | -O-C(=O)-C(C$_2$H$_5$)(OH)(OH) | -O-C(=O)-C(C$_2$H$_5$)(OH)(OH) | H | H | 6.91 ± 0.67 | 5.12 ± 0.29 | 4.21 ± 0.14 |
| 21b | OCH$_3$ | OCH$_3$ | -O-C(=O)-C(CH$_3$)(OH)(OH) | OH | H | H | 24.62 ± 0.83 | 26.77 ± 0.74 | 17.41 ± 1.37 |
| 22b | OCH$_3$ | OCH$_3$ | -O-C(=O)-C(C$_2$H$_5$)(OH)(OH) | OH | H | H | 13.83 ± 1.48 | 14.43 ± 0.82 | 12.50 ± 0.1 |
| 23a | H | H | -O-C(=O)-C(CH$_3$)(OH)(OH) | -O-C(=O)-C(CH$_3$)(OH)(OH) | H | H | 8.46 ± 0.64 | 8.77 ± 0.80 | 5.59 ± 0.20 |

TABLE 1C-continued

The IC$_{50}$ of curcumoid derivatives in cell viability of PC3 prostate cancer cell

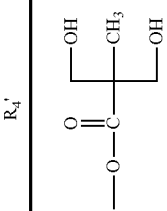

| Compound | R$_3$' | R$_3$'' | R$_4$' | R$_4$'' | R$_4$ | R$_5$', R$_5$'' | IC$_{50}^{a,b}$ (μM) | | |
|---|---|---|---|---|---|---|---|---|---|
| | | | | | | | 24 hours | 48 hours | 72 hours |
| 23b | H | H | —O—C(=O)—C(OH)(CH$_3$)—OH | OH | H | H | 20.10 ± 2.62 | 10.97 ± 0.44 | 5.22 ± 0.27 |
| 24a | —O—C(=O)—C(OH)(CH$_3$)—OH | —O—C(=O)—C(OH)(CH$_3$)—OH | OCH$_3$ | OCH$_3$ | H | H | 11.91 ± 1.40 | 6.43 ± 0.26 | 4.74 ± 0.04 |
| 24b | —O—C(=O)—C(OH)(CH$_3$)—OH | OH | OCH$_3$ | OCH$_3$ | H | H | 8.37 ± 0.81 | 3.75 ± 0.18 | 2.32 ± 0.05 |
| 25 | —O—C(=O)—C(OH)(C$_2$H$_5$)—OH | OH | OCH$_3$ | OCH$_3$ | H | H | 15.90 ± 2.23 | 8.74 ± 0.01 | 7.03 ± 0.12 |
| 26 | OC$_2$H$_5$ | OC$_2$H$_5$ | —O—C(=O)—C(OH)(CH$_3$)—OH | —O—C(=O)—C(OH)(CH$_3$)—OH | H | H | 9.38 ± 0.01 | 9.53 ± 0.36 | 5.36 ± 0.07 |
| 27 | OC$_2$H$_5$ | OC$_2$H$_5$ | —O—C(=O)—C(OH)(C$_2$H$_5$)—OH | —O—C(=O)—C(OH)(C$_2$H$_5$)—OH | H | H | 8.18 ± 1.89 | 4.46 ± 0.15 | 3.06 ± 0.29 |

TABLE 1C-continued

The IC$_{50}$ of curcumoid derivatives in cell viability of PC3 prostate cancer cell

| Compound | $R_3'$ | $R_3''$ | $R_4'$ | $R_4''$ | $R_4$ | $R_5'$, $R_5''$ | IC$_{50}^{a,b}$ (μM) 24 hours | 48 hours | 72 hours |
|---|---|---|---|---|---|---|---|---|---|
| 28 | OCF$_3$ | OCF$_3$ | -O-C(=O)-C(OH)(CH$_3$)(OH) | -O-C(=O)-C(OH)(CH$_3$)(OH) | H | H | 67.12 ± 3.39 | 53.88 ± 3.01 | 30.19 ± 2.37 |
| 29 | OCF$_3$ | OCF$_3$ | -O-C(=O)-C(OH)(C$_2$H$_5$)(OH) | -O-C(=O)-C(OH)(C$_2$H$_5$)(OH) | H | H | 37.04 ± 0.56 | 29.7 ± 2.83 | 8.10 ± 1.56 |
| 30 | OCH$_3$ | OCH$_3$ | -O-C(=O)-C(OH)(CH$_3$)(OH) | -O-C(=O)-C(OH)(CH$_3$)(OH) | H | OCH$_3$ | 7.79 ± 1.42 | 7.70 ± 0.87 | 3.14 ± 0.33 |
| 31 | C$_2$H$_5$ | C$_2$H$_5$ | -O-C(=O)-C(OH)(CH$_3$)(OH) | -O-C(=O)-C(OH)(CH$_3$)(OH) | H | C$_2$H$_5$ | 19.94 ± 1.27 | 7.49 ± 0.18 | 4.14 ± 1.10 |
| 33 | OCH$_3$ | OCH$_3$ | -O-C(=O)-C(OH)(CH$_3$)(OH) | OCH$_3$ | H | H | 7.77 ± 0.88 | 7.85 ± 0.81 | 7.64 ± 0.75 |
| 35a | OCH$_3$ | OCH$_3$ | -O-C(=O)-C(OH)(CH$_3$)(OH) | -O-C(=O)-C(OH)(CH$_3$)(OH) | CH$_3$ | H | 3.49 ± 0.40 | 3.10 ± 0.29 | 1.76 ± 0.14 |

TABLE 1C-continued

The IC$_{50}$ of curcumoid derivatives in cell viability of PC3 prostate cancer cell

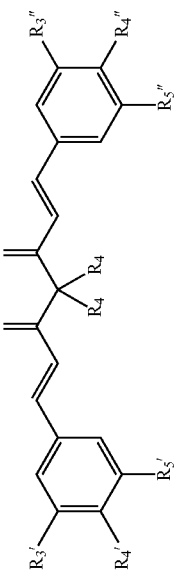

| Compound | R$_3$' | R$_3$" | R$_4$' | R$_4$" | R$_4$ | R$_5$', R$_5$" | IC$_{50}^{a,b}$ (μM) | | |
|---|---|---|---|---|---|---|---|---|---|
| | | | | | | | 24 hours | 48 hours | 72 hours |
| 35b | OCH$_3$ | OCH$_3$ | −O−C(=O)−C(OH)(CH$_3$)(OH) | −O−C(=O)−C(OH)(CH$_3$)(OH) | −C$_2$H$_5$ | H | 8.70 ± 0.14 | 3.67 ± 0.25 | 2.16 ± 0.12 |
| 35c | OCH$_3$ | OCH$_3$ | −O−C(=O)−C(OH)(CH$_3$)(OH) | −O−C(=O)−C(OH)(CH$_3$)(OH) | Bn | H | 17.59 ± 0.14 | 9.09 ± 0.99 | 7.28 ± 0.50 |
| 35d | OCH$_3$ | OCH$_3$ | −O−C(=O)−C(OH)(CH$_3$)(OH) | −O−C(=O)−C(OH)(CH$_3$)(OH) | −CH$_2$C≡CH | H | 17.12 ± 1.74 | 11.51 ± 0.96 | 6.70 ± 0.75 |
| 35e | OCH$_3$ | OCH$_3$ | −O−C(=O)−C(OH)(CH$_3$)(OH) | −O−C(=O)−C(OH)(CH$_3$)(OH) | −CH$_2$CH=CH$_2$ | H | 4.24 ± 0.18 | 3.54 ± 0.26 | 2.63 ± 0.77 |
| 36 | H | H | −O−C(=O)−C(OH)(CH$_3$)(OH) | −O−C(=O)−C(OH)(CH$_3$)(OH) | CH$_3$ | H | 17.05 ± 1.81 | 7.49 ± 0.33 | 3.62 ± 0.11 |
| 37 | −O−C(=O)−C(OH)(CH$_3$)(OH) | −O−C(=O)−C(OH)(CH$_3$)(OH) | OCH$_3$ | OCH$_3$ | CH$_3$ | H | 2.86 ± 0.83 | 1.59 ± 0.24 | 1.84 ± 0.12 |

TABLE 1C-continued

The IC$_{50}$ of curcumoid derivatives in cell viability of PC3 prostate cancer cell

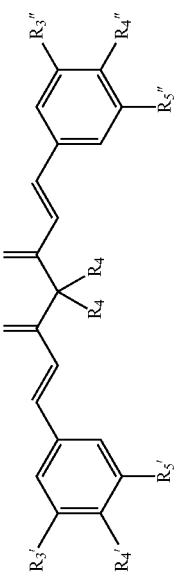

| Compound | R$_3$' | R$_3$" | R$_4$' | R$_4$" | R$_4$ | R$_5$', R$_5$" | IC$_{50}$$^{a,b}$ (μM) 24 hours | 48 hours | 72 hours |
|---|---|---|---|---|---|---|---|---|---|
| 38a | OCH$_3$ | OCH$_3$ | −O−C(=O)−C(CH$_2$OH)(OH)− | OH | H | H | 46.54 ± 0.48 | 34.90 ± 0.20 | 32.68 ± 0.56 |
| 38b | OCH$_3$ | OCH$_3$ | −O−C(=O)−C(CH$_2$OH)(OH)−CH$_2$OH, OH | OH | H | H | 100 | 67.47 ± 1.25 | 63.94 ± 0.47 |
| 40 | OCH$_3$ | OCH$_3$ | −O−C(=O)−C(CH$_3$)(OH)− | −O−C(=O)−C(CH$_3$)(OH)− | −CH$_2$OH | H | >100 | >100 | 74.62 ± 2.04 |
| 41 | OCH$_3$ | OCH$_3$ | −O−C(=O)−C(CH$_3$)(OH)− | −O−C(=O)−C(CH$_3$)(OH)− | −CH$_2$OAc | H | 65.18 ± 1.43 | 47.35 ± 2.65 | 32.76 ± 2.70 |
| 42 | OCH$_3$ | OCH$_3$ | OCH$_3$ | OCH$_3$ | CH$_2$OH | H | 77.17 ± 2.34 | 61.24 ± 2.30 | 26.08 ± 0.81 |
| 43 | OCH$_3$ | OCH$_3$ | OCH$_3$ | OCH$_3$ | −CH$_2$−O−C(=O)−C(OH)(OH)− | H | 67.69 ± 1.76 | 52.18 ± 1.23 | 51.30 ± 0.39 |
| 44 | OCH$_3$ | OCH$_3$ | OCH$_3$ | OCH$_3$ | −CH$_2$OAc | H | 3.68 ± 0.11 | 3.07 ± 0.37 | 0.85 ± 0.07 |

(c) PC-3 cancer cells were treated with different concentration of compounds for 24, 48 and 72 hours.
(d) Data are presented as IC$_{50}$ (μM, the concentration of 50% proliferation-inhibitory effect).

TABLE 2

The IC$_{50}$ of 21a and curcumin in cell viability of various breast cancer cells.

| | | IC$_{50}$ (μM) | |
|---|---|---|---|
| | | Curcumin | 21a |
| ER$^+$/PR$^+$ | T47D | 47.91 ± 3.90 | 19.28 ± 1.71 |
| | MCF-7 | 42.89 ± 2.36 | 6.13 ± 0.51 |
| Her-2$^+$ | MDA-MB-453 | 32.40 ± 1.41 | 3.97 ± 0.27 |
| | BT-474 | 30.14 ± 1.42 | 6.15 ± 0.87 |
| | SKBR-3 | 42.83 ± 1.47 | 6.39 ± 0.43 |
| Triple negative | MDA-MB-468 | 42.89 ± 2.35 | 6.13 ± 0.51 |
| | MDA-MB-157 | 40.38 ± 3.26 | 9.23 ± 0.11 |
| | HS-578T | 55.45 ± 1.39 | 7.96 ± 0.27 |
| | Doxorubicin-resistant MDA-MB-231 | 58.55 ± 4.03 | 6.52 ± 1.70 |

(a) Breast cancer cells were treated with different concentrations of curcumin and 21a for 24 h
(b) Data are presented as IC$_{50}$ (μM, the concentration of 50% proliferation-inhibitory effect)
(c) IC$_{50}$ of 35a on Doxorubicin-resistant MDA-MB-231 is 5.71 ± 1.24.

1-4. In Vivo Antitumor Activity of 21a

Figure 2A:
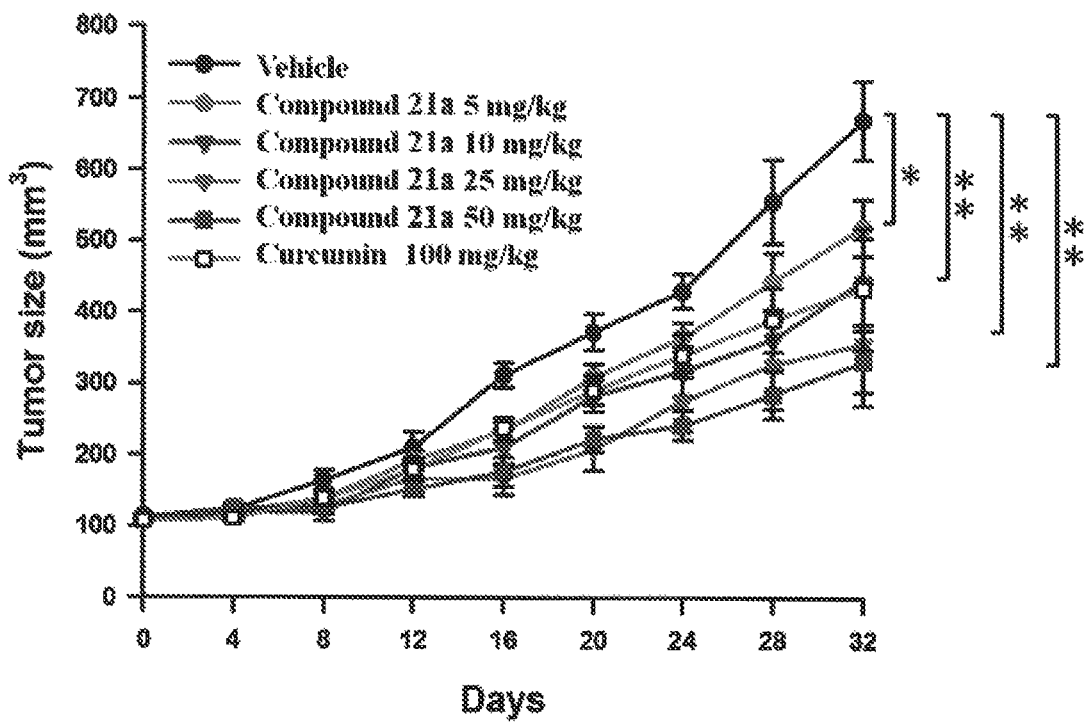

Compound 21a was evaluated in the MDA-MB-231 Xenograft nude mice model by oral route (PO) at dose of 5, 10, 25 and 50 mg/kg/day, and curcumin at 100 mg/kg/day dose was used as positive control. As shown in FIG. 2A, compound 21a induced dose- and time-dependent inhibition of MDA-MB-231 tumor growth. 21a exhibited significant antitumor activity at 5 mg/kg/day dose, and its inhibitory efficacy at 10 mg/kg/day is equivalent to 100 mg/kg/day of curcumin. Further, increasing the dose of 21a to 50 mg/kg/day reduced the tumor weight to 60% lighter than that of the control group.

Figure 2B:
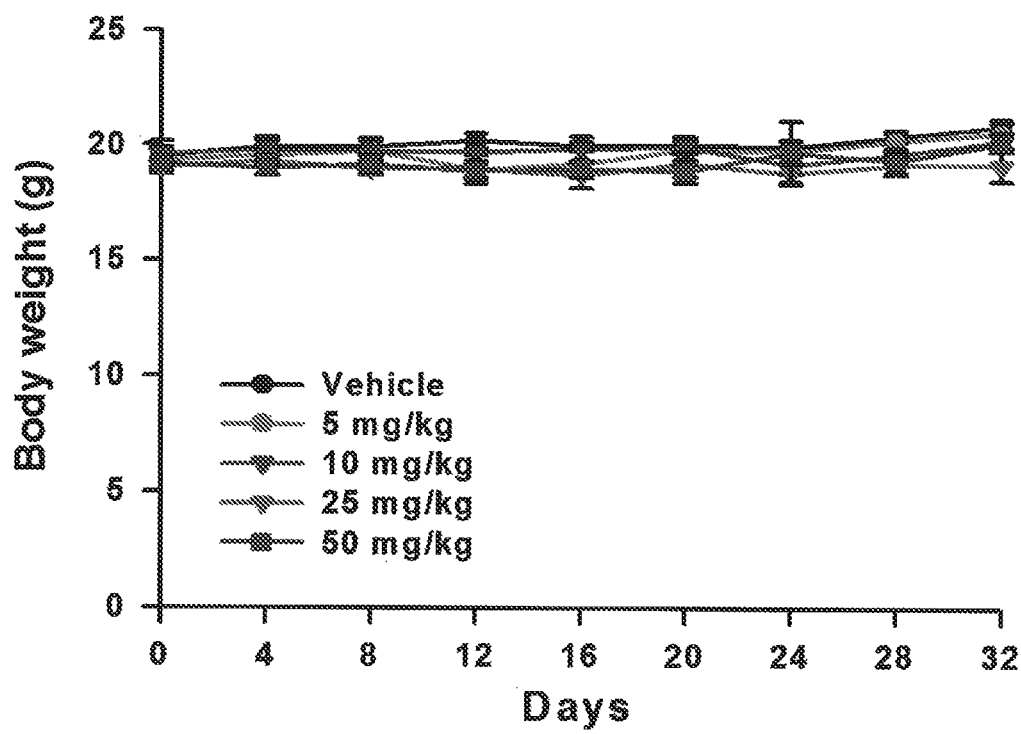

During the course of antitumor evaluation, no significant difference in body weight (FIG. 2B), behavior change and blood chemistry (serology detection) of tested mice were observed between the 21a-treated, curcumin-treated and untreated control group. The above findings suggested that 21a is an effective and low-toxicity drug candidate for treating TNBC.

1-5. In Vivo Antitumor Activity of 21a Combined with Doxorubicin

Figure 3A:
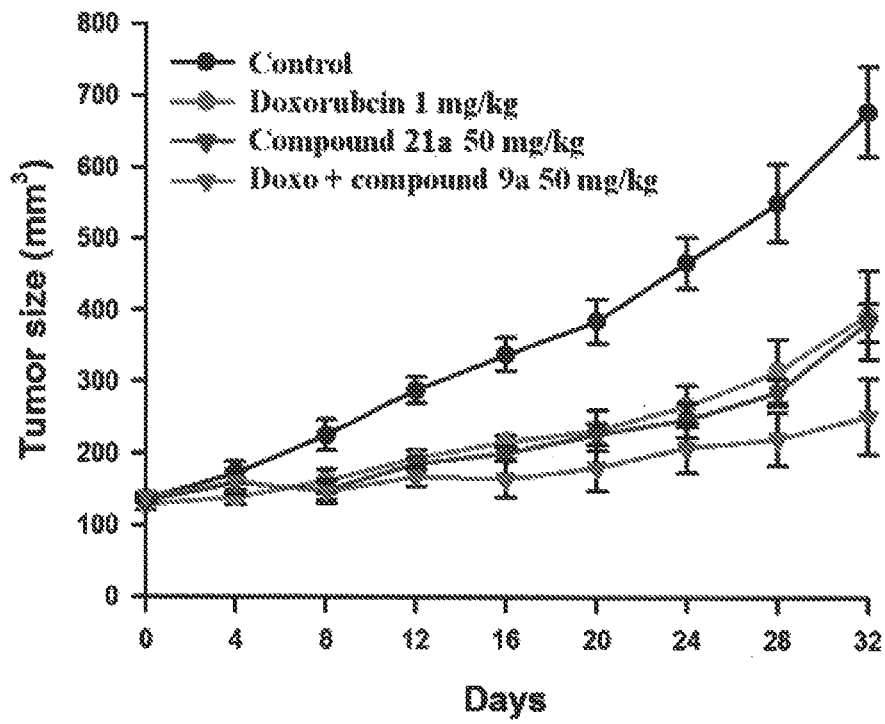
Figure 3B:
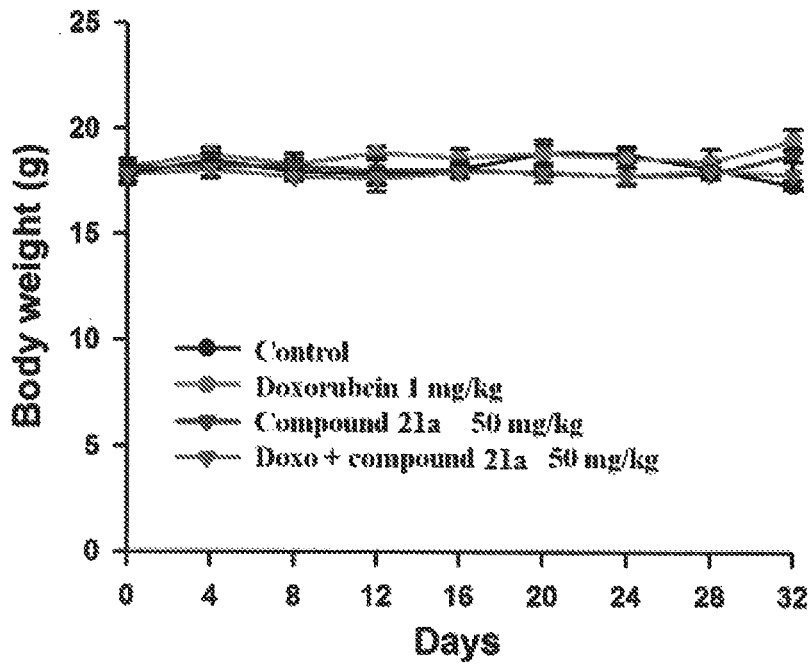

From the above in vitro test result of 21a, the synergistic effect of combining 21a with Doxorubicin was noticed against TNBC cell line. For comparison, the same 21a-Doxorubicin combination was also tested for antitumor activity on MDA-MB-231 Xenograft nude mice model, and the result was shown in FIGS. 3A, and 3B. The PO of 21a alone, or IP administration of 1 mg/kg/day of Doxorubicin alone reduced the weight of MDA-MB-231 tumor by 60% when compared with that of the control group. On the other hand, when the above dose of 21a was combined with that of Doxorubicin in the treatment, the tumor weight was reduced down to 80% smaller than that of the control group (FIG. 3A). During the course of antitumor evaluation, no significant difference in body weight (FIG. 3B), behavior change and blood chemistry (serology detection) of tested mice were observed between the treated and the untreated control groups.

Doxorubicin, if used alone, is a potent broad spectrum anticancer drug which is known to induce adverse effects such as cardiomyopathy, in particular, the cumulative dose related cardiomyopathy is likely to cause congestive heart failure.

The use of antioxidant to prevent cardiotoxicity of Doxorubicin has been considered[19]. In fact, it was reported that the Doxorubicin-antioxidant co-drug reduced the cardiotoxicity compared with Doxorubicin used alone[19].

Microarray analysis of compound 21a in vitro revealed that 21a significantly induced the expression of antioxidant gene HOMX-1 (heme oxygenase 1) in MDA-MB-231 cells (Table 3). Thus, compound 21a is considered as a potent antioxidant; its combined use with Doxorubicin is expected to reduce cardiotoxicity which is subjected to future study.

1-6. Preliminary Acute Toxicity of 21a and 35a

Normal mice were treated with 21a or 35a by oral route at 500 mg/kg/day for 5 consecutive days, following by 21 days of post-treatment observation. The result indicated that no significant difference was detectable in body weight and behavior change between the treated group and the untreated control group. This suggested that 21a and 35a are low-toxic drug candidates. Detailed data for their toxicology and safety pharmacology studies will be carried out in the near future.

Figure 4A:
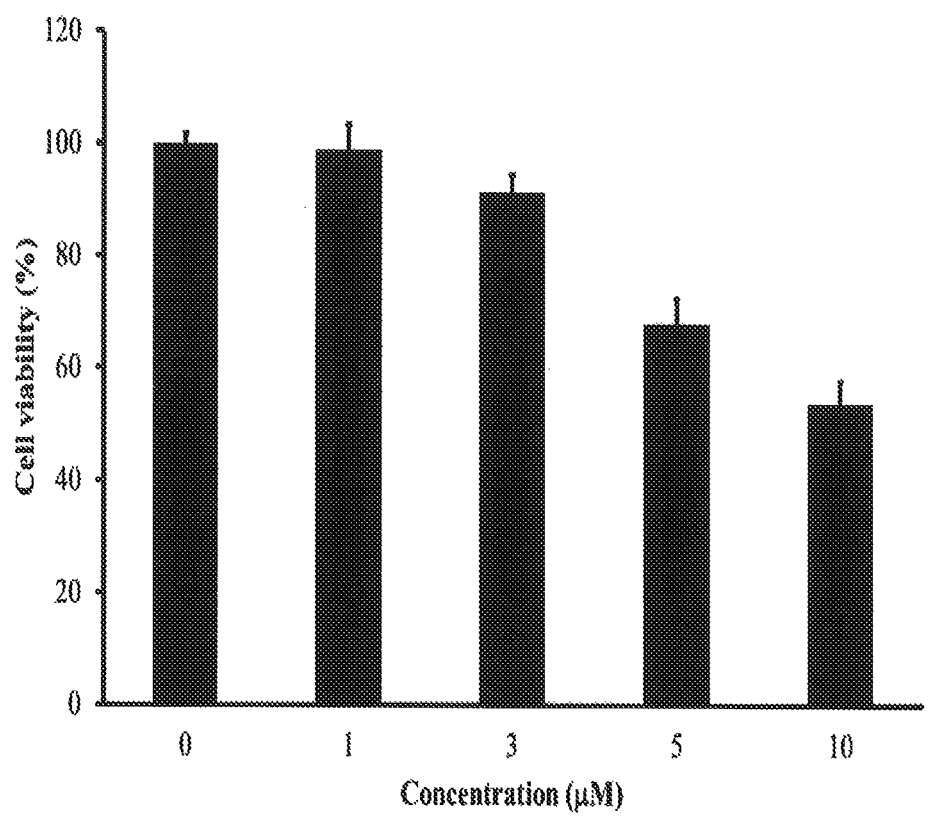
FIGS. 4A and 4B show that 21a affects cell viability and cell morphology in MDA-MB-231 cells, in FIG. 4A Cells were incubated with various concentrations (0, 1, 3, 5 and 10 μM) of 21a for 24 h and cell viability was determined using an MTT exclusion method, wherein the total number of viable cells was counted using MTT analysis as described in Materials and methods, and each data point is the means±SD of 3 experiments.
Figure 4B:
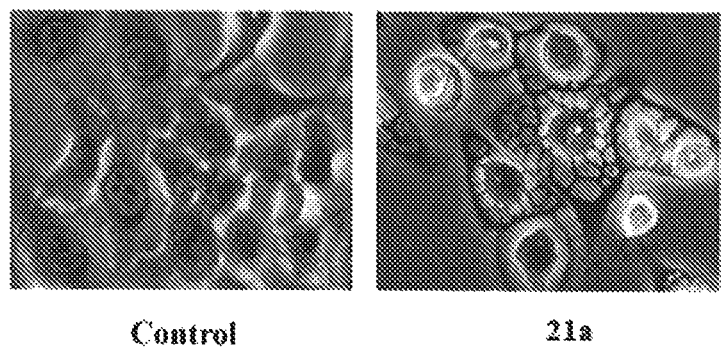

1.7 Anticancer Mechanism of 21a 1-7-1. 21a Inhibits Cell Proliferation of MDA-MB-231 Breast Cancer Cells At first, the effect of 21a on the viability of MDA-MB-231 breast cancer was first investigated using the MTT assay. 21a significantly reduced the viability of MDA-MB-231cells in a concentration-dependent manner (FIG. 4A). Morphological observation revealed that 21a treatment caused breast cancer cell apoptosis and autophagy with characteristics, including cytoplasmic membrane blebbing, cell shrinkage and autophagic vacuoles (FIG. 4B).

Figure 5A:
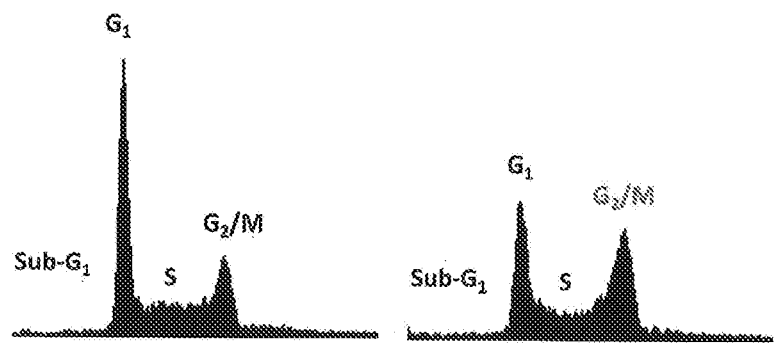
FIGS. 5A to 5C show 21a induces $G_2/M$ arrest of MDA-MB-231 cells.
Figure 5B:
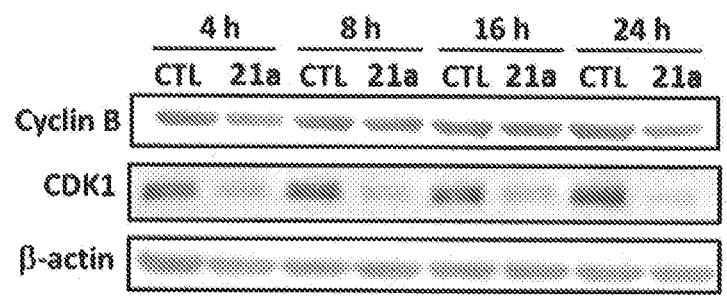
Figure 5C:
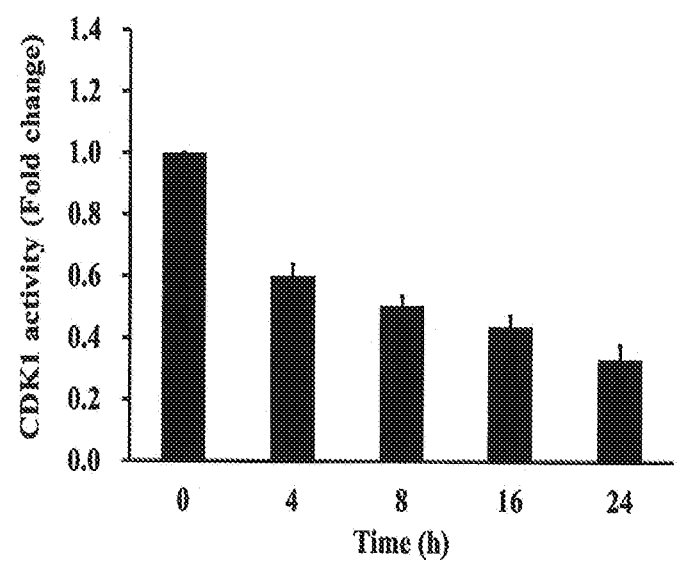

1-7-2. 21a Induced G2/M Arrest, Decreased CDK1 Activity and Apoptosis in MDA-MB-231 Cells To investigate the cell cycle distribution of 21a-treated MDA-MB-231 cells, cells were stained with propidium iodide (PI). As shown in FIG. 5A, flow cytometry showed that 21a treatment (5 lμM) of MDA-MB-231 cells significantly increased G2/M cell population at 24 h. The effects of 21a on G2/M phase-related proteins in MDA-MB-231 cells were investigated. Our results showed that 21a effectively down-regulated the levels of Cyclin B and CDK 1 (FIG. 5B). We examined the CDK1 activity in 21a-treated MDA-MB-231 cells. Results shown in FIG. 5C, 21a caused a significant decrease in CDK1 activity for 4-12 h of treatment. Our results suggest that down-regulate CDK1 activities play important roles in G2/M phase arrest in 21a-treated MDA-MB-231 cells.

1-7-3. 21a Induces Cell Apoptosis of MDA-MB-231 Breast Cancer Cells

Figure 6:
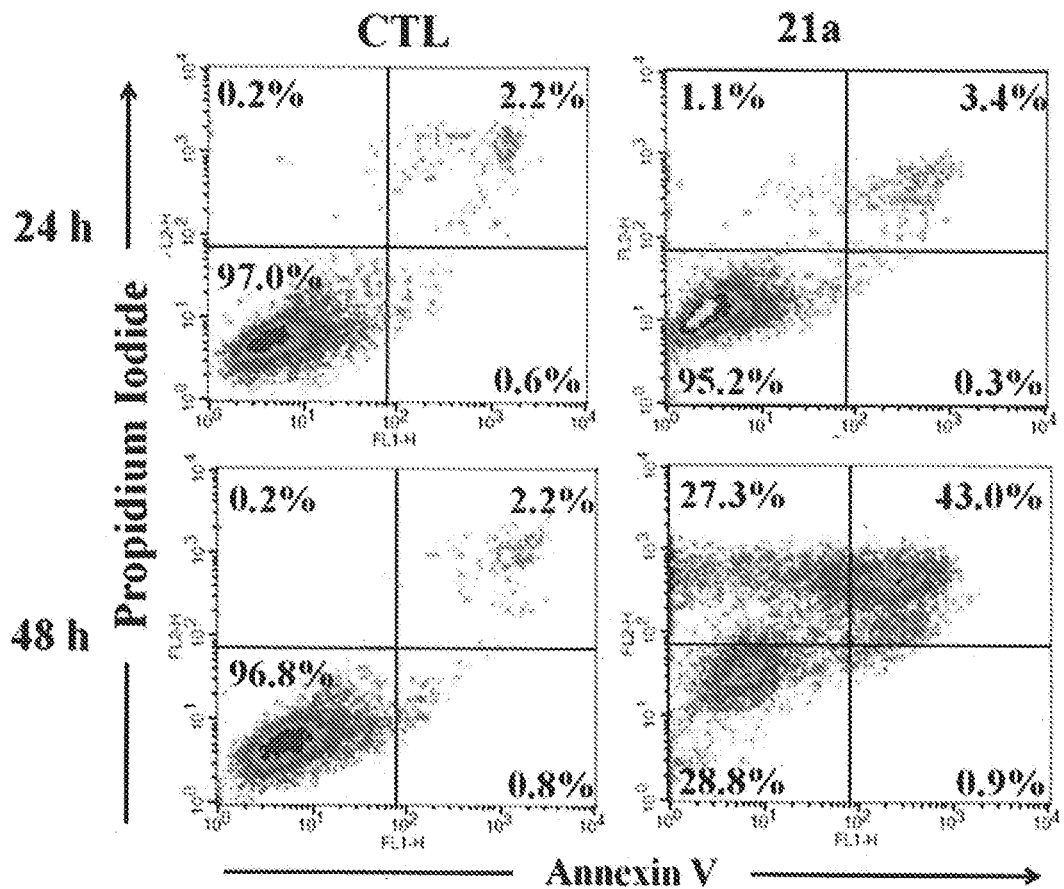
FIG. 6 shows 21a induces apoptosis of MDA-MB-231 cells, wherein MDA-MB-231 cells were treated with 5 μM of 21a for 24 and 48 h, and cells were collected and stained with annexin V/propidium iodide and analyzed with flow cytometry. The annexin V-positive cells were counted as the percentage of apoptotic cells.

To further confirm whether the inhibition of viability results from the induction of apoptosis, 21a-treated cells were detected with annexin V-propidium iodide double staining. Treatment with 21a for 24 and 48 h significantly increased the population of annexin V-positive MDA-MB-231 cell (FIG. 6), indicating that 21a induced apoptosis.

Figure 7A:
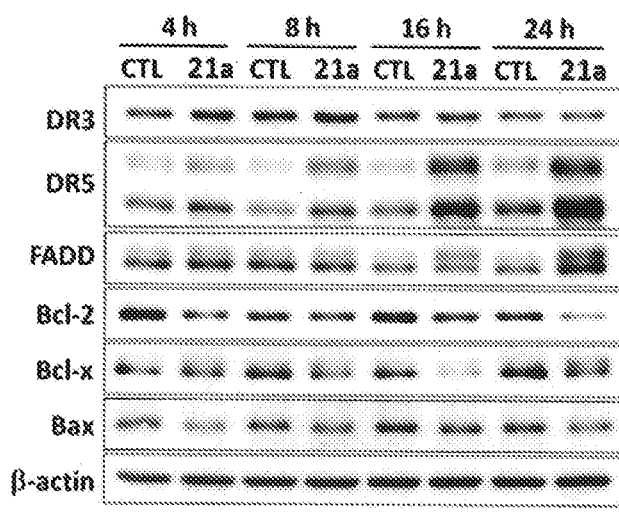
FIGS. 7A and 7B show 21a activates both death receptor-mediated, mitochondrial apoptosis pathways (7A) and ER stress apoptosis pathways (7B), wherein MDA-MB-231 cells were treated with the 10 μM of 21a for 0, 4, 8, 16 and 24 h, and cell lysates were collected for western blot analysis.
Figure 7B:
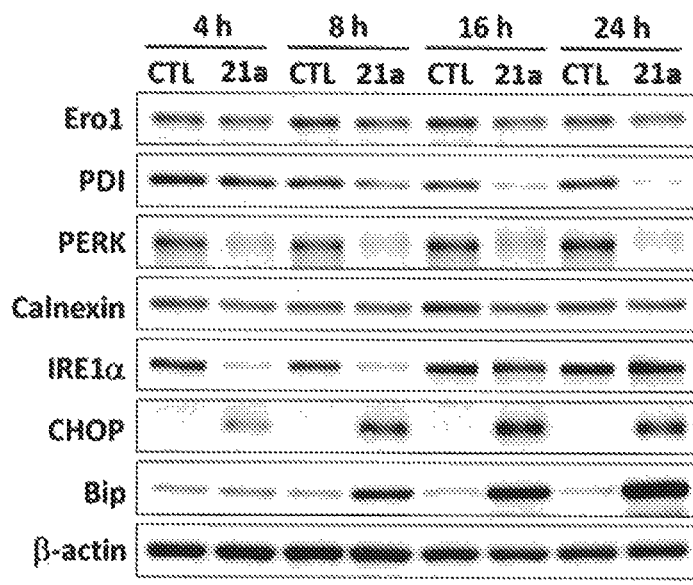

1-7-4. 21a Activates Both Death Receptor-Mediated, Mitochondrial and ER Stress Apoptotic Pathways The effects of 21a on apoptosis-related proteins in MDA-MB-231 cells were investigated. Our results showed that 21a effectively up-regulated the levels of DR5, FADD, Bax and downregulated the levels of Bcl-2, Bcl-x (FIG. 7A). On the other hand, our results also showed that 21a effectively up-regulated the levels of CHOP, Bip and downregulated the levels of Ero1, PD1, PERK1, Calnexin, IRE1α (FIG. 7B). These results suggested that 21a-induced apoptosis by modulating both death receptor-mediated, mitochondria-mediated and ER stress apoptotic pathways.

1-7-5. 21a Induces Cell Autophagy of MDA-MB-231 Breast Cancer Cells

Figure 8:
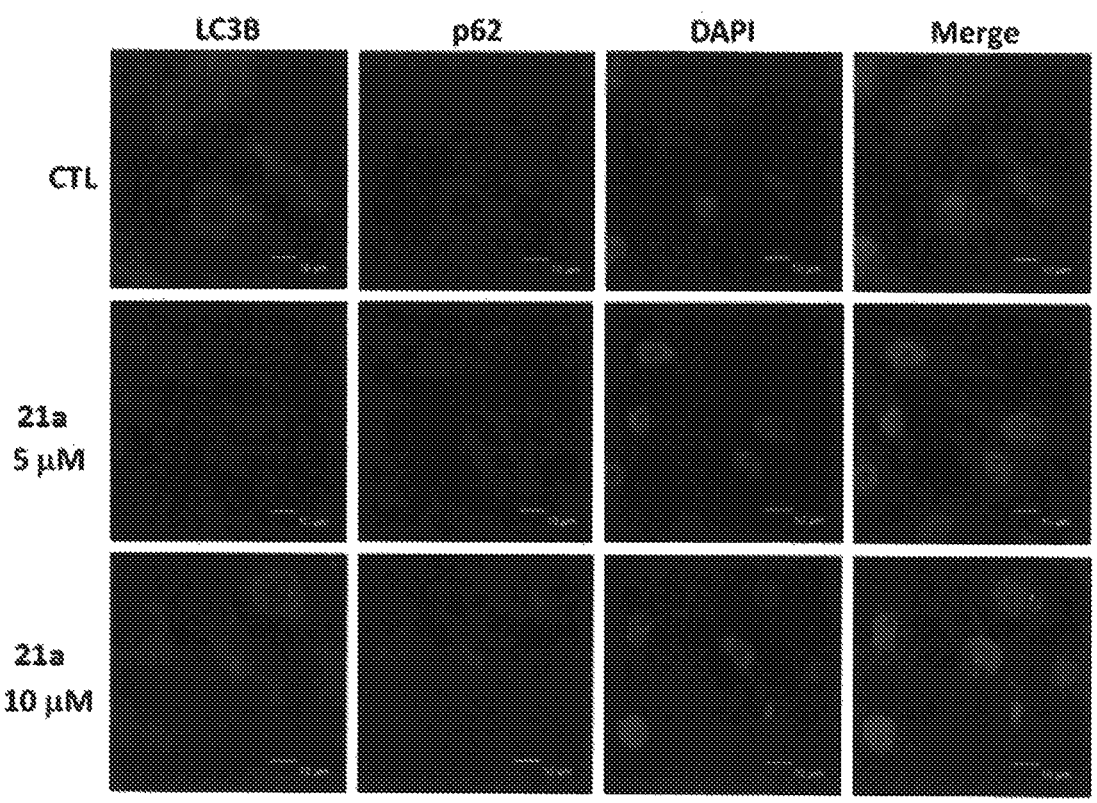
FIG. 8 show 21a induces LC3B and p62 expression of MDA-MB-231 cells, wherein MDA-MB-231 cells were treated with 5 and 10 μM of 21a for 24 h, and cells were collected and stained with LC3B-FITC antibody and p62-PE antibody and analyzed with confocal microscope.

To further confirm whether the inhibition of viability results from the induction of autophagy, 21a-treated cells were detected with LC3B and p62 double staining. Treatment with 21a for 5 µM and 10 µM significantly increased the LC3B-positive and p62-positive MDA-MB-231 cell (FIG. 8), indicating that 21a induced autophagy.

1-7-6. Effects of 21a on Levels of Proteins Associated with Autophagy

Figure 9:
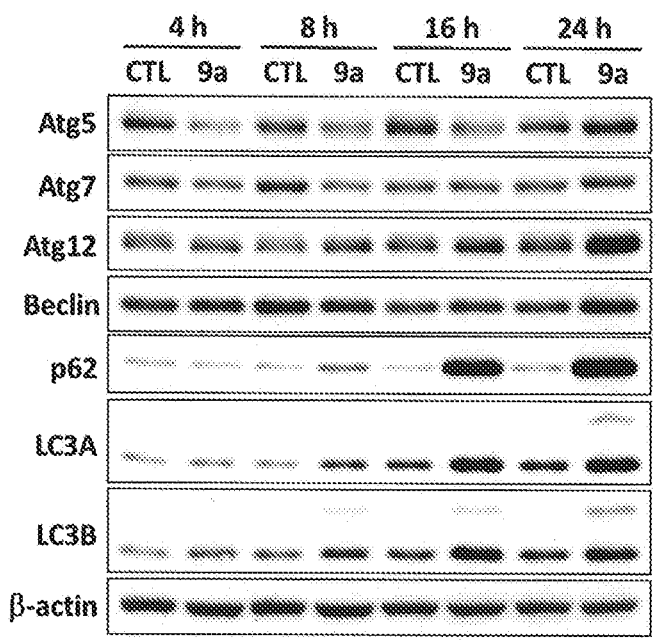
FIG. 9 shows effects of 21a caused protein level change on autophagy in MDA-MB-231 cells, wherein MDA-MB-231 cells were treated with the 10 μM of 21a for 4, 8, 16 and 24 h, and cell lysates were collected for western blot analysis.

Results are presented in FIG. 9, 21a treatment induced the levels of Atg5, Atg7, Atg12, Beclin, p62 and LC3B in a time-dependent manner. These data demonstrated that 21a induced autophagy by activating Atg family proteins in MDA-MB-231 cells.

1-7-7. cDNA Microarray Analysis for 21a-Induced Cell Death in MDA-MB-231 Cells

Figure 10:
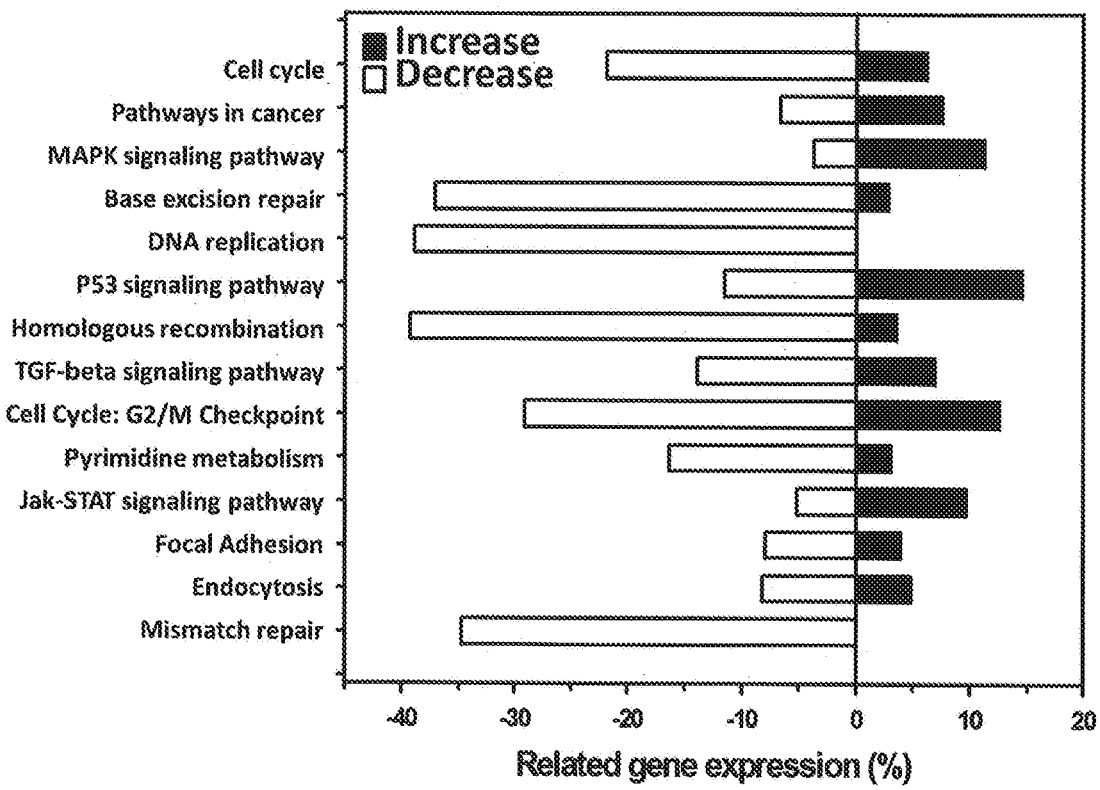
FIG. 10 shows the possible canonical pathways from MDA-MB-231 cells after exposure to 21a by cDNA microarray. The cells were treated with 10 μM of 21a, and then were harvest and total RNA was extracted for cDNA microarray assay. The changes in gene expression scored by the number of pathways from GeneGo analysis.

After treatment with 21a, cells were harvested for isolating total RNA and then cDNA microarray analysis was performed. The cDNA microarray analysis showed that 97 genes (69 genes, up-regulated; 28 genes, down-regulated) were expressed at least by 2.5 folds compared with the untreated control cells (Table 3). The top alteration in gene expression scored by the number of pathway networks from GeneGo analysis program can be seen in FIG. 10. These genes may also be involved in cell death and cytotoxic responses in 21a-treated MDA-MB-231 cells.

Figure 11:
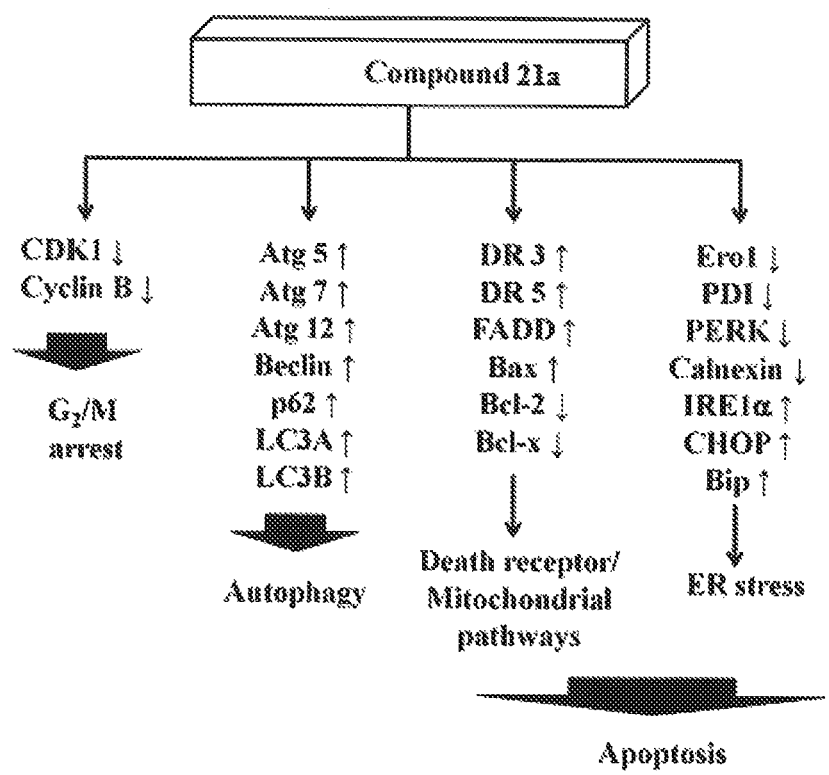
FIG. 11 shows the proposed model showing that the 21a induces G2/M phase arrest, autophagy and apoptotic cell death in human breast cancer MDA-MB-231 cells.

To sum up, the molecular signaling pathways are summarized in FIG. 11. This invention is the first report to provide an approach regarding that the newly curcumin derivative 21a tends to inhibit human breast MDA-MB-231 cells. We presented our novel findings and the efficacy of 21a might be sufficient to investigate the potential of breast cancer treatment in the future.

TABLE 3

Genes change more than 2.5-fold changes in mRNA levels in MDA-MB-231 cells following a 24-h treatment with 21a as identified using DNA microarray

| ID | log2 (Ratio) | Gene_symbol | Description |
| --- | --- | --- | --- |
| PH_hs_0049600 | 6.643856 | HSPA6 | heat shock 70 kDa protein 6 (HSP70B') |
| PH_hs_0006387 | 6.274261 | ZFAND2A | zinc finger, AN1-type domain 2A |
| PH_hs_0004421 | 5.381376 | PPP1R15A | protein phosphatase 1, regulatory subunit 15A |
| PH_hs_0000305 | 4.941673 | MMP10 | matrix metallopeptidase 10 (stromelysin 2) |
| PH_hs_0046245 | 4.763129 | RN7SK | RNA, 7SK small nuclear |
| PH_hs_0000076 | 4.587356 | IL12A | interleukin 12A |
| PH_hs_0027902 | 4.286664 | ABL2 | v-abl Abelson murine leukemia viral oncogene homolog 2 |
| PH_hs_0010276 | 4.189167 | DUSP1 | dual specificity phosphatase 1 |
| PH_hs_0031719 | 4.146525 | CCL26 | chemokine (C—C motif) ligand 26 |
| PH_hs_0000156 | 4.093858 | DUSP2 | dual specificity phosphatase 2 |
| PH_hs_0011943 | 4.063702 | HMOX1 | heme oxygenase (decycling) 1 |
| PH_hs_0045501 | 4.039442 | EID3 | EP300 interacting inhibitor of differentiation 3 |
| PH_hs_0004561 | 3.997336 | GEM | GTP binding protein overexpressed in skeletal muscle |
| PH_hs_0042334 | 3.931415 | MT4 | metallothionein 4 |
| PH_hs_0048553 | 3.866096 | MYCT1 | myc target 1 |
| PH_hs_0000684 | 3.853854 | DNAJB9 | DnaJ (Hsp40) homolog, subfamily B, member 9 |
| PH_hs_0035404 | 3.763571 | SAT1 | spermidine/spermine N1-acetyltransferase 1 |
| PH_hs_0000057 | 3.698185 | ATF3 | activating transcription factor 3 |
| PH_hs_0025319 | 3.562429 | C3orf52 | chromosome 3 open reading frame 52 |
| PH_hs_0033101 | 3.555868 | DDIT3 | DNA-damage-inducible transcript 3 (CHOP) |
| PH_hs_0002700 | 3.513438 | OSGEN1 | oxidative stress induced growth inhibitor 1 |
| PH_hs_0037472 | 3.480422 | MALAT1 | metastasis associated lung adenocarcinoma transcript 1 |
| PH_hs_0035765 | 3.427173 | GDF15 | growth differentiation factor 15 |
| PH_hs_0002492 | 3.366024 | SAT1 | spermidine/spermine N1-acetyltransferase 1 |
| PH_hs_0062199 | 3.356707 | AKR1C1\|LOC101060798 | aldo-keto reductase family 1, member C1\|aldo-keto reductase family 1 member C2-like |
| PH_hs_0000852 | 3.324182 | SESN2 | sestrin 2 |
| PH_hs_0023008 | 3.242113 | FRS2 | fibroblast growth factor receptor substrate 2 |
| PH_hs_0004751 | 3.219326 | MMP1 | matrix metallopeptidase 1 (interstitial collagenase) |
| PH_hs_0031143 | 3.213328 | VIMP | VCP-interacting membrane protein |
| PH_hs_0025525 | 3.198476 | CLU | clusterin |
| PH_hs_0024315 | 3.075314 | DNAJB4 | DnaJ (Hsp40) homolog, subfamily B, member 4 |
| PH_hs_0035614 | 3.062771 | RC3H1 | ring finger and CCCH-type domains 1 |
| PH_hs_0027152 | 3.037995 | RMND5A | required for meiotic nuclear division 5 homolog A (S. cerevisiae) |
| PH_hs_0021974 | 3.010862 | DNAJC3 | Dna (Hsp40) homolog, subfamily C, member 3 |
| PH_hs_p061784 | 2.967357 | CDKN1A | cyclin-dependent kinase inhibitor 1A (p21, Cip1) |
| PH_hs_0035466 | 2.962064 | AKR1C3\|AKR1C1 | aldo-keto reductase family 1, member C3\|aldo-keto reductase family 1, member C1 |
| PH_hs_0027162 | 2.960759 | SLC3A2 | solute carrier family 3 (activators of dibasic and neutral amino acid transport), member 2 |
| PH_hs_0022919 | 2.960552 | CLCF1 | cardiotrophin-like cytokine factor |
| PH_hs_0000255 | 2.916655 | SRGN | serglycin |
| PH_hs_0024155 | 2.904033 | CDKN1A | cyclin-dependent kinase inhibitor 1A (p21, Cip1) |
| PH_hs_0043719 | 2.894684 | HMGCS1 | 3-hydroxy-3-methylglutaryl-CoA synthase 1 (soluble) |
| PH_hs_0045838 | 2.838192 | SLC6A6 | solute carrier family 6 (neurotransmitter transporter, taurine) member 6 |
| PH_hs_0014155 | 2.836392 | HSPA1B | heat shock 70 kDa protein 1B |
| PH_hs_0044272 | 2.829317 | CLK1 | CDC-like kinase 1 |
| PH_hs_0048881 | 2.809371 | FKBP4 | FK506 binding protein 4, 59 kDa |
| PH_hs_0020147 | 2.803912 | CLK1 | CDC-like kinase 1 |
| PH_hs_0028987 | 2.768552 | TCF21 | transcription factor 21 |
| PH_hs_0042409 | 2.76703 | DNAJB1 | DnaJ (Hsp40) homolog, subfamily B, member 1 |
| PH_hs_0001262 | 2.748306 | SENP5 | SUMO1/sentrin specific peptidase 5 |
| PH_hs_0060828 | 2.734692 | TRIB3 | tribbles homolog 3 (Drosophila) |
| PH_hs_0023556 | 2.733421 | C21orf91 | chromosome 21 open reading frame 91 |
| PH_hs_0061012 | 2.731293 | ZBTB21 | zinc finger and BTB domain containing 21 |

TABLE 3-continued

Genes change more than 2.5-fold changes in mRNA levels in MDA-MB-231 cells following a 24-h treatment with 21a as identified using DNA microarray

| ID | log2 (Ratio) | Gene_symbol | Description |
|---|---|---|---|
| PH_hs_0029660 | 2.695316 | AKR1C1 | aldo-keto reductase family 1, member C1\|aldo-keto reductase family 1 |
| PH_hs_0037242 | 2.683231 | MALAT1 | metastasis associated lung adenocarcinoma transcript 1 (non-protein coding) |
| PH_hs_0002812 | 2.667718 | C18orf25 | chromosome 18 open reading frame 25 |
| PH_hs_0027209 | 2.665362 | GADD45B | growth arrest and DNA-damage-inducible, beta |
| PH_hs_0002971 | 2.664712 | ZNF77 | zinc finger protein 77 |
| PH_hs_0003180 | 2.646292 | SMIM13 | small integral membrane protein 13 |
| PH_hs_0000694 | 2.625719 | RND3 | Rho family GTPase 3 |
| PH_hs_0023711 | 2.599232 | HSPA5 | heat shock 70 kDa protein 5 |
| PH_hs_0023894 | 2.583817 | TRIB3 | tribbles homolog 3 (*Drosophila*) |
| PH_hs_0060053 | 2.574976 | ZNF121 | zinc finger protein 121 |
| PH_hs_0014119 | 2.571605 | BRF2 | BRF2, subunit of RNA polymerase III transcription initiation factor, BRF1-like |
| PH_hs_0033027 | 2.547837 | SIK1 | salt-inducible kinase 1 |
| PH_hs_0024236 | 2.547678 | ATP2A2 | ATPase, Ca++ transporting, cardiac muscle, slow twitch 2 |
| PH_hs_0042225 | 2.541029 | DUSP5 | dual specificity phosphatase 5 |
| PH_hs_0044921 | 2.534876 | HSPA1A | heat shock 70 kDa protein 1A |
| PH_hs_0000566 | 2.528881 | SLC25A25 | solute carrier family 25, member 25 |
| PH_hs_0030976 | 2.516291 | NFKBIB | nuclear factor of kappa light polypeptide gene enhancer in B-cells inhibitor, beta |
| PH_hs_0014995 | −3.653241 | METTL7A | methyltransferase like 7A |
| PH_hs_0023845 | −3.269308 | BBS2 | Bardet-Biedl syndrome 2 |
| PH_hs_0009437 | −3.05235 | TOP2A | topoisomerase (DNA) II alpha 170 kDa |
| PH_hs_0047352 | −3.043277 | MARCKS | myristoylated alanine-rich protein kinase C substrate |
| PH_hs_0047965 | −2.959225 | PHLDA1 | pleckstrin homology-like domain, family A, member 1 |
| PH_hs_0040619 | −2.891495 | MXD3 | MAX dimerization protein 3 |
| PH_hs_0012629 | −2.890238 | H1F0 | H1 histone family, member 0 |
| PH_hs_0004988 | −2.878231 | LMNB1 | lamin B1 |
| PH_hs_0035609 | −2.788184 | ETV1 | ets variant 1 |
| PH_hs_0049449 | −2.729758 | GPR39 | G protein-coupled receptor 39 |
| PH_hs_0027843 | −2.724437 | FAM20C | family with sequence similarity 20, member C |
| PH_hs_0027863 | −2.718276 | LRRC45 | leucine rich repeat containing 45 |
| PH_hs_0007383 | −2.717289 | F2R | coagulation factor II (thrombin) receptor |
| PH_hs_0036878 | −2.71449 | PIF1 | PIF1 5'-to-3' DNA helicase homolog (*S. cerevisiae*) |
| PH_hs_0047697 | −2.688182 | ARF6 | ADP-ribosylation factor 6 |
| PH_hs_0048993 | −2.677322 | NRP1 | neuropilin 1 |
| PH_hs_0031540 | −2.66121 | GNG2 | guanine nucleotide binding protein (G protein), gamma 2 |
| PH_hs_0010634 | −2.659899 | TXNIP\|LOC101060503 | thioredoxin interacting protein\|thioredoxin-interacting protein-like |
| PH_hs_0028915 | −2.621805 | CCDC85B | coiled-coil domain containing 85B |
| PH_hs_0000866 | −2.612763 | OMA1 | OMA1 zinc metallopeptidase homolog (*S. cerevisiae*) |
| PH_hs_0030800 | −2.552826 | FANCF | Fanconi anemia, complementation group F |
| PH_hs_0025966 | −2.55207 | CTDSP1 | CTD small phosphatase 1 |
| PH_hs_0023862 | −2.551096 | CBY1 | chibby homolog 1 (*Drosophila*) |
| PH_hs_0047571 | −2.546813 | PDP1 | pyruvate dehydrogenase phosphatase catalytic subunit 1 |
| PH_hs_0028200 | −2.537288 | CENPI | centromere protein I |
| PH_hs_0003147 | −2.533627 | PDGFC | platelet derived growth factor C |
| PH_hs_0035337 | −2.514458 | OMA1 | OMA1 zinc metallopeptidase homolog (*S. cerevisiae*) |
| PH_hs_0038982 | −2.502536 | LOC100134259 | uncharacterized LOC100134259 |

2. Conclusion

A series of novel bis(hydroxymethyl) alkanoate analogs of curcuminoids were designed, synthesized and screened for anticancer activity. The screening results indicate that these analogs exhibit more potent anticancer activity than curcumin. Among these new analogs, compound 21a was selected for further evaluation. The results of in vitro tests indicate that compound 21a has 3.4-7.4 times greater inhibitory activity than curcumin against TNBC cells which were not predictable in advance. Besides, 21a also demonstrates significant inhibitory activity toward Doxorubicin-resistant MDA-MB-231 cells, showing 10 times the potency of curcumin.

Synergistic anticancer effect is observed when compound 21a was used in combination with Doxorubicin in treating MDA-MB-231 cells. When compound 21a was evaluated against the MDA-MB-231 Xenograft nude mice model, it was found that its antitumor activity is 10 fold more potent than curcumin. The combined use of compound 21a with Doxorubicin enhance the antitumor activity of Doxorubicin. Attributable to its low toxicity and significant antitumor activity, compound 21a has the potential to be developed into safe clinical drug for TNBC treatment.

3. Experimental Section

3-1. Chemistry

The reactions were performed under an atmosphere of air unless otherwise stated. All solvents and reagents were employed as received. Analytical thin layer chromatography was performed on $SiO_2$ 60 F-254 plates and flash column chromatography was carried out using $SiO_2$ 60 (particle size 0.040-0.055 mm, 230-400 mesh), both of which are available from E. Merck. Visualization was performed under UV irradiation at 254 nm followed by staining with aqueous potassium permanganate ($KMnO_4$ (3 g) and $K_2CO_3$ (20 g)) in 300 mL of $H_2O$ containing 5 mL of an aqueous solution of NaOH (5%, w/v)) and charring by heat gun. Fourier transform infrared spectra (IR) were recorded on Shimadzu spectrum IRPrestige-21 system and expressed in $cm^{-1}$. $^1H$, $^{19}F$ and $^{13}C$ NMR spectra were recorded on Bruker 500 FT NMR. Chloroform-d and Methanol-d were used as the solvent and TMS (δ=0.00 ppm) as an internal standard. Chemical shifts are reported as δ values in ppm as referenced to TMS. Multiplicities are recorded as s (singlet), d (doublet), t (triplet), q (quartet), quint (quintet), sext (sextet), sept (septet), dd (doublet of doublets), dt (doublet of triplets), br (broad), m (multiplet). Coupling constants (J) are expressed in Hz. HRMS were measured by JEOL JMS-HX110 spectrometer and spectral data were recorded as m/z values. Melting points were measured using an Electrothermal instrument.

General Procedure for the Synthesis of Compound 7a and 7b

The general procedure is illustrated immediately below with compound 1 as a specific example.

2,2,5-trimethyl-1,3-dioxane-5-carboxylic acid (7a)

In a two-neck round bottle, 1,3 dihydroxy 2-methyl 2-propionic acid (5.00 g, 37.2 mmol), p-TSA (33 mg, 0.19 mmol) and toluene (30 mL) were stirred under reflux for 10 min. Subsequently, dimethoxy propane (8.00 g, 76.8 mmol) diluted with toluene (10 mL) was added dropwise under Dean Stark and continuous removal and addition of toluene (20 mL) for 2 h. After that, the reaction mixture was cooled to room temperate and cure product was obtained as gray solid. The crude product was washed with toluene and hexane to afford pure compound 7a as white solid (5.84 g, 90% yield). mp=104-106° C.; $^1$H NMR (500 MHz, CD$_3$OD) δ 4.21 (d, J=12.0 Hz, 2H), 3.71 (d, J=12.0 Hz, 2H), 1.48 (s, 3H), 1.46 (s, 3H), 1.24 (s, 3H); $^{13}$C NMR (CD$_3$OD, 125 MHz): δ 176.4, 97.9, 65.7, 64.4, 24.1, 21.1, 17.5; HRMS [ESI]$^+$ calculated for C$_8$H$_{14}$O$_4$: 197.0790 [M+Na]$^+$; found: 197.0792.

5-ethyl-2,2-dimethyl-1,3-dioane-5-carboxylic add (7b)

Yield: 88%; mp=114-115° C.; $^1$H NMR (500 MHz, CD$_3$OD) δ 4.17 (d, J=12.0 Hz, 2H) 3.74 (d, J=12.0 Hz, 2H), 1.63 (q, J=7.5 Hz, 2H), 1.42 (s, 3H) 1.36 (s, 3H), 0.88 (t, J=7.5 Hz, 3H); $^{13}$C NMR (CD$_3$OD, 125 MHz): δ 175.5, 98.1, 64.4, 25.0, 24.1, 21.1, 7.1; HRMS [ESI]$^+$ calculated for C$_9$H$_{16}$O$_4$: 211.0946 [M+Na]$^+$; found: 211.0944.

General Procedure for the Synthesis of Compound 8a-17

The general procedure is illustrated immediately below with compound 8a and 8b as a specific example.

((1E,3Z,6E)-3-Hydroxy-5-oxohepta-1,3,6-triene-1,7-diyl)bis(2-methoxy-4,1-phenylene) bis(2,2,5-trimethyl-1,3-dioxane-5-carboxylate) (8a) and 4-((1E,4Z,6E)-5-hydroxy-7-(4-hydroxy-3-methoxyphenyl)-3-oxohept-1,4,6-trien-1-yl)-2-methoxyphenyl 2,2,5-trimethyl-1,3-dioxane-5-carboxylate (8b)

To a stirred solution of curcumin (3.50 g, 9.50 mmol) in DMF (90 mL) were added sequentially EDCI (4.42 g, 28.5 mmol), HOBt (0.26 g, 1.90 mmol), compound 7a (4.96 g, 28.5 mmol) and DMAP (0.24 g, 1.90 mmol) at room temperature. The reaction mixture was stirred at the same temperature for 16 h and then H$_2$O (110 mL) was added to quench the reaction. The aqueous layer was separated and extracted with EtOAc (3×70 mL). The combined organic extracts were washed with brine, dried over MgSO$_4$, filtered and concentrated to give the crude product, which was then purified by flash chromatography on silica gel with EtOAc/n-hexane/CH$_2$Cl$_2$ (1:1:1) to afford 8a (4.20 g, 65% yield) and 8b (0.99 g, 20% yield) as orange solids.

(8a) mp=64-66° C.; $^1$H NMR (CDCl$_3$, 500 MHz): δ 7.65 (dd, J=15.5, 3.0 Hz, 2H), 7.20-7.18 (m, 2H), 7.15-7.14 (m, 2H), 7.18-7.10 (m, 2H), 6.59 (d, J=15.5, 3.5 Hz, 2H), 5.89 (s, 1H), 4.37 (d, J=11.5 Hz, 4H), 3.89 (s, 6H), 3.79 (d, J=11.5 Hz, 4H), 1.49-1.47 (m, 12H), 1.37 (s, 6H); $^{13}$C NMR (CDCl$_3$, 125 MHz): δ 183.1, 172.2, 151.3, 141.3, 139.9, 134.0, 124.3, 123.2, 121.0, 111.5, 101.7, 98.2, 77.5, 66.0, 65.9, 55.9, 42.3, 24.0, 23.3, 18.7; HRMS [ESI]$^+$ calculated for C$_{37}$H$_{44}$O$_{12}$; 703.2730 [M+Na]$^+$; found: 703.2727.

(8b) mp=69-71° C.; $^1$H NMR (CDCl$_3$, 500 MHz): δ 7.61 (dd, J=15.0, 5.0 Hz, 2H), 7.18-7.11 (m, 5H), 6.95 (d, J=8.0 Hz, 1H), 6.54 (dd, J=29.0, 16.0 Hz, 2H), 5.85 (s, 1H), 4.38 (d, J=12.0 Hz, 2H), 3.96 (s, 3H), 3.88 (s, 3H), 3.79 (d, J=11.5 Hz, 2H), 1.50 (s, 3H), 1.49 (s, 3H), 1.43 (s, 3H); $^{13}$C NMR (CDCl$_3$, 125 MHz): δ 184.5, 181.8, 172.3, 151.3, 148.0, 146.8, 141.7, 139.4, 134.1, 127.5, 124.2, 123.2, 123.0, 121.7, 120.9, 114.9, 111.4, 109.7, 101.5, 98.2, 65.9, 55.9, 42.3, 24.1, 23.2, 18.7; HRMS [ESI]$^+$ calculated for C$_{29}$H$_{32}$O$_9$: 547.1944 [M+Na]$^+$; found: 547.1950.

((1E,3Z,6E)-3-Hydroxy-oxohepta-1,3,6-triene-1,7-diyl)bis(2-methoxy-4,1-phenylene) bis(5-ethyl-2,2-dimethyl-1,3-dioxane-5-carboxylate) (9a)

Yield=60%; mp=70-72° C.; $^1$H NMR (CDCl$_3$, 500 MHz): δ 7.64 (d, J=16.0 Hz, 2H), 7.19-7.13 (m, 4H), 7.08 (d, J=8.0 Hz, 2H), 6.59 (d, J=16.0 Hz, 2H), 5.89 (s, 1H), 4.35 (d, J=11.5 Hz, 4H), 3.88 (s, 6H), 3.86 (d, J=12.0 Hz, 4H), 1.89 (q, J=8.0 Hz, 4H), 1.48 (s, 12H), 1.04 (t, J=8.0 Hz, 6H); $^3$C NMR (CDCl$_3$, 125 MHz): δ 183.1, 171.4, 151.4, 141.3, 139.9, 134.0, 129.2, 124.3, 123.3, 122.2, 121.0, 111.5, 101.8, 98.4, 64.7, 64.6, 55.8, 46.3, 25.5, 24.2, 23.1, 8.1; HRMS [ESI]$^+$ calculated for C$_{39}$H$_{48}$O$_{12}$: 731.3043 [M+Na]$^+$; found: 731.3040.

4-((1E,4Z,6E)-5-Hydroxy-7-(4-hydroxy-3-methoxyphenyl)-3-oxohepta-1,4,6-trien-1-yl)-2-methoxyphenyl 5-ethyl-2,2-dimethyl-1,3-dioxane-5-carboxylate (9b)

Yield=22%; mp=68-70° C.; $^1$H NMR (CDCl$_3$, 500 MHz): δ 7.63 (dd, J=15.5, 3.5 Hz, 2H), 7.19-7.13 (m, 3H), 7.08-7.06 (m, 2H), 6.96 (d, J=8.0 Hz, 1H), 6.55 (d, J=30.3, 15.5 Hz, 2H), 5.85 (s, 1H), 4.35 (d, J=12.0 Hz, 2H), 3.97 (s, 3H), 3.89 (s, 3H), 3.86 (d, J=12.0 Hz, 2H), 1.89 (q, J=8.0 Hz, 2H), 1.49 (s, 6H), 1.05 (t, J=8.0 Hz, 3H); $^{13}$C NMR (CDCl$_3$, 125 MHz): δ 184.5, 181.8, 171.4, 151.4, 148.0, 146.8, 141.1, 139.4, 134.1, 127.5, 1242, 123.3, 123.0, 121.8, 120.9, 114.8, 111.4, 109.6, 101.5, 98.4, 64.6, 55.9, 55.8, 46.3, 25.5, 24.2, 23.1, 8.1; HRMS [ESI]$^+$ calculated for C$_{30}$H$_{34}$O$_9$: 539.2281 [M+H]$^+$; found: 539.2280.

((1E,3Z,6E)-3-hydroxy-5-oxohepta-1,3,6-trien-1,7-diyl)bis(4,1-phenylene) bis(2,2,5-trimethyl-1,3-dioxane-5-carboxylate) (10a)

Yield=55%; mp=58-60° C.; $^1$H NMR (CDCl$_3$, 500 MHz): δ 7.64 (d, J=15.5 Hz, 2H), 7.59 (d, J=8.0 Hz, 4H), 7.15 (d, J=8.0 Hz, 4H), 6.59 (d, J=15.5 Hz, 2H), 5.85 (s, 1H), 4.34 (d, J=12.0 Hz, 4H), 3.78 (d, J=12.0 Hz, 4H), 1.49 (s, 6H), 1.46 (s, 6H), 1.34 (s, 6H); $^{13}$C NMR (CDCl$_3$, 125 MHz): δ 183.1, 172.7, 152.0, 139.5, 132.8, 129.2, 124.2, 122.0, 108.3, 101.9, 98.3, 66.0, 52.1, 42.7, 25.4, 21.9, 18.4; HRMS [ESI]$^+$ calculated for C$_{35}$H$_{40}$O$_{10}$: 621.2700 [M+H]$^+$; found: 621.2699.

4-((1E,3Z,6E)-3-hydroxy-7-(4-hydroxyphenyl)-5-oxohepta-1,3,6-trien-1-yl)phenyl 2,2,5-trimethyl-1,3-dioxane-5-carboxylate (10b)

Yield=27%; mp=118-120° C.; $^1$H NMR (CDCl$_3$, 500 MHz): δ 7.65 (d, J=15.5 Hz, 2H), 7.59 (d, J=8.5 Hz, 2H), 7.48 (d, J=8.5 Hz, 2H), 7.16 (d, J=8.5 Hz, 2H), 6.86 (d, J=8.0 Hz, 2H), 6.56 (dd, J=33.7, 16.0 Hz, 2H), 5.83 (s, 1H), 4.36 (d, J=11.5 Hz, 2H), 3.80 (d, J=12.0 Hz, 2H), 1.51 (s, 3H), 1.48 (s, 3H), 1.37 (s, 3H); $^{13}$C NMR (CDCl$_3$, 125 MHz): δ 184.5, 181.9, 172.8, 157.6, 151.8, 140.6, 139.0, 132.9, 130.0, 129.1, 127.8, 124.2, 122.0, 121.8, 115.9, 101.6, 98.3, 66.0, 42.4, 25.4, 21.9, 18.1; HRMS [ESI]$^+$ calculated for C$_{27}$H$_{28}$O$_7$: 465.1913 [M+H]$^+$; found: 465.1917.

((1E,3Z,6E)-3-Hydroxy-5-oxohepta-1,3,6-triene-1,7-diyl)bis(2-methoxy-5,1-phenylene) bis(2,2,5-trimethyl-1,3-dioxane-5-carboxylate) (11a)

Yield=33%; mp=71-73° C.; $^1$H NMR (CDCl$_3$, 500 MHz): δ 7.60 (d, J=15.5 Hz, 2H), 7.40 (dd, J=8.5, 1.2 Hz, 2H), 7.32 (s, 1H), 6.98 (d, J=8.0 Hz, 2H), 6.50 (d, J=16.0 Hz, 2H), 5.78 (s, 1H), 4.38 (d, J=11.5 Hz, 4H), 3.87 (s, 6H), 3.80 (d, J=12.0 Hz, 4H), 1.51 (s, 12H), 1.44 (s, 6H); $^{13}$C NMR (CDCl$_3$, 125 MHz): δ 183.1, 172.2, 152.6, 140.0, 139.3, 128.2, 128.0, 122.8, 121.6, 112.3, 101.7, 98.2, 65.9, 56.0, 42.3, 30.9, 24.1, 23.3, 18.7; HRMS [ESI]$^+$ calculated for C$_{37}$H$_{44}$O$_{12}$: 703.2730 [M+Na]$^+$; found: 703.2727.

5-((1E,4Z,6E)-5-hydroxy-7-(3-hydroxy-4-methoxyphenyl)-3-oxohepta-1,4,6-trien-1-yl)-2-methoxyphenyl 2,2,5-trimethyl-1,3-dioxane-5-carboxylate (11b)

Yield=29%; mp=82-84° C.; $^1$H NMR (CDCl$_3$, 500 MHz): δ 7.71 (dd, J=15.5, 3.0 Hz, 2H), 7.40 (dd, J=8.5, 2.0 Hz, 1H), 7.31 (s, 1H), 7.19 (d, J=2.0 Hz, 1H), 7.07 (dd, J=8.5, 2.0 Hz, 1H), 6.97 (d, J=9.0 Hz, 1H), 6.87 (d, J=8.5 Hz, 1H), 6.49 (d, J=16.0 Hz, 2H), 5.78 (s, 1H), 4.38 (d, J=11.5 Hz, 2H), 3.94 (s, 3H), 3.87 (s, 3H), 3.80 (d, J=11.5 Hz, 2H), 1.51 (s, 6H), 1.44 (s, 3H); $^{13}$C NMR (CDCl$_3$, 125 MHz): δ 183.6, 183.1, 182.7, 172.2, 152.6, 148.5, 145.9, 140.4, 140.0, 139.3, 139.1, 128.7, 128.3, 128.2, 128.0, 127.9, 122.8, 122.3, 122.1, 121.6, 112.8, 112.3, 110.6, 101.6, 98.2, 65.9, 56.0, 42.3, 24.1, 23.2, 18.7; HRMS [ESI]$^+$ calculated for C$_{29}$H$_{33}$O$_9$: 525.2125 [M+H]$^+$; found: 525.2120.

((1E,3Z,6E)-3-hydroxy-5-oxohepta-1,3,6-triene-1,7-diyl)bis(6-methoxy-3,1-phenylene) bis(5-ethyl-2,2-dimethyl-1,3-dioxane-5-carboxylate) (12a)

Yield=31%; mp=88-90° C.; $^1$H NMR (CDCl$_3$, 500 MHz): δ 7.59 (d, J=15.5 Hz, 2H), 7.40 (dd, J=8.5, 2.0 Hz, 2H), 7.28 (s, 2H), 6.98 (d, J=8.5 Hz, 2H), 6.49 (d, J=15.5 Hz, 2H), 5.79 (s, 1H), 4.36 (d, J=12.0 Hz, 4H), 3.87-3.85 (m, 10H), 1.90 (q, J=7.5 Hz, 4H), 1.50 (s, 6H), 1.49 (s, 6H), 1.06 (t, J=7.5 Hz, 6H); $^{13}$C NMR (CDCl$_3$, 125 MHz): δ 183.1, 171.4, 152.7, 139.9, 139.3, 128.2, 127.9, 122.9, 121.8, 112.3, 101.6, 98.4, 64.6, 55.9, 46.3, 25.5, 24.2, 23.2, 8.2; HRMS [ESI]$^+$ calculated for C$_{39}$H$_{45}$O$_{12}$: 731.3043 [M+Na]$^+$; found: 731.3049.

5-((1E,4Z,6E)-5-hydroxy-7-(3-hydroxy-4-methoxyphenyl)-3-oxohepta-1,4,6-trien-1-yl)-2-methoxyphenyl 5-ethyl-2,2-dimethyl-1,3-dioxane-5-carboxylate (12b)

Yield=39%; mp=82-83° C.; $^1$H NMR (CDCl$_3$, 500 MHz): δ 7.58 (d, J=15.5 Hz, 2H), 7.40 (dd, J=8.5, 2.5 Hz, 1H), 7.28 (d, J=2.5 Hz, 1H), 7.19 (d, J=2.0 Hz, 1H), 7.07 (dd, J=8.5, 2.0 Hz, 1H), 6.97 (d, J=9.0 Hz, 1H), 6.86 (d, J=8.0 Hz, 1H), 6.48 (d, J=15.5 Hz, 2H), 5.78 (s, 1H), 4.36 (d, J=12.0 Hz, 2H), 3.94 (s, 3H), 3.86 (s, 3H), 3.87 (d, J=11.5 Hz, 2H), 1.90 (q, J=7.5 Hz, 2H), 1.50 (s, 3H), 1.49 (s, 3H), 1.06 (t, J=7.5 Hz, 3H); $^{13}$C NMR (CDCl$_3$, 125 MHz): δ 183.6, 182.7, 171.4, 152.6, 148.5, 145.9, 140.4, 139.9, 139.1, 128.7, 128.3, 127.9, 122.8, 122.3, 122.1, 121.7, 112.8, 112.3, 110.6, 101.6, 99.4, 64.6, 56.0, 55.9, 46.3, 25.5, 24.2, 23.2, 8.2; HRMS [ESI]$^+$ calculated for C$_{30}$H$_{34}$O$_9$: 539.2281 [M+H]$^+$; found: 539.2285.

General Procedure for the Synthesis of Compound 21a, 21b, 22a, 22b, 23a, 23b, 24a, 24b, 25, 26, 27, 28, 29, 30 and 31

The general procedure is illustrated below with compound 21a as a specific example.

A solution of 8a (1.30 g, 1.91 mmol) and 12N HCl (0.159 mL) in MeOH (7.6 mL) was stirred at room temperature for 4.0 h. The mixture was added water and stirred overnight. The mixture was filtered and the cake was dried under vacuum to afford compound 21a (1.03 g, 89.9% yield, HPLC 95.9%) as a yellow solid.

((1E,3Z,6E)-3-Hydroxy-5-oxohepta-1,3,6-triene-1,7-diyl)bis(2-methoxy-4,1-phenylene) bis(3-hydroxy-2-(hydroxymethyl)-2-methylpropenoate) (21a)

mp=142-144° C.; $^1$H NMR (CD$_3$OD, 500 MHz): δ 7.67 (d, J=16.0 Hz, 2H), 7.37 (s, 2H), 727 (d, J=8.0 Hz, 2H), 7.15 (d, J=8.0 Hz, 2H), 6.85 (d, J=8.0 Hz, 2H), 6.10 (s, 1H), 3.90 (s, 6H), 3.87-3.82 (m, 8H), 1.34 (s, 6H); $^{13}$C NMR (CD$_3$OD, 125 MHz): δ 183.2, 173.2, 151.5, 141.5, 139.7, 134.1, 124.1, 123.1, 120.9, 121.7, 111.1, 64.2, 55.2, 50.5, 16.0; HRMS [ESI]$^+$ calculated for C$_{31}$H$_{36}$O$_{12}$: 601.2285 [M+H]$^+$; found: 601.2282.

4-((1E,4Z,6E)-5-Hydroxy-7-(4-hydroxy-3-methoxyphenyl)-3-oxohepta-1,4,6-trien-1-yl)-2 methoxyphenyl 3-hydroxy-2-(hydroxymethyl)-2-methylpropanoate (21b)

mp=104-105° C.; $^1$H NMR (CDCl$_3$, 500 MHz): δ 7.63-7.58 (dd, J=15.7, 8.0 Hz, 2H), 7.19-7.17 (m, 1H), 7.14-7.11 (m, 3H), 7.06 (d, J=1.5 Hz, 1H), 6.94 (d, J=8.0 Hz, 1H), 6.53 (dd, J=31.2, 15.5 Hz, 2H), 5.84 (s, 1H), 3.99 (d, J=11.5 Hz, 2H), 3.95 (s, 3H), 3.89 (s, 3H), 3.89 (d, J=11.5 Hz, 2H), 1.33 (s, 3H); $^{13}$C NMR (CDCl$_3$, 125 MHz): δ 184.7, 181.5, 173.8, 150.7, 148.1, 146.9, 141.2, 140.6, 139.1, 134.3, 127.5, 124.5, 123.4, 123.0, 121.7, 121.1, 114.9, 111.4, 109.8, 101.5, 67.4, 56.0, 55.9, 50.4, 17.1; HRMS [ESI]$^+$ calculated for C$_{26}$H$_{28}$O$_9$: 484.1733; found: 484.1734.

((1E,3Z,6E)-3-Hydroxy-1-oxohepta-1,3,6-triene-1,7-diyl)bis(2-methoxy-4,1-phenylene) bis(2,2-bis(hydroxymethyl)butanoate) (22a)

mp=140-142° C.; $^1$H NMR (CD$_3$OD, 500 MHz): δ 7.70 (d, J=16.0 Hz, 2H), 7.37 (s, 2H), 7.26 (dd, J=8.5, 1.5 Hz, 2H), 7.13 (d, J=8.0 Hz, 2H), 6.84 (d, J=16.0 Hz, 2H), 3.95-3.84 (m, 14H), 1.76 (q, J=7.5 Hz, 4H), 1.06 (t, J=7.5 Hz, 6H); $^{13}$C NMR (CD$_3$OD, 125 MHz): δ 183.1, 172.5, 151.6, 141.3, 139.7, 134.1, 128.9, 124.1, 123.2, 122.1, 120.8, 111.3, 61.3, 61.1, 55.0, 54.0, 22.8, 7.3; HRMS [ESI]$^+$ calculated for C$_{33}$H$_{40}$O$_{12}$: 628.2520; found: 628.2522.

4-((1E,4Z,6E)-5-Hydroxy-7-(4-hydroxy-3-methoxyphenyl)-3-oxohepta-1,4,6-trien-1-yl)-2-methoxyphenyl 2,2-bis(hydroxymethyl)butanoate (22b)

mp=82-83° C.; $^1$H NMR (CD$_3$OD, 500 MHz): δ 7.63 (d, J=15.5 Hz, 2H), 7.35 (s, 1H), 7.25-7.24 (m, 2H), 7.15-7.11 (m, 2H), 6.84 (dd, J=8.5, 3.0 Hz, 1H), 6.79 (d, J=15.5 Hz, 1H), 6.67 (d, J=16.0 Hz, 1H), 6.04 (s, 1H), 3.94 (d, J=11.0

Hz, 2H), 3.93 (s, 3H), 3.89 (s, 3H), 3.85 (d, 11.0 Hz, 2H), 1.76 (q, J=7.5 Hz, 2H), 1.06 (t, J=7.5 Hz, 3H); $^{13}$C NMR (CD$_3$OD, 125 MHz): δ 185.1, 181.3, 172.6, 151.5, 149.2, 148.0, 141.4, 141.1, 138.9, 134.3, 127.0, 127.4, 124.0, 123.1, 122.9, 120.9, 120.7, 115.2, 111.2, 110.4, 61.2, 55.1, 55.0, 54.0, 22.8, 7.1; HRMS [ESI]$^+$ calculated for C$_{27}$H$_{30}$O$_9$: 498.1890; found: 499.1891.

((1E,3Z,6E)-3-Hydroxy-5-oxohepta-1,3,6-triene-1,7-diyl)bis(4,1-phenylene) bis(3-hydroxy-2-(hydroxymethyl)-2-methylpropanoate) (23a)

mp=192-194° C.; $^1$H NMR (CD$_3$OD, 500 MHz): δ 7.80 (d, J=8.0 Hz, 4H), 7.67 (d, J=16.0 Hz, 2H), 7.17 (d, J=8.0 Hz, 4H), 6.87 (d, J=16.0 Hz, 2H), 6.20 (s, 1H), 3.71-3.68 (m, 4H), 3.56-3.53 (m, 4H), 1.22 (s, 6H); $^{13}$C NMR (CD$_3$OD, 125 MHz): δ 183.6, 174.1, 152.6, 139.9, 132.6, 129.9, 124.6, 123.0, 102.3, 64.5, 51.3, 17.1; HRMS [ESI]$^+$ calculated for C$_{29}$H$_{32}$O$_{10}$: 540.2074 [M+H]$^+$; found: 540.2070.

4-((1E,4Z,6E)-5-hydroxy-7-(4-hydroxyphenyl)-3-oxohept-1,4,6-trien-1-yl)phenyl 3-hydroxy-2-(hydroxymethyl)-2-methylpropanoate (23b)

mp=206-208° C.; $^1$H NMR (CD$_3$OD, 500 MHz): δ 7.69 (d, J=8.5 Hz, 2H), 7.65 (dd, J=16.0, 4.5 Hz, 2H), 7.53 (d, J=8.5 Hz, 2H), 7.20 (d, J=8.5 Hz, 2H), 6.85 (d, J=8.5 Hz, 2H), 6.80 (d, J=16.0 Hz, 1H), 6.66 (d, J=16.0 Hz, 1H), 6.04 (s, 1H), 3.88 (d, J=11.0 Hz, 2H), 3.76 (d, J=11.0 Hz, 2H), 1.35 (s, 3H); $^{13}$C NMR (CD$_3$OD, 125 MHz): δ 185.5, 181.2, 173.8, 160.5, 152.5, 141.4, 139.0, 132.7, 129.9, 128.8, 126.9, 124.0, 122.1, 121.0, 115.0, 64.5, 51.5, 17.9; HRMS [ESI]$^+$ calculated for C$_{24}$H$_{24}$O$_7$: 424.1522; found: 425.1523.

((1E,6E)-3,5-Dioxohepta-1,6-diene-1,7-diyl)bis(2-methoxy-5,1-phenylene) bis(3-hydroxy-2-(hydroxymethyl)-2-methylpropanoate) (24a)

mp=194-196° C.; $^1$H NMR (CD$_3$OD, 500 MHz): δ 7.61 (d, J=16.0 Hz, 2H), 7.51 (dd, J=8.5, 1.5 Hz, 2H), 7.47 (s, 2H), 7.14 (d, J=8.5 Hz, 2H), 6.70 (d, J=16.0 Hz, 2H), 6.03 (s, 1H), 3.89-3.83 (m, 14H), 1.44 (s, 6H); $^{13}$C NMR (d-DMSO, 125 MHz): δ 183.5, 173.4, 153.2, 140.3, 139.8, 128.6, 128.0, 123.2, 122.5, 113.5, 101.7, 64.0, 56.6, 51.0, 17.3; HRMS [ESI]$^+$ calculated for C$_{31}$H$_{36}$O$_{16}$: 623.2104 [M+Na]$^+$; found: 623.2102.

5-((1E,6E)-7-(3-Hydroxy-4-methoxyphenyl)-3,5-dioxohepta-1,6-dien-1-yl)-2-methoxyphen yl 3-hydroxy-2-(hydroxymethyl)-2-methylpropanoate (24b)

mp=184-186° C.; $^1$H NMR (CD$_3$OD, 500 MHz): δ 7.51 (dd, J=16.0, 4.0 Hz, 2H), 7.41-7.39 (m, 2H), 7.10 (s, 1H), 7.05-7.02 (m, 2H), 6.90 (d, J=8.5 Hz, 1H), 6.54 (dd, J=23.0, 16.0 Hz, 2H), 5.87 (s, 1H), 3.89-3.84 (m, 7H), 3.82 (s, 3H), 1.36 (s, 3H); $^{13}$C NMR (CD$_3$OD, 125 MHz): δ 183.8, 182.3, 173.3, 152.7, 149.9, 146.5, 140.7, 140.1, 138.9, 128.2, 127.6, 122.4, 121.7, 121.5, 112.3, 113.4, 112.2, 111.1, 64.3, 55.1, 54.9, 50.5, 16.1; HRMS [ESI]$^+$ calculated for C$_{26}$H$_{28}$O$_9$: 507.1631[M+Na]$^+$; found: 507.1628.

5-((1E,4Z,6E)-5-Hydroxy-7-(3-hydroxy-4-methoxyphenyl)-3-oxohepta-1,4,6-tries-1-yl-2-methoxyphenyl 2,2-bis(hydroxymethyl)butanoate (25)

mp=133-135° C.; $^1$H NMR (CD$_3$OD, 500 MHz): δ 7.59-7.54 (m, 2H), 7.49 (d, J=8.5 Hz, 1H), 7.44 (s, 1H), 7.13-7.09 (m, 3H), 6.96 (d, J=8.5 Hz, 1H), 6.63 (dd, J=30.2, 15.5 Hz, 2H), 5.97 (s, 1H), 3.96-3.86 (m, 10H), 1.76 (q, J=8.5 Hz, 2H), 1.07 (t, J=8.5 Hz, 3H); $^{13}$C NMR (CD$_3$OD, 125 MHz): δ 183.9, 182.4, 172.6, 152.9, 149.9, 146.6, 140.7, 140.0, 138.9, 128.2, 127.7, 122.4, 121.7, 121.5, 113.4, 112.2, 111.1, 100.8, 61.2, 55.0, 54.9, 54.0, 22.7, 7.1; HRMS [ESI]$^+$ calculated for C$_{27}$H$_{30}$O$_9$: 521.1787 [M+Na]$^+$; found: 521.1785.

((1E,3Z,6E)-3-hydroxy-5-oxohepta-1,3,6-triene-1,7-diyl)bis(2-ethoxy-4,1-phenylene) bis(3-hydroxy-2-(hydroxymethyl)-2-methylpropanoate) (26)

mp=153-155° C.; $^1$H NMR (d-DMSO, 500 MHz): δ 7.63 (d, J=15.8 Hz, 2H), 7.47 (s, 4H), 7.32 (d, J=8.3 Hz, 2H), 7.09 (d, J=8.1 Hz, 2H), 6.97 (d, J=15.8 Hz, 2H), 6.17 (s, 1H), 4.81-4.79 (m, 4H), 4.09 (q, J=6.9 Hz, 4H), 3.63 (d, J=5.3 Hz, 8H), 1.31 (t, J=6.9 Hz, 6H), 1.20 (s, 6H); ESI-MS 629.24 [M+1]$^+$.

((1E,3Z,6E)-3-hydroxy-5-oxohepta-1,3,6-triene-1,7-diyl)bis(2-ethoxy-4,1-phenylene) bis(2,2-bis(hydroxymethyl)butanoate) (27)

mp=161-162° C.; $^1$H NMR (d-DMSO, 500 MHz): δ 7.63 (d, J=15.9 Hz, 2H), 7.48 (s, 4H), 7.32 (d, J=8.0 Hz, 2H), 7.06 (d, J=8.1 Hz, 2H), 6.97 (d, J=15.9 Hz, 2H), 6.18 (s, 1H), 4.74-4.72 (m, 4H), 4.09 (q, J=6.9 Hz, 4H), 3.65 (s, 8H), 1.59 (q, J=7.4 Hz, 4H), 1.30 (t, J=6.9 Hz, 6H), 0.95 (t, J=7.3 Hz, 6H); LRMS [ESI]$^+$ calculated for C$_{35}$H$_{45}$O$_{12}$: 657.29 [M+H]$^+$; found: 657.32.

((1E,6E)-3,5-dioxohepta-1,6-diene-1,7-diyl)bis(2-(trifluoromethoxy)-4,1-phenylene) bis(3-hydroxy-2-(hydroxymethyl)-2-methylpropanoate) (28)

$^1$H NMR (d-DMSO, 500 MHz): δ 7.68-7.63 (m, 6H), 7.37 (d, J=8.2 Hz, 2H), 6.85 (d, J=15.7 Hz, 2H), 6.12 (s, 1H), 4.74-4.72 (m, 4H), 3.82 (s, 8H), 1.33 (s, 6H); LRMS [ESI]$^+$ calculated for C$_{31}$H$_{30}$F$_6$O$_{12}$: 709.17 [M+H]$^+$; found: 709.38.

((1E,6E)-3,5-dioxohepta-1,6-diene-1,7-diyl)bis(2-(trifluoromethoxy)-4,1-phenylene) bis(2,2-bis(hydroxymethyl)butanoate) (29)

$^1$H NMR (d-DMSO, 500 MHz): δ 7.93 (s, 2H), 7.85 (d, J=8.5 Hz, 2H), 7.68 (d, J=16.0 Hz, 2H), 7.34 (d, J=8.5 Hz, 2H), 7.07 (d, J=16.0 Hz, 2H), 6.22 (s, 1H), 3.69-3.63 (m, 8H), 1.62 (q, J=7.4 Hz, 4H), 0.89 (t, J=7.4 Hz, 6H); LRMS [ESI]$^+$ calculated for C$_{33}$H$_{35}$F$_6$O$_2$: 737.20 [M+H]$^+$; found: 737.22.

((1E,3Z,6E)-3-hydroxy-5-oxohepta-1,3,6-triene-1,7-diyl)bis(2,6-dimethoxy-4,1-phenylene) bis(3-hydroxy-2-(hydroxymethyl)-2-methylpropanoate) (30)

$^1$H NMR (d-DMSO, 500 MHz): δ 7.65 (d, J=15.5 Hz, 2H), 7.15 (s, 4H), 7.03 (d, J=15.5 Hz, 2H), 6.23 (s, 1H), 3.81 (s, 12H), 3.69-3.62 (m, 8H), 1.21 (s, 6H); $^{13}$C NMR (d-DMSO, 125 MHz): δ 183.6, 172.9, 152.6, 140.8, 133.3, 130.6, 125.1, 106.0, 101.9, 63.8, 56.8, 50.8, 17.4, 10.4; LRMS [ESI]$^+$ calculated for C$_{33}$H$_{41}$O$_14$: 661.25 [M+H]$^+$; found: 661.3.

((1E,6E)-3,5-dioxohepta-1,6-diene-1,7-diyl)bis(2,6-diethyl-4,1-phenylene) bis(3-hydroxy-2-(hydroxymethyl)-2-methylpropanoate) (31)

$^1$H NMR (CDCl$_3$, 500 MHz): δ 7.64 (d, J=16.0 Hz, 2H), 7.33 (s, 4H), 6.61 (d, J=15.5 Hz, 2H), 5.89 (s, 1H), 4.52-4.36

(m, 2H), 4.15-4.12 (m, 2H), 3.92-3.83 (m, 4H), 2.56 (m, 8H), 1.48 (s, 3H), 1.33 (s, 3H), 1.28-1.18 (m, 12H); $^{13}$C NMR (CDCl$_3$, 125 MHz): δ 183.3, 174.3, 172.7, 171.1, 148.3, 140.1, 136.8, 136.6, 133.3, 126.8, 124.0, 101.6, 68.4, 65.9, 64.8, 49.7, 48.7, 29.7, 23.3, 20.7, 17.6, 17.2, 14.2; LRMS [ESI]$^+$ calculated for C$_{37}$H$_{48}$O$_{10}$: 653.33 [M+H]$^+$; found: 653.4.

General Procedure for the Synthesis of Compounds 33, 35a, 35b, 35c, 35d, 35e, 36 and 37.

The general procedure is illustrated below with compound 35a as a specific example. To a solution of 8a (1.70 g, 2.50 mmol) in DMF (30 mL) was added K$_2$CO$_3$ (0.54 g, 3.00 mmol) and CH$_3$I (1.02 g, 5.50 mmol) sequentially at 0° C. The reaction mixture was stirred at rt for 12 h and then H$_2$O (40 mL) was added to quench the reaction. The aqueous layer was separated and extracted with EtOAc (3×35 mL). The combined organic layer was dried over MgSO$_4$, filtered and concentrated to give the crude product, which was subjected to an acid-promoted hydrolysis reaction [5 mL 2N HCl$_{(aq)}$, 15 mL THF] without any purification. The reaction was followed by TLC until no starting material was present. The resulting mixture was then concentrated to give the crude product, which was then purified by flash chromatography on silica gel with MeOH/CH$_2$Cl$_2$ (1:19) to afford compound 35a (0.63 g, 40% yield for two steps) as a yellow solid.

((1E,6)-4,4-Dimethyl-3,5-dioxohept-1,6-diene-1,7-diyl)bis(2-methoxy-4,1-phenylene) bis(3-hydroxy-2-(hydroxymethyl)-2-methylpropanoate) (35a)

44% yield. mp=173-175° C.; $^1$H NMR (CDCl$_3$, 500 MHz): δ 7.68 (d, J=15.5 Hz, 2H), 7.15 (d, J=8.0 Hz, 2H), 7.10-7.06 (m, 4H), 6.74 (d, J=15.5 Hz, 2H), 3.94 (d, J=11.5 Hz, 4H), 3.84-3.82 (m, 10H), 1.49 (s, 6H), 1.29 (s, 6H); $^{13}$C NMR (CDCl$_3$, 125 MHz): δ 197.9, 173.6, 150.8, 143.6, 141.4, 133.3, 123.4, 122.0, 121.6, 111.8, 66.9, 60.9, 56.1, 50.3, 21.0, 17.1; HRMS [ESI]$^+$ calculated for C$_{33}$H$_{40}$O$_{12}$: 651.2417 [M+Na]$^+$; found: 651.2414.

4-((1E,4Z,6E)-7-(3,4-dimethoxyphenyl)-5-hydroxy-3-oxohepta-1,4,6-triene-1-yl)-2-methoxyphenyl 3-hydroxy-2-(hydroxymethyl)-2-methylpropanoate (33)

40% yield. mp=99-101° C.; $^1$H NMR (CDCl$_3$, 500 MHz): δ 7.62 (dd, J=15.5, 13.5 Hz, 2H), 7.21-7.09 (m, 5H), 6.90 (d, J=9.0 Hz, 1H), 6.54 (dd, J=24.0, 16.0 Hz, 2H), 5.85 (s, 1H), 4.00-3.88 (m, 13H), 1.33 (s, 3H); $^{13}$C NMR (CDCl$_3$, 125 MHz): δ 184.5, 181.7, 173.8, 151.2, 150.7, 149.2, 141.0, 140.7, 139.1, 134.3, 129.1, 127.9, 124.5, 123.4, 122.8, 122.0, 121.1, 111.4, 111.2, 109.8, 101.6, 67.4, 56.1, 56.0, 55.9, 50.4, 17.1; LRMS [ESI]$^+$ calculated for C$_{27}$H$_{30}$O$_9$: 521.1787 [M+Na]$^+$; found: 527.1787.

((1E,6E)-4,4-Diethyl-3,5-dioxohepta-1,6-diene-1,7-diyl)bis(2-methoxy-4,1-phenylene) bis(3-hydroxy-2-(hydroxymethyl)-2-methylpropanoate) (35b)

43% yield. mp=189-191° C.; $^1$H NMR (CD$_3$OD, 500 MHz): δ 7.70 (d, J=16.0 Hz, 2H), 7.29 (s, 2H), 7.22 (d, J=8.0 Hz, 2H), 7.11 (d, J=8.5 Hz, 2H), 6.97 (d, J=15.5 Hz, 2H), 3.87-3.82 (m, 14H), 2.14 (q, J=8.0 Hz, 4H), 1.34 (s, 6H), 0.79 (t, J=8.0 Hz, 6H); $^{13}$C NMR (CD$_3$OD, 125 MHz): δ 198.4, 173.2, 151.2, 142.9, 142.0, 133.3, 123.1, 122.2, 121.9, 111.9, 68.6, 64.2, 55.2, 50.5, 22.0, 16.0, 6.9; HRMS [ESI]$^+$ calculated for C$_{35}$H$_{44}$O$_{12}$: 679.2730 [M+Na]$^+$; found: 679.2731.

((1E,6E)-4,4-Dibenzyl-3,5-dioxohepta-1,6-dine-1,7-diyl)bis(2-methoxy-4,1-phenylene) bis(3-hydroxy-2-(hydroxymethyl)-2-methylpropanoate) (35c)

35% yield. mp=253-255° C.; $^1$H NMR (CDCl$_3$, 500 MHz): δ 7.67 (d, J=15.0 Hz, 2H), 7.26-7.12 (m, 14H), 6.91 (s, 2H), 6.54 (d, J=15.5 Hz, 2H), 3.96-3.94 (m, 4H), 3.88-3.80 (m, 10H), 3.41 (s, 4H), 1.29 (s, 6H); $^{13}$C NMR (CDCl$_3$, 125 MHz): δ 196.7, 173.6, 150.8, 142.7, 141.5, 136.2, 133.3, 130.5, 128.5, 128.2, 123.7, 123.4, 122.4, 111.7, 70.3, 67.9, 67.1, 56.1 50.3, 38.2, 17.1; HRMS [ESI]$^+$ calculated for C$_{45}$H$_{48}$O$_{12}$: 803.3043 [M+Na]$^+$; found: 803.3041.

((1E,6E)-3,5-Dioxo-4,4-di(prop-2-yn-1-yl)hepta-1,6-diene-1,7-diyl)bis(2-methoxy-4,1-phenylene) bis(3-hydroxy-2-(hydroxymethyl)-2-methylpropanoate) (35d)

45% yield. mp=216-218° C.; $^1$H NMR (CDCl$_3$, 500 MHz): δ 7.73 (d, J=15.5 Hz, 2H), 7.19-7.17 (m, 2H), 7.11-7.08 (m, 4H), 6.77 (d, J=15.0 Hz, 2H), 3.96 (d, J=11.5 Hz, 4H), 3.86-3.83 (m, 10H), 3.19 (s, 4H), 2.06 (s, 2H), 1.29 (s, 6H); $^{13}$C NMR (CDCl$_3$, 125 MHz): δ 193.4, 173.6, 150.9, 145.0, 141.8, 133.0, 123.5, 122.4, 120.4, 111.9, 78.7, 72.4, 67.3, 67.1, 56.2, 50.3, 21.1, 17.1; HRMS [ESI]$^+$ calculated for C$_{37}$H$_{40}$O$_{12}$: 699.2417 [M+Na]$^+$; found: 699.2414.

((1E,6E)-4,4-diallyl-3,5-dioxohepta-1,6-diene-1,7-diyl)bis(2-methoxy-4,1-phenylene) bis(3-hydroxy-2-(hydroxymethyl)-2-methylpropanoate) (35e)

48% yield. mp=195-197° C.; $^1$H NMR (d-DMSO, 500 MHz): δ 7.59 (d, J=15.5 Hz, 2H), 7.48 (s, 2H), 7.35 (dd, J=8.2, 1.5 Hz, 2H), 7.12-7.04 (m, 4H), 5.59-5.52 (m, 2H), 5.12-5.04 (m, 4H), 4.82-4.80 (m, 4H), 3.78 (s, 6H), 3.60 (s, 8H), 2.84 (d, J=7.2 Hz, 4H), 1.17 (s, 6H); LRMS [ESI]$^+$ calculated for C$_{37}$H$_{44}$O$_{12}$: 681.29 [M+H]$^+$; found: ESI-MS 681.43 [M+1]$^+$.

((1E,6E)-4,4-Dimethyl-3,5-dioxohepta-1,6-diene-1,7-diyl)bis(4,1-phenylene) bis(3-hydroxy-2-(hydroxymethyl)-2-methylpropanoate) (36)

42% yield. mp=138-140° C.; $^1$H NMR (CDCl$_3$, 500 MHz): δ 7.70 (d, J=15.5 Hz, 2H), 7.53 (d, J=8.0 Hz, 4H), 7.10 (d, J=8.5 Hz, 4H), 6.74 (d, J=15.5 Hz, 2H), 4.05 (d, J=11.5 Hz, 4H), 3.82 (d, J=11.0 Hz, 4H), 1.47 (s, 6H), 1.21 (s, 6H); $^{13}$C NMR (CDCl$_3$, 125 MHz): δ 197.9, 174.4, 152.3, 143.1, 132.2, 129.8, 122.2, 121.6, 68.7, 60.9, 49.6, 21.0, 17.0; HRMS [ESI]$^+$ calculated for C$_{31}$H$_{36}$O$_{10}$: 591.2206 [M+Na]$^+$; found: 591.2209.

((1E,6E)-4,4-Dimethyl-3,5-dioxohepta-1,6-dien-1,7-diyl)bis(2-methoxy-5,1-phenylene) bis(3-hydroxy-2-(hydroxymethyl)-2-methylpropanoate) (37)

41% yield. $^1$H NMR (CDCl$_3$, 500 MHz): δ 7.63 (d, J=15.5 Hz, 2H), 7.36 (dd, J=8.5, 2.0 Hz, 2H), 7.27 (d, J=8.5 Hz, 2H), 6.91 (d, J=8.5 Hz, 2H), 6.62 (d, J=15.5 Hz, 2H), 3.94 (d, J=11.5 Hz, 4H), 3.84 (d, J=11.5 Hz, 4H), 3.82 (s, 6H), 1.44 (s, 6H), 1.29 (s, 6H); $^{13}$C NMR (CDCl$_3$, 125 MHz): δ 197.9, 173.8, 152.6, 143.1, 139.6, 129.1, 127.7, 122.2, 120.4, 112.2, 67.2, 60.8, 56.2, 50.3, 21.0, 17.1; HRMS [ESI]+ calculated for C₃₃H₄₀O₁₂: 628.2520; found: 629.2592.

4-((1E,6E)-7-(4-hydroxy-3-methoxyphenyl)-3,5-dioxohept-1,6-den-1-yl)-2-methoxyphenyl 3-hydroxy-2,2-bis(hydroxymethyl)propanoate (38a) and 3-(4-((1E,6E)-7-(4-hydroxy-3-methoxyphenyl)-3,5-dioxohepta-1,6-dien-1-yl)-2-methoxyphenoxy-2,2-bis(hydroxymethyl)-3-oxopropyl-3-hydroxy-2,2-bis (hydroxymethyl)propanoate (38b)

To a stirred solution of curcumin (0.40 g, 1.09 mmol) in DMF (2.17 mL) were added sequentially EDCI (0.62 g, 3.27 mmol), HOBt (33.0 mg, 0.22 mmol), 3-hydroxy-2,2-bis(hydroxymethyl)propanoic acid (0.49 g, 3.27 mmol) and DMAP (27.0 mg, 0.22 mmol) at rt. The reaction mixture was stirred at room temperature. After 12 h, the solution was extracted with EA/H₂O. The combined organic extracts were washed with brine, dried over MgSO₄, filtered and concentrated to give the crude product which was then purified briefly on silica gel with MeOH/CH₂Cl₂ (3% MeOH to 20% MeOH) to afford 69 mg (10.0% yield) 38a and 25 mg (3.6% yield) 38b as light-orange solid.

38a, ¹H NMR (DMSO-d₆, 500 MHz): δ 9.66 (s, 1H), 7.55 (d, J=15.5 Hz, 2H), 7.44 (s, 1H), 7.27~7.30 (m, 2H), 7.13 (d, J=8.0 Hz, 1H), 7.05 (d, J=8.0 Hz, 1H), 6.91 (d, J=16.0 Hz, 1H), 6.74~6.80 (m, 2H), 6.09 (s, 1H), 4.60 (t, J=5.5 Hz, 3H), 3.80 (s, 3H), 3.76 (s, 3H), 3.65 (d, J=5.5 Hz, 6H); ESI-MS 501.18 [M+1]+.

38b, ¹H NMR (DMSO-d₆, 500 MHz): δ 9.71 (s, 1H), 7.5&-7.62 (m, 2H), 7.49 (s, 1H), 7.31~7.34 (m, 2H), 7.17 (d, J=8.0 Hz, 1H), 7.12 (d, J=8.0 Hz, H), 6.96 (d, J=16.0 Hz, 1H), 6.78~6.83 (m, 2H), 6.13 (s, 1H), 4.86 (t, J=5.0 Hz, 2H), 4.55 (t, J=5.0 Hz, 3H), 4.29 (s, 2H), 3.84 (s, 3H), 3.83 (s, 3H), 3.73 (d, J=4.0 Hz, 4H), 3.56 (d, J=5.0 Hz, 6H); ESI-MS 633.40 [M+1]+.

((1E,6E)-4,4-bis(hydroxymethyl)-3,5-dioxohepta-1,6-diene-1,7-diyl)bis(2-methoxy-4,1-phenylene) bis (2,2,5-trimethyl-1,3-dioxane-5-carboxylate) (39)

To a solution of 8a (1 g, 1.47 mmol) in THF (7.35 mL, contain 0.6M formaldehyde) was added DBU (38.9 mg, 0.04 mmol). The reaction mixture was stirred at 0☐ for 30 min and then warm to rt. The solution was concentrated and then purified briefly on silica gel with EA/n-hexane (1:2) to afford 39 as yellow solid. Yield 41.7%. ESI-MS m/z 741.33 [M+1]+.

((1E,6E)-4,4-bis(hydroxymethyl)-3,5-dioxohepta-1,6-diene-1,7-diyl)bis(2-methoxy-4-phenylene) bis(3-hydroxy-2-(hydroxymethyl)-2-methylpropanoate) (40)

A solution of 39 (0.34 g, 0.46 mmol) and 6 N HCl (0.15 mL) in MeOH (1.83 mL) was stirred at room temperature for overnight. The reaction mixture was concentrated under vacuum to give the crude product, which was purified on silica gel with MeOH/CH₂Cl₂ (1:20) to afford 40.0 mg of compound 40 as orange oil. Yield 13.2%; mp=234-237° C.; ¹H NMR (d-DMSO, 500 MHz): δ 7.52 (d, J=15.6 Hz, 2H), 7.44 (s, 2H), 7.30 (d, J=8.2 Hz, 2H), 7.08-7.04 (m, 4H), 5.16 (br s, 6H), 4.19 (s, 4H), 3.78 (s, 6H), 3.61 (d, 8H), 1.17 (s, 6H); LRMS [ESI]+ calculated for C₃₃H₄₀O₄: 661.25 [M+H]+; found: 661.4.

((1E,6E)-4,4-bis(acetoxymethyl)-3,5-dioxohepta-1, 6-diene-1,7-diyl)bis(2-methoxy-4,1-phenylene) bis (3-hydroxy-2-(hydroxymethyl)-2-methylpropanoate) (41)

A solution of 39 (0.12 g, 0.15 mmol) and 6 N HCl (0.05 mL) in MeOH (0.56 mL) was stirred at room temperature for 1 h. The reaction mixture was concentrated under vacuum to give the crude product, which was purified on silica gel with MeOH/CH₂Cl₂ (1:20) to afford 32.0 mg of 41 as yellow solid. Yield 30.5%; ¹H NMR (DMSO-d₆, 500 MHz): δ 7.64 (d, J=15.5 Hz, 2H), 7.48 (a, 2H), 7.34 (d, J=8.0 Hz, 2H), 7.17 (d, J=15.5 Hz, 2H), 7.03 (d, J=8.0 Hz, 2H), 4.77 (t, J=5.5 Hz, 8H), 3.75 (s, 6H), 3.55-3.58 (m, 8H), 1.93 (s, 6H), 1.14 (s, 6H); ESI-MS m/z 745.55 [M+1]+.

(1E,6E)-1,7-bis(3,4-dimethoxyphenyl)-4,4-bis(hydroxymethyl)hepta-1,6-diene-3,5-dione (42)

To a solution of dimethoxycurcumin (1.27 g, 3.20 mmol) in THF (16.00 mL, contain 0.6M formaldehyde) was added DBU (14.6 mg, 0.10 mmol). The reaction mixture was stirred at 0° C. for 30 min and then warm to rt. The solution was concentrated and then purified on silica gel with MeOH/CH₂Cl₂ (1:32) to afford 558 mg of 42 as yellow solid. Yield 42%; ¹H NMR (DMSO-d₆, 500 MHz): δ 7.48 (d, J=15.5 Hz, 2H), 7.28-7.22 (m, 4H), 6.97-6.91 (m, 4H), 4.76 (t, J=4.5 Hz, 2H), 4.17 (d, J=4.5 Hz, 4H), 3.78 (d, J=4.0 Hz, 12H); ESI-MS m/z 457.14 [M+1]+.

2,2-bis((E)-3-(3,4-dimethoxyphenyl)acryloyl)propane-1,3-diylbis(3-hydroxy-2-(hydroxymethyl)-2-methylpropanoate) (43)

To a solution of 42 (0.17 g, 0.37 mmol) in CH₂C₂ (4.00 mL) was added NEt₃ (0.15 mL, 1.10 mmol), DMAP (0.11 g, 0.92 mmol) and 2,2,5-trimethyl-1,3-dioxane-5-carbonyl chloride (0.21 g, 1.10 mmol) sequentially at rt. The reaction mixture was stirred at rt for overnight. Then the solution was concentrated and then purified on silica gel with MeOH/CH₂CO₂ (1:32) to afford 32.7 mg 43int as yellow solid. Yield 11.6%; ESI-MS m/z 769.35 [M+1]+.

A solution of 43fat (32.0 mg, 0.042 mmol) and 12 N HCl (24.0 µL) in MeOH (0.40 mL) was stirred at rt for 16 h. The reaction mixture was concentrated under vacuum to give the crude product, which was purified on silica gel with MeOH/CH₂Cl₂ (1:19) to afford compound 43 as yellow solid (16.2 mg). Yield 56.5%; ¹H NMR (DMSO-d₆, 500 MHz): δ 7.63 (d, J=15.4 Hz, 2H), 7.35-7.29 (m, 4H), 7.03 (d, J=15.4 Hz, 2H), 6.98 (d, J=8.43 Hz, 2), 4.74 (s, 4H), 4.60 (t, J=5.46 Hz, 4H), 3.79 (s, 12H), 3.41-3.34 (m, 8H), 0.95 (s, 6H); ESI-MS m/z 689.55 [M+1]+.

2,2-bis((E)-3-(3,4-dimethoxyphenyl)acryloyl)propane-1,3-diyl diacetate (44)

To a solution of 42 (75.0 mg, 0.16 mmol) in CH₂Cl₂ (2.00 mL) was added NEt₃ (0.069 mL, 0.49 mmol), DMAP (50.1 mg, 0.41 mmol) and acyl chloride (35.1 µL, 0.49 mmol) sequentially at rt. The reaction mixture was stirred at rt overnight. Then the solution was concentrated and then purified on silica gel with MeOH/CH₂Cl₂ (1:32) to afford 75.5 mg 44 as yellow solid. Yield 85.2%; ¹H NMR (DMSO-d₆, 500 MHz): δ 7.64 (d, J=15.0 Hz, 2H), 7.37 (s, 2H), 7.32-7.30 (m, 2H), 7.06 (d, J=15.0 Hz, 2H), 6.98 (d, J=8.0 Hz, 2H), 4.78 (s, 4H), 3.78 (s, 12H), 1.97-1.93 (m, 6H); ESI-MS m/z 541.12 [M+1]+.

3-2. Biological Assay
3-2-1. Cell Viability Assay

Cell viability was evaluated by measuring the reduction in MTT to yield blue formazan. Cells were cultured in 96-well plates, allowed to attach overnight, and then treated with compounds. After treatment, MTT solution (1 mg/ml) was added to each well, and plates were incubated for another 4 h. Medium were removed, blue formazan was dissolved in DMSO, and the absorbance was read at 570 nm[20].

3-2-2. Cell Morphology

For morphological observations, cells were visualized and photographed using a phase-contrast microscope equipped with a digital camera (Leica Microsystems, Wetzlar, Germany)[21].

3-2-3. Cell Cycle Distribution Analysis

For cell cycle and sub-G1 (apoptosis) determinations, the harvested cells were fixed gently by putting 70% ethanol in 4° C. overnight and then re-suspended in PBS containing 40 μg/ml PI and 0.1 mg/ml RNase and 0.1% Triton X-100 in dark room for 30 min at 37° C. Those cells were analyzed with a flow cytometer equipped with an argon ion laser at 488 nm wavelength[22].

3-2-4. CDK1 Kinase Assay

CDK1 kinase activity was analyzed according to the protocol of Medical & Biological Laboratories CDK1 kinase assay kit (MBL International, Nagoya, Japan). In brief; the ability of cell extract prepared from each treatment was measured to phosphorylate its specific substrate, MV Peptide as described previously[23].

3-2-5. Apoptosis Analysis

After treatments, cells were harvested and stained with annexin V and propidium iodide using the Annexin V: FITC Apoptosis Detection Kit II (BD Biosciences) and subjected to flow cytometry (FACScalibur; Becton-Dickinson, Mountain View, Calif., USA). The percentages of apoptotic cells were quantified with CellQuest software (Becton-Dickinson)[24].

3-2-6. Cells Lysate Preparation and Western Blot Analysis

After treatments, cells were harvested, washed, and suspended in PBS containing proteinase inhibitors and then disrupted with sonication. Protein concentrations were estimated using the Protein Assay kit from Bio-Rad (Hercules, Calif., USA). Samples were resolved with SDS-PAGE and transferred to a polyvinylidene difluoride membrane (EMD Millipore). Each membrane was blocked in 5% (w/v) nonfat milk in Tris-buffered saline with 0.1% (v/v) Tween-20 for 1 h followed by incubation with specific primary antibodies at 4° C. overnight. Each membrane was then incubated with horseradish peroxidase-conjugated secondary antibodies at room temperature for 1 h. Protein signals were detected with the Immobilon Western Chemiluminescent HRP Substrate (EMD Millipore) and visualized using the LAS-4000 imaging system (Fuji, Tokyo, Japan)[25].

3-2-7. Immunofluorescence Staining

Cells were grown on sterile coverslips placed in a 6-well plate. After treatments, cells were fixed with 4% (w/v) paraformaldehyde and permeabilized with 0.2% (v/v) Triton X-100 in PBS. After blocking with 2% (w/v) bovine serum albumin in PBS, tubulin was detected using anti-LC3B and anti-p62 antibody followed by reaction with FITC or PE-conjugated secondary antibody (BD Biosciences). Coverslips were mounted on glass slides with Prolong Gold Antifade Reagent containing DAPI (Invitrogen), and fluorescence images were taken on a Leica Microsystems TCS SP2 Confocal Spectral microscope[26].

3-2-8. cDNA Microarray

The cells were incubated with or without 21a. After exposure, cell pellets were collected, and the total RNA from each treatment was purified using the Qiagen RNeasy Mini Kit (Qiagen, Valencia, Calif., USA). The RNA purity was determined to check the quality at 260/280 nm using a NanoDrop 1000 Spectrophotometer (Thermo Fisher Scientific, Wilmington, Del., USA). mRNA was amplified and labeled using the Gene-Chip WT Sense Target Labeling and Control Reagents kit (Affymetrix, Santa Clara, Calif., USA) for expression analysis. The synthesized cDNA was labeled with fluorescence and then hybridized for 17 h using AffymetrixGeneChip Human Gene 1.0 ST array (Affymetrix) to determine microarray hybridization following the manufacturer's protocols. The arrays were subsequently washed using Fluidics Station 450 (Affymetrix), stained with streptavidin-phycoerythrin (Gene-Chip Hybridization, Wash, and Stain kit, Affymetrix), and scanned on a GeneChip Scanner 3000 (Affymetrix). The localized concentrations of fluorescent molecules were quantitated and analyzed using Expression Console Software (Affymetrix) with default RMA parameters as previously described (Chang et al. 2012; Liu et al. 2013). The gene expression level of a 2.0-fold change was considered a difference in 21a-treated cells in vitro[27].

3-2-8. In Vivo Antitumor Activity Assays

Female nu/nu mice (5 weeks old) were from National Laboratory Animal Center, Taipei, Taiwan. Mice were maintained under the procedures and guidelines from the Institutional Animal Care and Use Committee of the National Health Research Institutes, Taipei, Taiwan. All experiments were supervised under the Institutional Animal Care and Use Committee, China Medical University, Taichung, Taiwan. MDA-MB-231 breast cancer cells ($5 \times 10^6$ cells per mouse) were suspended in 0.1 ml of Matrigel solution (50% (v/v) Matrigel in PBS) and inoculated into the mammary fat pads of the mice. When the tumor masses reached 100 mm³, the tumor-bearing mice were randomly divided into groups for treatments with vehicle (propylene glycol, 0.1 ml), curcumin (100 mg/kg) or 21a (5, 10, 25, and 50 mg/kg). Compounds was administered P.O. once every day for 32 days. Tumor size and mouse body weight were measured once every 4 days, and tumor volume (mm3) was calculated using the equation: length×(width)²×0.5. At the end of experiments, mice were sacrificed and tumor nodules were dissected and weighed.

3-2-9. Preliminary Acute Toxicity Assay

Female nu/nu mice (5 weeks old) were P.O. with vehicle (propylene glycol, 0.1 ml) or high dose of 21a (250 and 500 mg/kg) and 35a (500 mg/kg) for 5 days followed by observation of behavior and lethargy for 21 days. There were no behavior alternation and death in these mouse groups in the end of experiment.

REFERENCES

1. Siegel R L, Miller K D, Jemal A., C A Cancer J Clin. 2015; 65(1):5-29.
2. Rajnish Kumar, Anju Sharma, and Rajesh Kumar Tiwari, J Pharm Bioallied Sci. 2012; 4(1): 21-26.
3. David J. Newman and Gordon M. Cragg, J. Nat. Prod., 2012; 75(3):311-335.
4. Vogel, H. A.; Pelletier, J. J. Pharma, 1815, 1, 289.
5. Milobedzka, J.; Kostanecki, S.; Lampe, V. Chemische Berichte, 1910, 43, 2163.
6. L. Ross C. Barclay and Melinda R. Vinqvist, Organic Letters. 2000; 2(18):2841-2843.

7. Ganesh Chandra Jagetia and Golgod Krishnamurthy Rajanikant, Antioxidant., 2015; 4:25-41.
8. Masuda T, Maekawa T, Hidaka K, Bando H, Takeda Y, Yamaguchi H. J Agric Food Chem. 2001; 49(5):2539-47.
9. Zhou, H.; Beevers, C. S.; Huang S. *Current drug targets.* 2011; 12(3): 332-347.
10. Sahdeo Prasad, Subash C. Gupta, Amit K. Tyagi, Bharat B. Aggarwal, Biotechnology Advances. 2014; 32:1053-1064.
11. Aggarwal B B., Kumar A, Bharti A C., Anticancer Res. 2003; 23 (1A):363-398.
12. Muthu K. Shanmugam, Grishma Rane, Madhu Mathi Kanchi, Frank Arfuso, Arunachalam Chinnathambi, M. E. Zayed, Sulaiman Ali Alharbi, Benny K. H. Tan, Alan Pranm Kumar and Gautam Sethi. Molecules, 2015; 20; 2728-2769.
13. Brad. J., J Am Coil Nutr. 2016; 34:347-358.
14. Holder G M, Plummer J L, Ryan A J. Xenobitics, 1978; 8:761-768.
15. Simone I. Hoehle, Erika Pfeiffer, Anikó M. Sólyom and Manfred Metzler, J. Agric. Food Chem., 2006; 54 (3): 756-764.
16. Shaiju K. Vareed, Madhuri Kakarala, Mack T. Ruffin, James A. Crowell, Daniel P. Normolle, Zora Djuric and Dean E. Brenner, Cancer Epidemiol Biomarkers Prev. 2008; 17(6):1411-1417.
17. Wichitnithad, W.; Nimmannit, U.; Wacharasindhu, S.; Rojsitthisak, P. Molecules, 2011; 16:1888-1900.
18. Luyang Ding, Shuli Ma, Hongxiang Lou, Longru Sun and Mei Ji, Molecules, 2015; 20:21501-21504.
19. Konstantin Chegaev, Chiara Riganti, Barbara Rolando, Loretta Lazzarato, Elena Gazzano, Stefano Guglielmo, Dario Ghigo, Roberta Fruttero, Alberto Gasco, Bioorg. Med. Chem. Lett., 2013; 23:5307-5310.
20. Borges G A, Rego D F, Assad D X, Coletta R D, De Luca Canto G and Guerra E N: In vivo and in vitro effects of curcumin on head and neck carcinoma: a systematic review. Journal of oral pathology & medicine: official publication of the International Association of Oral Pathologists and the American Academy of Oral Pathology 2016.
21. Lee D, Kim I Y, Saha S and Choi K S: Paraptosis in the anti-cancer arsenal of natural products. Pharmacology & therapeutics 2016.
22. Ferrucci V, Boffa I, De Masi G and Zollo M: Natural compounds for pediatric cancer treatment. Naunyn-Schmiedeberg's archives of pharmacology 389: 131-149, 2016.
23. Sordillo P P and Helson L: Curcumin and cancer stem cells: curcumin has asymmetrical effects on cancer and normal stem cells. Anticancer research 35: 599-614, 2015.
24. Iqbal B, Ghildiyal A, Sahabjada, et al: Antiproliferative and Apoptotic Effect of Curcumin and TRAIL (TNF Related Apoptosis inducing Ligand) in Chronic Myeloid Leukaemic Cells. Journal of clinical and diagnostic research: JCDR 10: XC01-XC05, 2016.
25. Zhang L, Cheng X, Gao Y, et al: Induction of ROS-independent DNA damage by curcumin leads to G2/M cell cycle arrest and apoptosis in human papillary thyroid carcinoma BCPAP cells. Food & function 7: 315-325, 2016.
26. Huang Y T, Lin Y W, Chiu H M and Chiang B H: Curcumin Induces Apoptosis of Colorectal Cancer Stem Cells by Coupling with CD44 Marker. Journal of agricultural and food chemistry 64: 2247-2253, 2016.
27. Kantara C, O'Connell M, Sarkar S, Moya S, Ullrich R and Singh P: Curcumin promotes autophagic survival of a subset of colon cancer stem cells, which are ablated by DCLK1-siRNA. Cancer research 74: 2487-2498, 2014.

The invention claimed is:

1. A compound having the following formula:

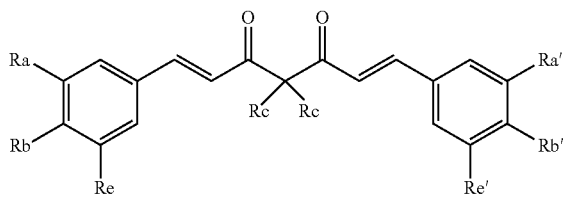

wherein Ra, Rb, Ra' and Rb' independently are H, halogen, C1-C6 alkyl, C1-C6 alkoxy, C1-C6 fluoroalkoxy, amino, amino(C1-C6 alkyl), nitro, heteroaryl, OH, -OC(=O)Rd, -OC(=O)ORd, or -OC(=O)N(Rd)$_2$, wherein Rd is H, C1-C6 alkyl, or C1-C9 alkylol; Rc is H, C1-C6 alkyl, C3-C6 unsaturated alkyl with a double or triple bond, C1-C9 alkylol, C7-C12 arylalkyl, or -CH2-OC(=O)Rd; and Re and Re' independently are H, C1-C6 alkyl, C1-C6 alkoxy;

wherein at least one of Ra, Rb, Ra', and Rb' is -OC(=O)Rd, wherein Rd is a C3-C9 branched alkylol; or Rc is -CH$_2$-OC(=O)Rd, wherein Rd is C1-C3 alkyl, or a C3-C9 branched alkylol;

wherein said compound is interconvertible between keto and enol forms, when Rc is H, or a pharmaceutically acceptable salt thereof.

2. The compound of claim 1, wherein Rc is H, and at least one of Ra, Rb, Ra' and Rb' is -OC(=O)Rd, and Rd is a C3-C9 branched alkylol.

3. The compound of claim 2, wherein Rd is -C(CH$_3$)(CH$_2$OH)$_2$, -C(C$_2$H$_5$)(CH$_2$OH)$_2$, -C(CH$_2$OH)$_3$, or -C(CH$_2$OH)$_2$(CH$_2$OC(=O)C(CH$_2$OH)$_3$).

4. The compound of claim 3, which one or two of Ra, Rb, Ra' and Rb' are -OC(=O)Rd, Rd is -C(CH$_3$)(CH$_2$OH)$_2$, and the remaining of Ra, Rb, Ra' and Rb' are H, OH, CH$_3$, C$_2$H$_5$, OCH$_3$, OC$_2$H$_5$, OCF$_3$; Re and Re' are H, CH$_3$, C$_2$H$_5$, OCH$_3$, or OC$_2$H$_5$.

5. The compound of claim 1, wherein Rc is methyl, ethyl, benzyl, propagyl, allyl, CH$_2$OH, CH$_2$OC(=O)CH$_3$, or CH$_2$OC(=O)Rd, wherein Rd is -C(CH$_3$)(CH$_2$OH)$_2$, -C(C$_2$H$_5$)(CH$_2$OH)$_2$, -C(CH$_2$OH)$_3$, or -C(CH$_2$OH)$_2$(CH$_2$OC(=O)C(CH$_2$OH)$_3$); Re and Re' are H; and Ra, Rb, Ra' and Rb' independently are H, OH, C1-C6 alkoxy, or -OC(=O)Rd, wherein Rd is -C(CH$_3$)(CH$_2$OH)$_2$, -C(C$_2$H$_5$)(CH$_2$OH)$_2$, -C(CH$_2$OH)$_3$, or -C(CH$_2$OH)$_2$(CH$_2$OC(=O)C(CH$_2$OH)$_3$).

6. The compound of claim 5, wherein Rc is methyl, ethyl, benzyl, propagyl, allyl, CH$_2$OH, CH$_2$OC(=O)CH$_3$, or CH$_2$OC(=O)C(CH$_3$)(CH$_2$OH)$_2$; and Ra, Rb, Ra' and Rb' independently are H, OH, methoxy, or -OC(=O)Rd, wherein Rd is -C(CH$_3$)(CH$_2$OH)$_2$, -C(CH$_2$OH)$_3$, or -C(CH$_2$OH)$_2$(CH$_2$OC(=O)C(CH$_2$OH)$_3$).

7. The compound of claim 3, wherein the compound is selected from the group consisting of the following compounds 21a to 31, 33, 38a and 38b:

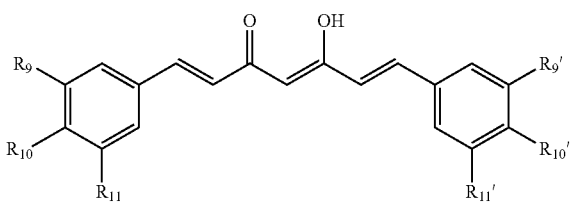

wherein
21a $R_9$, $R_9'$=OCH$_3$; $R_{10}$, $R_{10}'$=OR$_{12}$; $R_{11}'$=H
21b $R_9$, $R_9'$=OCH$_3$; $R_{10}$=OR$_{12}$, $R_{10}'$=OH; $R_{11}$, $R_{11}'$=H
22a $R_9$, $R_9'$=OCH$_3$; $R_{10}$, $R_{10}'$=OR$_{12}'$; $R_{11}$, $R_{11}'$=H
22b $R_9$, $R_9'$=OCH$_3$; $R_{10}$=OR$_{12}'$, $R_{10}'$=OH; $R_{11}'$=H
23a $R_9$, $R_9'$=H; $R_{10}$, $R_{10}'$=OR$_{12}$; $R_{11}'$=H
23b $R_9$, $R_9'$=H; $R_{10}$=OR$_{12}$, $R_{10}'$=OH; $R_{11}$, $R_{11}'$=H
24a $R_9$, $R_9'$=OR$_{12}$; $R_{10}$, $R_{10}'$=OCH$_3$; $R_{11}$, $R_{11}'$=H
24b $R_9$=OR$_{12}$, $R_9'$=OH; $R_{10}$, $R_{10}'$=OCH$_3$; $R_{11}$, $R_{11}'$=H
25 $R_9$=OR$_{12}'$, $R_9'$=OH; $R_{10}$, $R_{10}'$=OCH$_3$; $R_{11}$, $R_{11}'$=H
26 $R_9$, $R_9'$=OC$_2$H$_5$; $R_{10}$, $R_{10}'$=OR$_{12}$; $R_{11}$, $R_{11}'$=H
27 $R_9$, $R_9'$=OC$_2$H$_5$; $R_{10}$, $R_{10}'$=OR$_{12}'$; $R_{11}$, $R_{11}'$=H
28 $R_9$, $R_9'$=OCF$_3$; $R_{10}$, $R_{10}'$=OR$_{12}$; $R_{11}$, $R_{11}'$=H
29 $R_9$, $R_9'$=OCF$_3$; $R_{10}$, $R_{10}'$=OR$_{12}'$; $R_{11}$, $R_{11}'$=H
30 $R_9$, $R_9'$=OCH$_3$; $R_{10}$, $R_{10}'$=OR$_{12}$; $R_{11}$, $R_{11}'$=OCH$_3$
31 $R_9$, $R_9'$=C$_2$H$_5$; $R_{10}$, $R_{10}'$=OR$_{12}$; $R_{11}$, $R_{11}'$=C$_2$H$_5$
wherein

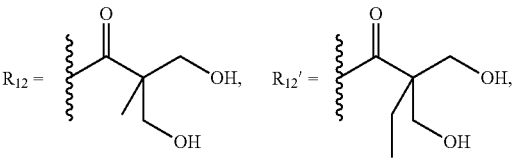

8. The compound of claim 6, wherein the compound is selected from the group consisting of the following compounds 35a to 41, 43, and 44:

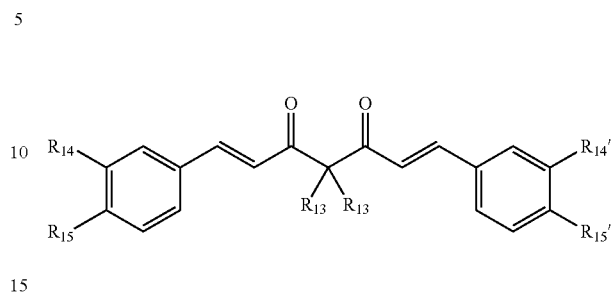

wherein
35a $R_{14}$, $R_{14}'$=OCH$_3$; $R_{15}$, $R_{15}'$=OR$_{12}$; $R_{13}$=Me
35b $R_{14}$, $R_{14}'$=OCH$_3$; $R_{15}$, $R_{15}'$=OR$_{12}$; $R_{13}$=Et
35c $R_{14}$, $R_{14}'$=OCH$_3$; $R_{15}$, $R_{15}'$=OR$_{12}$; $R_{13}$=Bn
35d $R_{14}$, $R_{14}'$=OCH$_3$; $R_{15}$, $R_{15}'$=OR$_{12}$; $R_{13}$=Propagyl
35e $R_{14}$, $R_{14}'$=OCH$_3$; $R_{15}$, $R_{15}'$=OR$_{12}$; $R_{13}$=Allyl
36 $R_{14}$, $R_{14}'$=H; $R_{15}$, $R_{15}'$=OR$_{12}$; $R_{13}$=Me
37 $R_{14}$, $R_{14}'$=OR$_{12}$; $R_{15}$, $R_{15}'$=OCH$_3$; $R_{13}$=Me

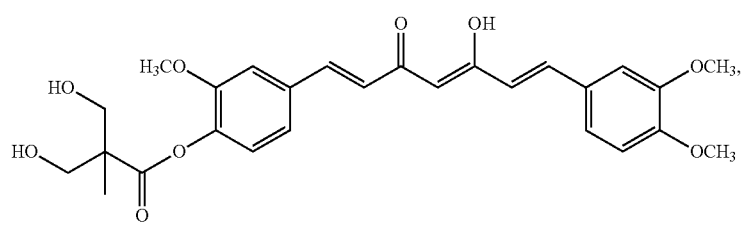

33

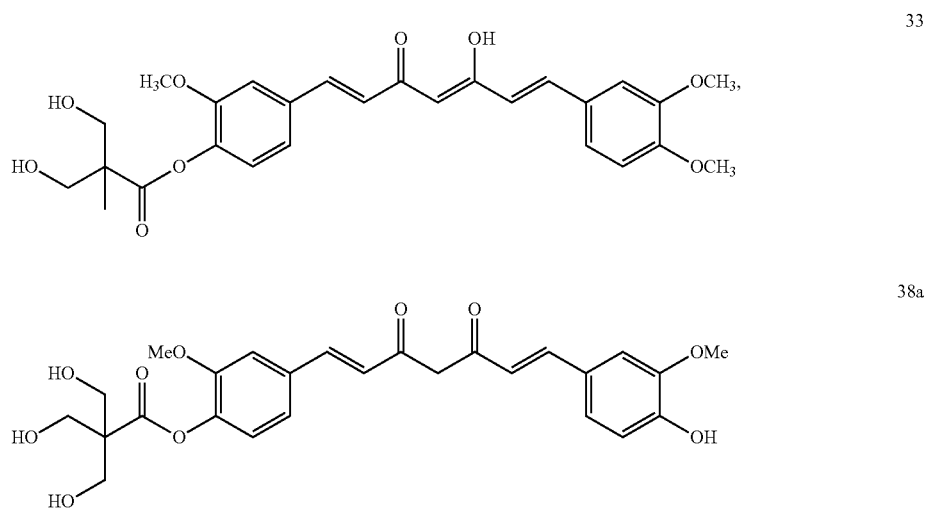

38a

38b

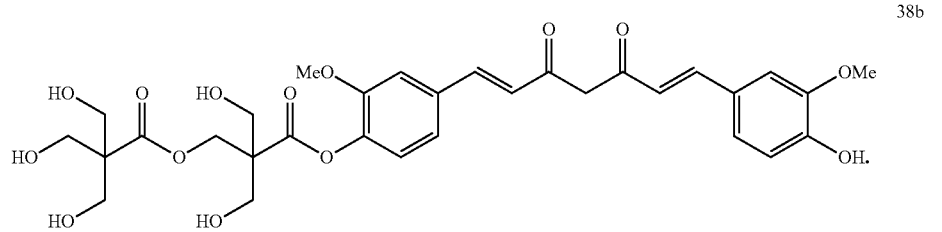

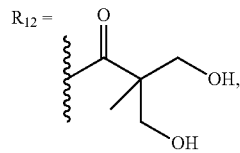

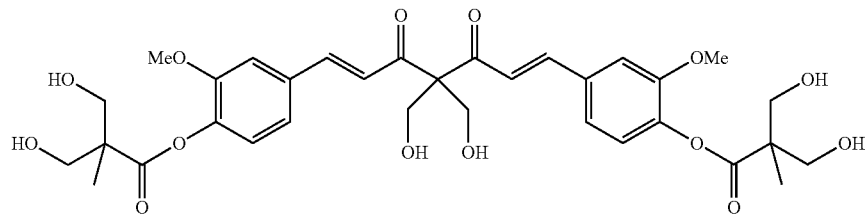

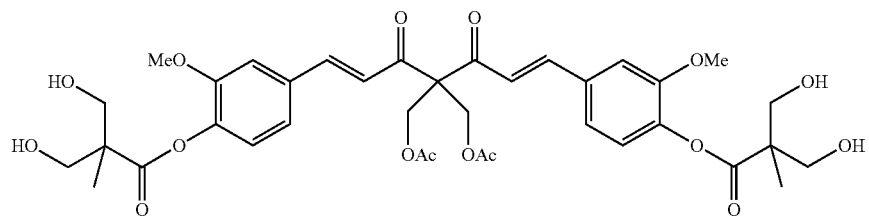

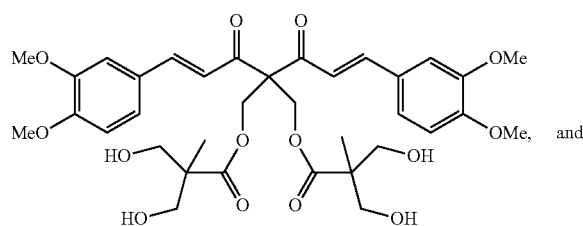

wherein in the compounds 35a to 41, 43, and 44, Me is methyl, Et is ethyl, Bn is benzyl, and Ac is acetyl, C(=O)CH$_3$.

9. A method for inhibiting growth of cancer cells comprising administering a compound according to claim 1 or a pharmaceutically acceptable salt thereof to a subject suffering cancer in need of said inhibition, wherein said cancer is breast cancer, colon cancer or prostate cancer.

10. The method of claim 9, wherein the cancer is breast cancer.

11. The method of claim 10, wherein the breast cancer is Triple-Negative Breast cancer.

12. A pharmaceutical composition for treating a cancer in a subject comprising a therapeutically effective amount for said treatment of a compound according to claim 1 or a pharmaceutically acceptable salt thereof, wherein the cancer is breast cancer, colon cancer or prostate cancer.

13. The pharmaceutical composition of claim 12, wherein the cancer is breast cancer.

14. The pharmaceutical composition of claim 13, wherein the breast cancer is Triple-Negative Breast cancer.

15. The pharmaceutical composition of claim 14 further comprising a therapeutically effective amount for said treatment of Doxorubicin.

16. The method of claim 9, wherein Rc is H, and at least one of Ra, Rb, Ra' and Rb' is -OC(=O)Rd, and Rd is a C3-C9 branched alkylol.

17. The method of claim 11, wherein Rd is -C(CH$_3$)(CH$_2$OH)$_2$, -C(C$_2$H$_5$)(CH$_2$OH)$_2$, -C(CH$_2$OH)$_3$, or -C(CH$_2$OH)$_2$(CH$_2$OC(=O)C(CH$_2$OH)$_3$).

18. The pharmaceutical composition of claim 12, which one or two of Ra, Rb, Ra' and Rb' are -OC(=O)Rd, Rd is -C(CH$_3$)(CH$_2$OH)$_2$, and the remaining of Ra, Rb, Ra' and Rb' are H, OH, CH$_3$, C$_2$H$_5$, OCH$_3$, OC$_2$H$_5$, OCF$_3$; Re and Re' are H, CH$_3$, C$_2$H$_5$, OCH$_3$, or OC$_2$H$_5$.

19. The method of claim 9, wherein Rc is methyl, ethyl, benzyl, propagyl, allyl, CH$_2$OH, CH$_2$OC(=O)CH$_3$, or CH$_2$OC(=O)Rd, wherein Rd is -C(CH$_3$)(CH$_2$OH)$_2$, -C(C$_2$H$_5$)(CH$_2$OH)$_2$, -C(CH$_2$OH)$_3$, or -C(CH$_2$OH)$_2$(CH$_2$OC(=O)C(CH$_2$OH)$_3$); Re and Re' are H; and Ra, Rb, Ra' and Rb' independently are H, OH, C1-C6 alkoxy, or -OC(=O)Rd, wherein Rd is -C(CH$_3$)(CH$_2$OH)$_2$, -C(C$_2$H$_5$)(CH$_2$OH)$_2$, -C(CH$_2$OH)$_3$, or -C(CH$_2$OH)$_2$(CH$_2$OC(=O)C(CH$_2$OH)$_3$).

20. The pharmaceutical composition of claim 13, wherein Rc is methyl, ethyl, benzyl, propagyl, allyl, CH$_2$OH, CH$_2$OC(=O)CH$_3$, or CH$_2$OC(=O)C(CH$_3$)(CH$_2$OH)$_2$; and Ra, Rb, Ra' and Rb' independently are H, OH, methoxy, or -OC(=O)Rd, wherein Rd is -C(CH$_3$)(CH$_2$OH)$_2$, -C(CH$_2$OH)$_3$, or -C(CH$_2$OH)$_2$(CH$_2$OC(=O)C(CH$_2$OH)$_3$).

* * * * *